US010223931B1

(12) United States Patent
Clark et al.

(10) Patent No.: US 10,223,931 B1
(45) Date of Patent: Mar. 5, 2019

(54) SYSTEMS AND METHODS FOR COMPENSATION ANALYSIS AND TARGETED, CORRECTIVE PROGRAM GENERATION

(71) Applicant: Fusionetics, LLC, Alpharetta, GA (US)

(72) Inventors: Michael Alan Clark, Milton, GA (US); Tyler Warren Alexander Wallace, Chandler, AZ (US); David Montgomery Tate, Woodstock, GA (US)

(73) Assignee: Fusionetics, LLC, Alpharetta, GA (US)

( * ) Notice: Subject to any disclaimer, the term of this patent is extended or adjusted under 35 U.S.C. 154(b) by 11 days.

(21) Appl. No.: 14/846,345

(22) Filed: Sep. 4, 2015

Related U.S. Application Data

(60) Provisional application No. 62/046,520, filed on Sep. 5, 2014.

(51) Int. Cl.
| | | |
|---|---|---|
| *G01N 33/48* | (2006.01) | |
| *G09B 19/00* | (2006.01) | |
| *A61B 5/11* | (2006.01) | |
| *G06F 19/00* | (2018.01) | |
| *G09B 5/02* | (2006.01) | |

(52) U.S. Cl.
CPC ............ *G09B 19/003* (2013.01); *A61B 5/11* (2013.01); *G06F 19/3481* (2013.01); *G09B 5/02* (2013.01)

(58) Field of Classification Search
None
See application file for complete search history.

(56) References Cited

U.S. PATENT DOCUMENTS

| | | |
|---|---|---|
| 6,073,489 A | 6/2000 | French et al. |
| 6,740,007 B2 | 5/2004 | Gordon et al. |
| 7,492,268 B2 | 2/2009 | Ferguson et al. |
| 7,771,320 B2 | 8/2010 | Riley et al. |
| 7,967,728 B2 | 6/2011 | Zavadsky et al. |
| 8,246,555 B2 | 8/2012 | Chiu et al. |
| 8,428,357 B2 | 4/2013 | Stephenson |
| 8,527,217 B2 | 9/2013 | Moodie |
| 8,636,605 B2 | 1/2014 | Rose |
| 8,762,167 B2 | 6/2014 | Blander et al. |
| 8,968,156 B2 | 3/2015 | Ellis et al. |
| 2002/0082143 A1 | 6/2002 | Leeds |

(Continued)

OTHER PUBLICATIONS

Alexander, Gregory L., et al., An Analysis of Human Motion Detection Systems Use During Elder Exercise Routines, Western Journal of Nursing Research, 2009, pp. 1-17.

(Continued)

*Primary Examiner* — Larry D Riggs, II
(74) *Attorney, Agent, or Firm* — Morris, Manning & Martin, LLP; Daniel E. Sineway, Esq.; R. Lee Strasburger, Jr., Esq.

(57) ABSTRACT

Systems and methods for objectively assessing physical performance of a subject and generating programs specifically tailored to correct any physical deficiencies identified during that assessment. Generally, the assessments may produce results in binary format so that the assessments may be conducted objectively. Additionally, the recommended exercise programs may be generated based on the results of those assessments so that the recommended exercise programs target the identified physical deficiencies.

17 Claims, 30 Drawing Sheets

EXEMPLARY COMPENSATION ANALYSIS AND
PROGRAM GENERATION SYSTEM OVERVIEW

(56) References Cited

U.S. PATENT DOCUMENTS

| | | |
|---|---|---|
| 2002/0082144 A1 | 6/2002 | Pfeffer et al. |
| 2004/0241629 A1 | 12/2004 | Ondrusz et al. |
| 2006/0058699 A1 | 3/2006 | Vitiello et al. |
| 2007/0087913 A1 | 4/2007 | Jaquish et al. |
| 2007/0219059 A1 | 9/2007 | Schwartz et al. |
| 2007/0232450 A1 | 10/2007 | Hanoun |
| 2008/0103023 A1 | 5/2008 | Chung et al. |
| 2008/0119763 A1 | 5/2008 | Wiener |
| 2008/0220941 A1 | 9/2008 | Shaw et al. |
| 2008/0242521 A1 | 10/2008 | Einav et al. |
| 2009/0047644 A1 | 2/2009 | Mensah et al. |
| 2009/0210078 A1 | 8/2009 | Crowley et al. |
| 2009/0270228 A1 | 10/2009 | Holle et al. |
| 2010/0302138 A1* | 12/2010 | Poot ................ G06F 3/011 345/156 |
| 2011/0246509 A1 | 10/2011 | Migita et al. |
| 2011/0281249 A1 | 11/2011 | Gammell et al. |
| 2012/0029666 A1 | 2/2012 | Crowley et al. |
| 2012/0040799 A1 | 2/2012 | Jaquish et al. |
| 2012/0071732 A1 | 3/2012 | Grey et al. |
| 2012/0144301 A1 | 6/2012 | Bass |
| 2012/0183939 A1 | 7/2012 | Aragones et al. |
| 2012/0196256 A1 | 8/2012 | Maeueler et al. |
| 2012/0202184 A1 | 8/2012 | O'Prinsen et al. |
| 2012/0277891 A1 | 11/2012 | Aragones et al. |
| 2013/0028491 A1 | 1/2013 | Stephenson et al. |
| 2013/0040272 A1 | 2/2013 | Booher |
| 2013/0063432 A1 | 3/2013 | Kaps et al. |
| 2013/0066859 A1 | 3/2013 | Young et al. |
| 2013/0095959 A1 | 4/2013 | Marty et al. |
| 2013/0190657 A1 | 7/2013 | Flaction et al. |
| 2013/0211562 A1 | 8/2013 | Winter et al. |
| 2013/0218309 A1 | 8/2013 | Napolitano et al. |
| 2013/0223707 A1 | 8/2013 | Stephenson et al. |
| 2013/0281888 A1 | 10/2013 | Bender et al. |
| 2013/0282157 A1 | 10/2013 | Shin et al. |
| 2014/0031703 A1 | 1/2014 | Rayner et al. |
| 2014/0039353 A1 | 2/2014 | Ziegler |
| 2014/0087341 A1 | 3/2014 | Hall et al. |
| 2014/0088995 A1 | 3/2014 | Damani et al. |
| 2014/0156308 A1 | 6/2014 | Ohnemus et al. |
| 2014/0172444 A1 | 6/2014 | Moore et al. |
| 2014/0214446 A1 | 7/2014 | Nusbaum et al. |
| 2014/0228985 A1 | 8/2014 | Elliott et al. |
| 2014/0270711 A1 | 9/2014 | Maser et al. |
| 2014/0371633 A1 | 12/2014 | Evin et al. |
| 2015/0066170 A1 | 3/2015 | Harris et al. |
| 2015/0170530 A1 | 6/2015 | Damman et al. |
| 2015/0231444 A1 | 8/2015 | Stephenson |

OTHER PUBLICATIONS

DiStefano, et al., Influence of Age, Sex, Technique, and Exercise Program on Movement Patterns After an Anterior Cruciate Ligament Injury Prevention Program in Youth Soccer Players, The American Journal of Sports Medicine, vol. 37, No. 3, 2009, pp. 1-1.

Marcus, et al., Telephone Versus Print Delivery of an Individualized Motivationally Tailored Physical Activity Intervention: Project STRIDE, Health Psychology, 2007, vol. 26, No. 4, pp. 401-409.

Exercise Order—How to Arrange the Exercises in Your Workout; Nov. 11, 2013; A Workout Routine; https://www.aworkoutroutine.com/exercise-order/.

Hoffman, Jay R., NSCA's Guide to Program Desgin, 2012, Human Kinetics, http://www.humankinetics.com/excerpts/excerpts/utilize-proper-workout-structure-and-exercise-order.

* cited by examiner

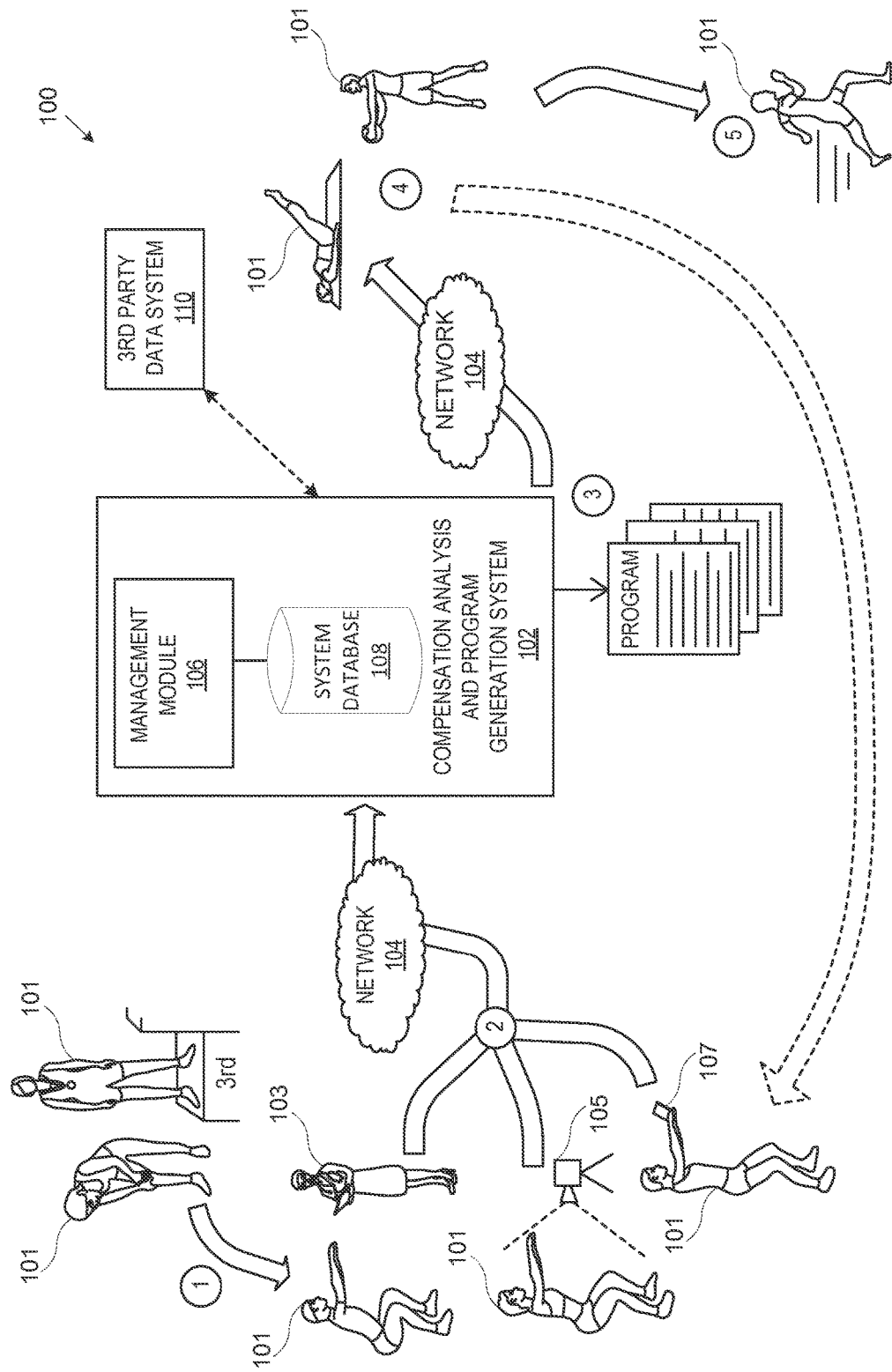
FIG. 1: EXEMPLARY COMPENSATION ANALYSIS AND PROGRAM GENERATION SYSTEM OVERVIEW

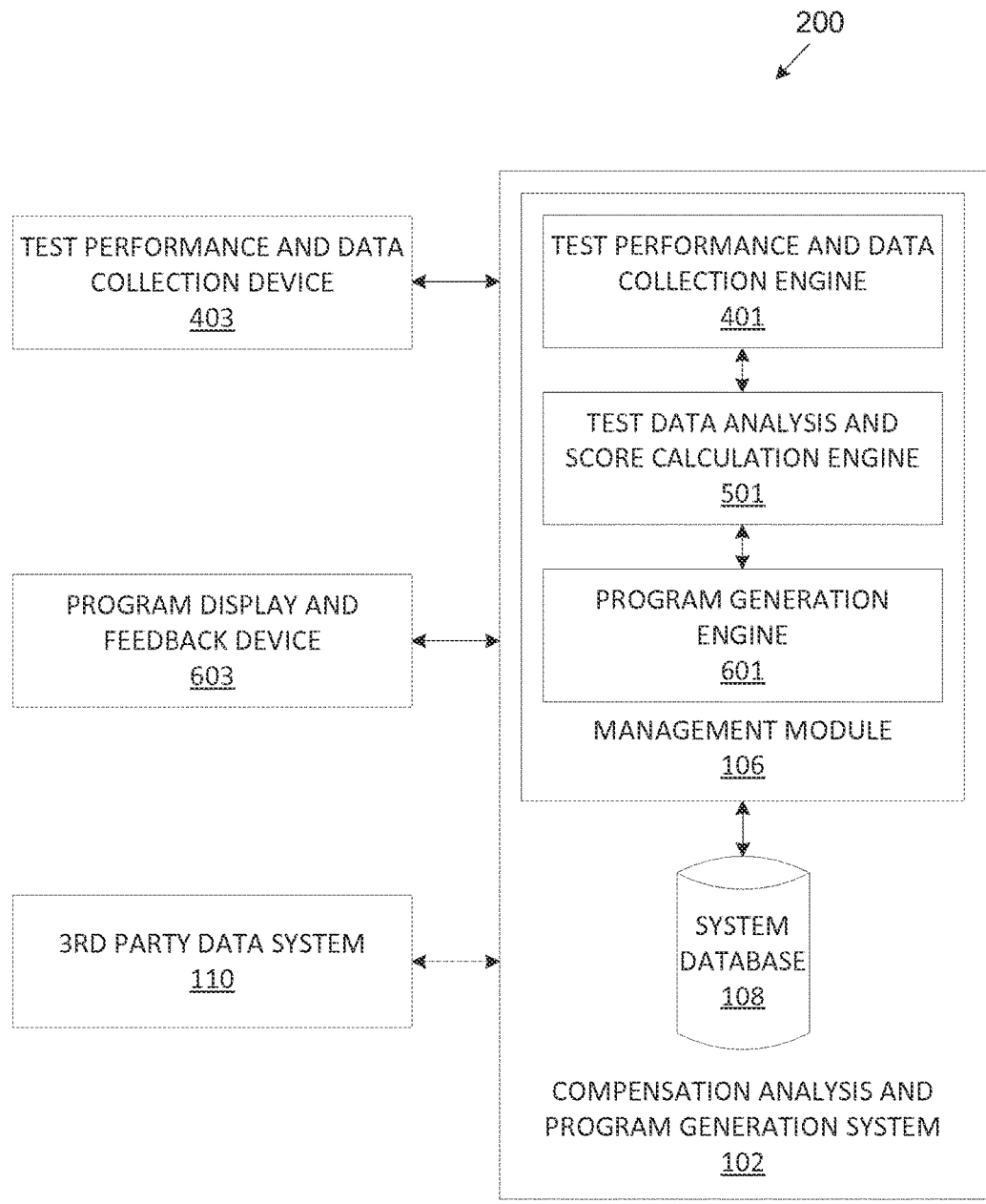
FIG 2: EXEMPLARY SYSTEM ARCHITECTURE

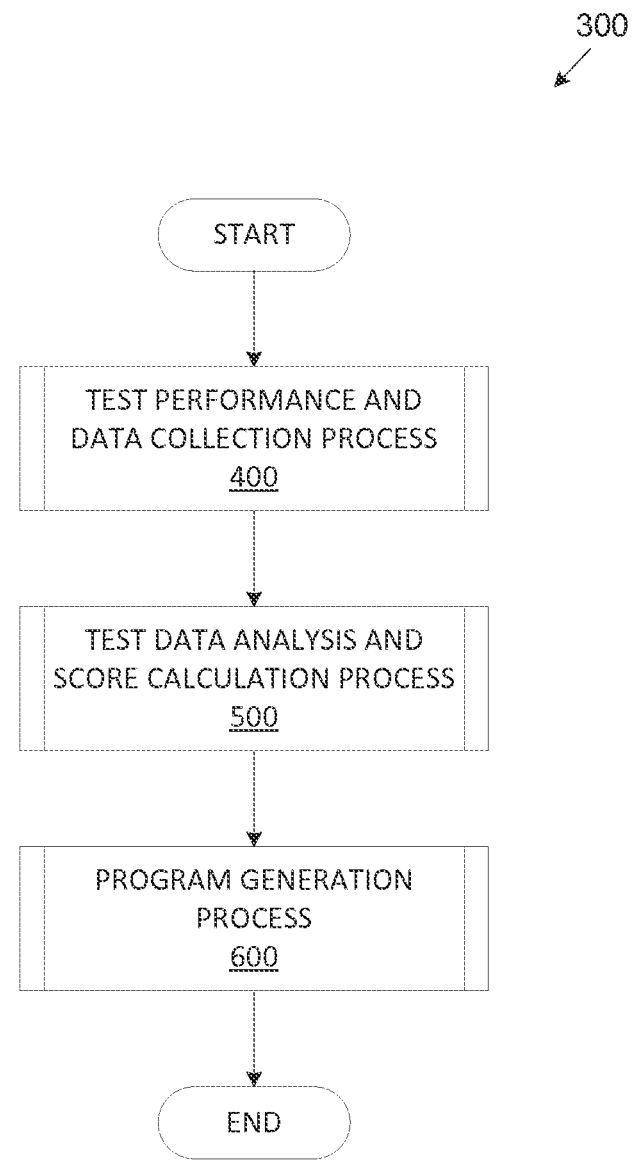
FIG 3: EXEMPLARY PROCESS FLOW

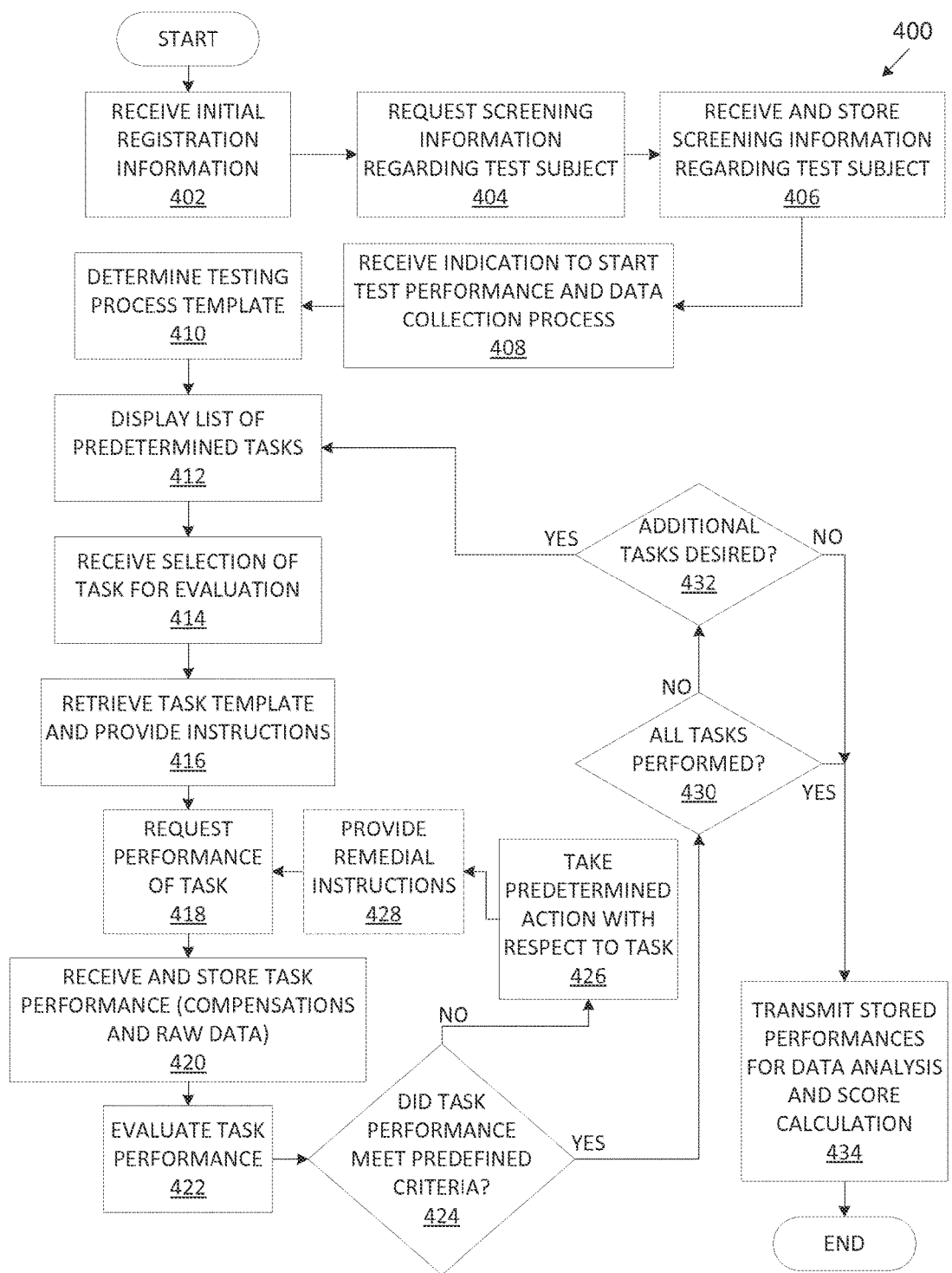
FIG 4: EXEMPLARY TEST PERFORMANCE AND DATA COLLECTION PROCESS

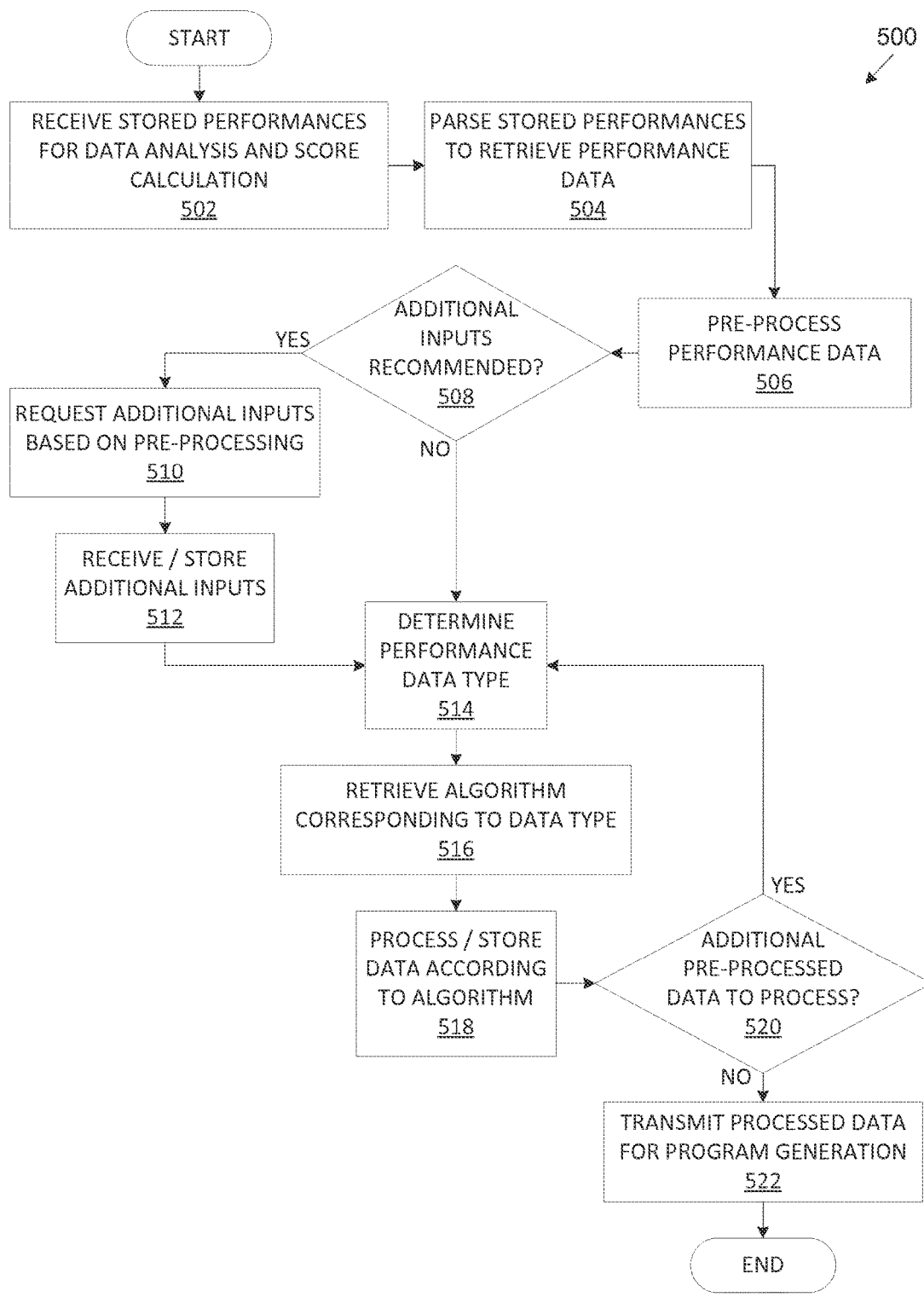
FIG 5: EXEMPLARY TEST DATA ANALYSIS AND SCORE CALCULATION PROCESS

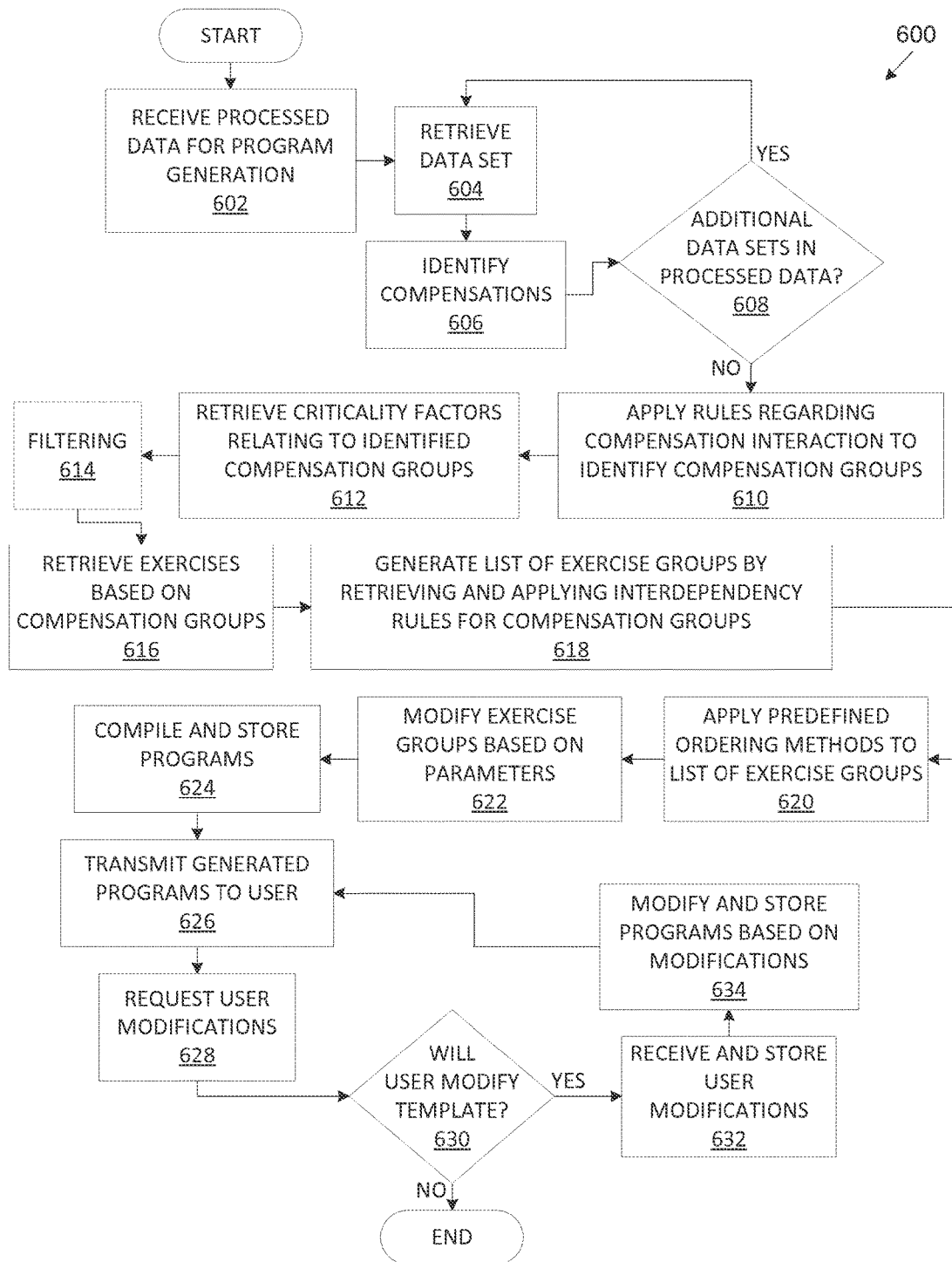
FIG 6: EXEMPLARY PROGRAM GENERATION PROCESS

*FIG. 7*: EXEMPLARY SUBJECT ROSTER SCREENSHOT

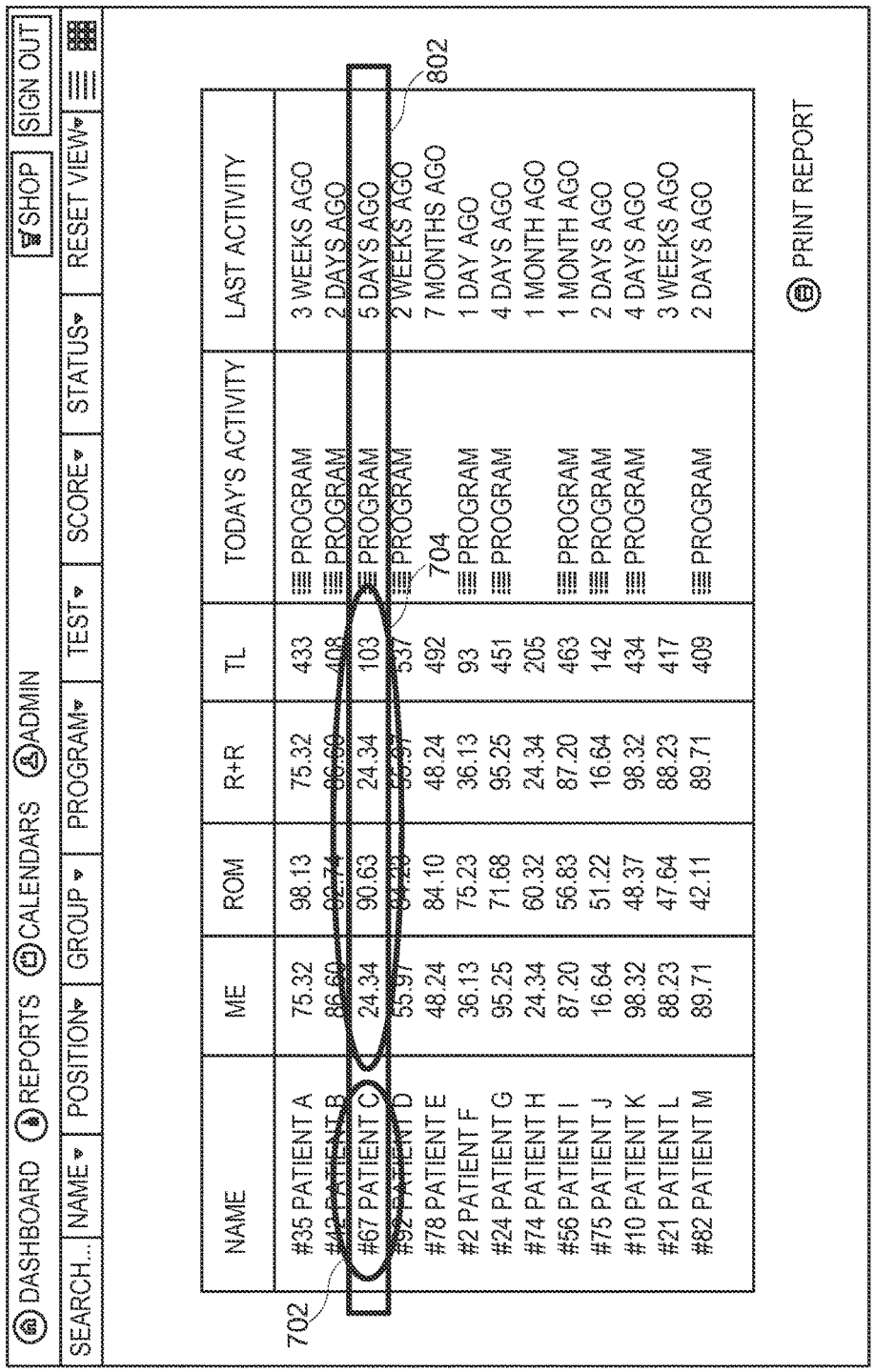
FIG. 8: EXEMPLARY SUBJECT ROSTER (LIST VIEW) SCREENSHOT

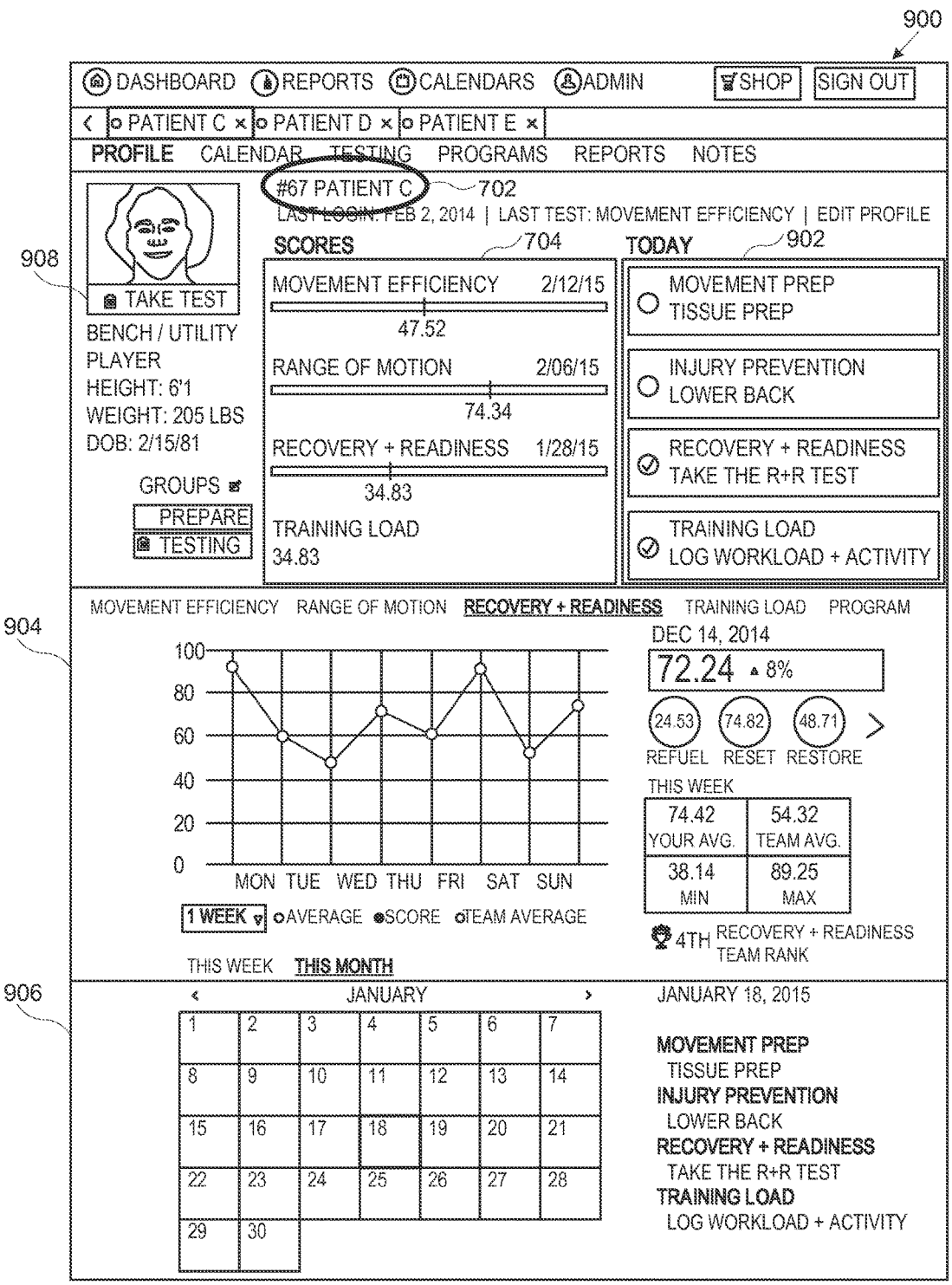
FIG. 9: EXEMPLARY SUBJECT SUMMARY SCREENSHOT

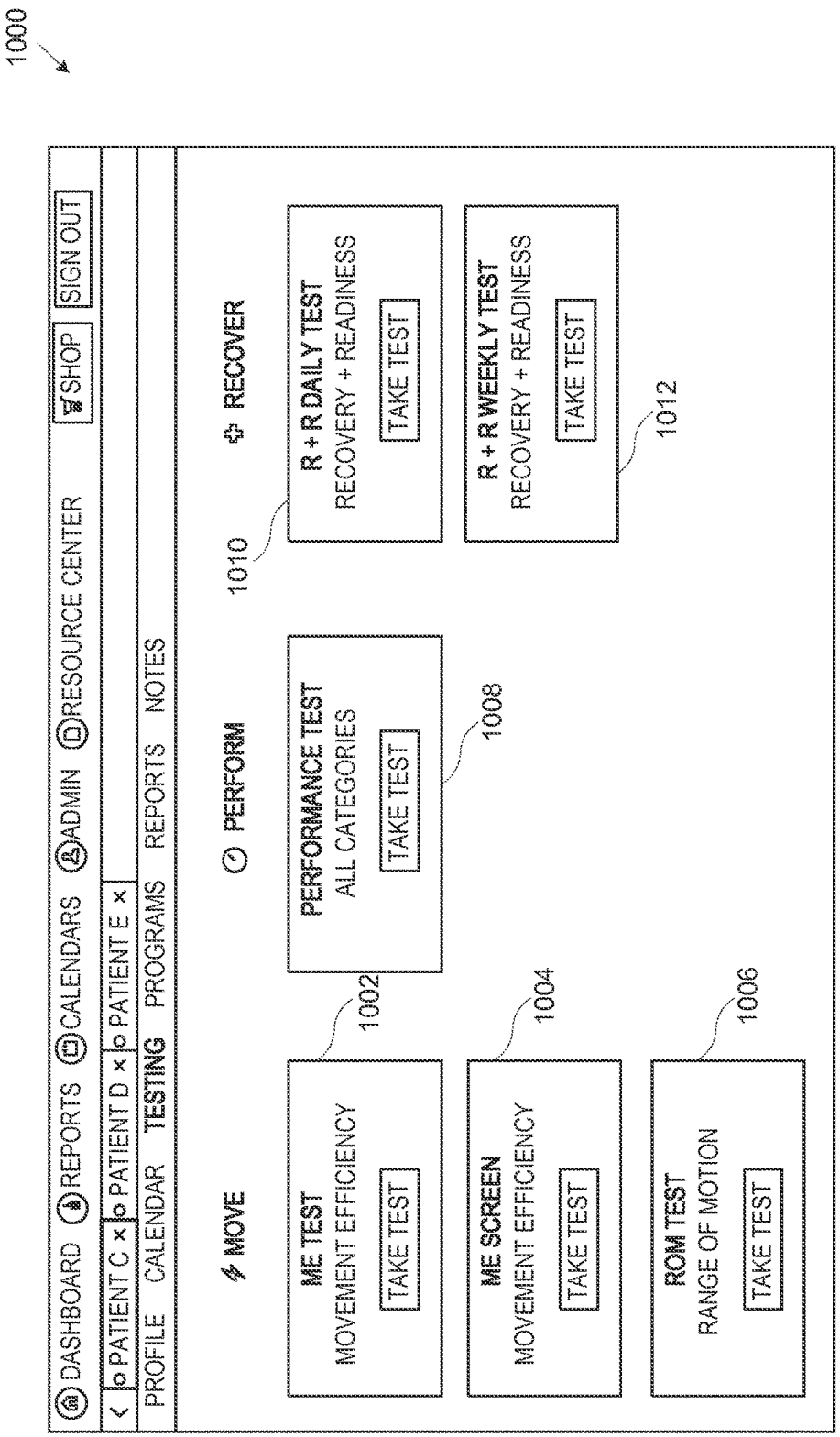
FIG. 10: EXEMPLARY TEST-SELECTION SCREENSHOT

*FIG. 11*: EXEMPLARY MOVEMENT EFFICIENCY TEST PERFORMANCE AND DATA COLLECTION SCREENSHOT

FIG. 12: EXEMPLARY MOVEMENT EFFICIENCY SCREEN PERFORMANCE AND DATA COLLECTION SCREENSHOT

| DASHBOARD | REPORTS | CALENDARS | ADMIN | SHOP | SIGN OUT |

PATIENT C ×  PATIENT D ×  PATIENT E ×

PROFILE  CALENDAR  TESTING  PROGRAMS  REPORTS  NOTES

RANGE OF MOTION TEST

TEST DATE: APRIL 28, 2015
PRINT TEST FORM

| ROM SCORE (RIGHT) 82.45 | ROM SCORE (LEFT) 54.78 | OVERALL TEST SCORE 75.42 |

| JOINT / MOTION | OPTIMAL ROM | ACTUAL ROM (RIGHT) | ACTUAL ROM (LEFT) |
|---|---|---|---|
| 1ST MTP TOE EXTENSION | 70° | 64  91.43% | 74  91.43% |
| ANKLE DORSIFLEXION | 20° | 10  17.14% | 12  34.14% |
| KNEE EXTENSION - 90/90 | 20° | 14  56.64% | 12  63.54% |
| HIP ABDUCTION | 45° | 42  91.54% | 57  91.54% |
| HIP INTERNAL ROTATION | 45° | ENTER | ENTER |
| HIP EXTERNAL ROTATION | 45° | ENTER | ENTER |
| HIP EXTENSION (SUPINE) W/ KNEE FLEXION | -5° | ENTER | ENTER |
| SHOULDER FLEXION | 160° | ENTER | ENTER |
| SHOULDER INTERNAL ROTATION | 70° | ENTER | ENTER |
| SHOULDER EXTERNAL ROTATION | 90° | ENTER | ENTER |
| ANKLE DORSIFLEXION W/ KNEE FLEXION | 70° | ENTER | ENTER |
| ANKLE PLANTARFLEXION | 20° | ENTER | ENTER |
| ANKLE INVERSION | 20° | ENTER | ENTER |
| ANKLE EVERSION | 45° | ENTER | ENTER |
| KNEE FLEXION | 45° | ENTER | ENTER |
| HIP EXTENSION (SUPINE) | 45° | ENTER | ENTER |
| HIP EXTENSION (SUPINE) W/ FEMORAL ADDUCTION | -5° | ENTER | ENTER |
| HIP FLEXION (BENT KNEE) | 160° | ENTER | ENTER |
| SHOULDER ABDUCTION | 70° | ENTER | ENTER |
| ELBOW FLEXION | 90° | ENTER | ENTER |
| ELBOW EXTENSION | 70° | ENTER | ENTER |
| PRORATION | 20° | ENTER | ENTER |
| SUPINATION | 20° | ENTER | ENTER |
| FLEXION | 45° | ENTER | ENTER |
| EXTENSION | 45° | ENTER | ENTER |
| RADIAL DEVIATION | 45° | ENTER | ENTER |
| ULNAR DEVIATION | -5° | ENTER | ENTER |
| CERVICAL ROTATION | 160° | ENTER | ENTER |
| CERVICAL LATERAL FLEXION | 70° | ENTER | ENTER |
| CERVICAL FLEXION | 90° | ENTER | ENTER |
| THORACIC LATERAL FLEXION | 70° | ENTER | ENTER |
| THORACIC TRUNK ROTATION | 90° | ENTER | ENTER |

- SHOW LESS

| SAVE CHANGES | COMPLETE TEST |

*FIG. 13:* EXEMPLARY RANGE OF MOTION TEST PERFORMANCE AND DATA COLLECTION SCREENSHOT

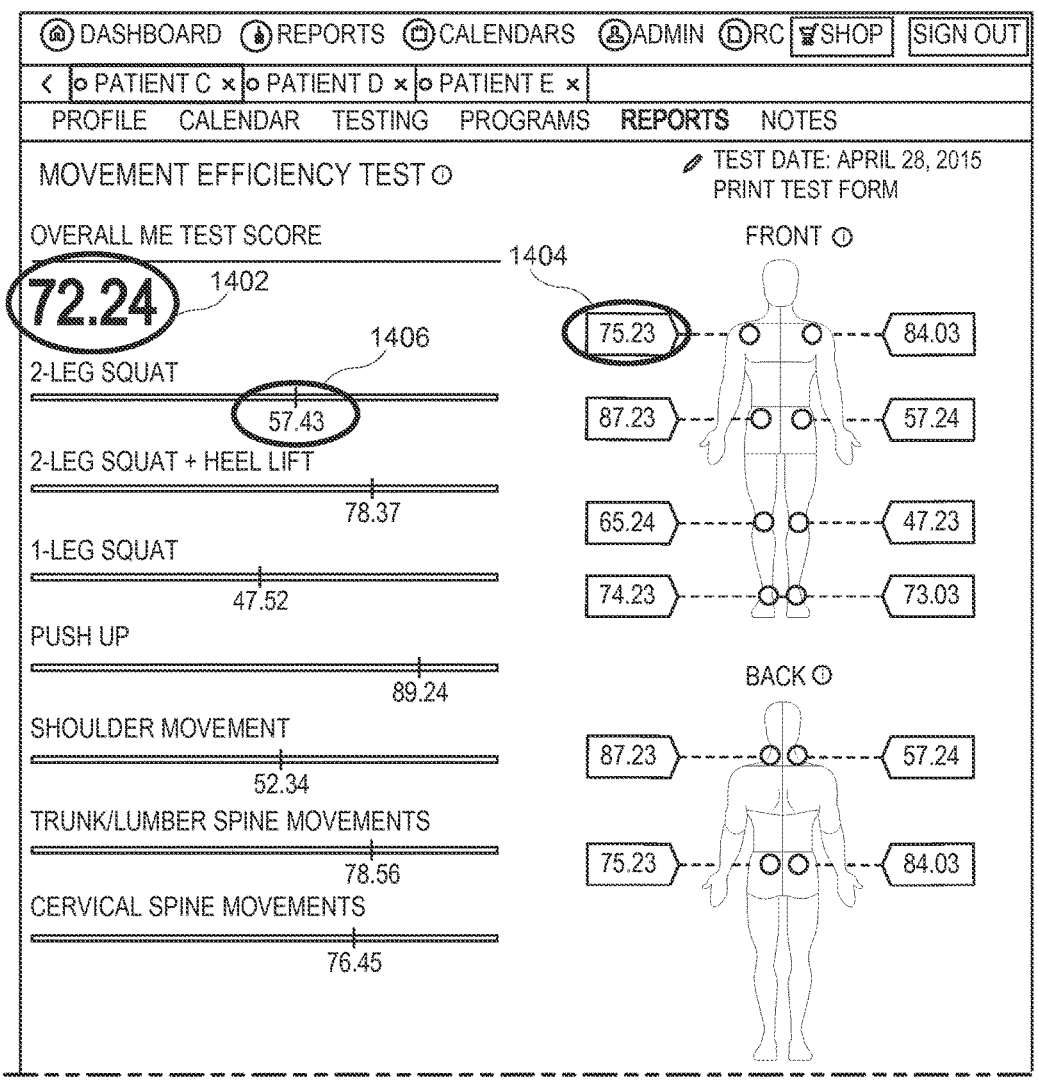
*FIG. 14A:* EXEMPLARY MOVEMENT EFFICIENCY TEST REPORT SCREENSHOT

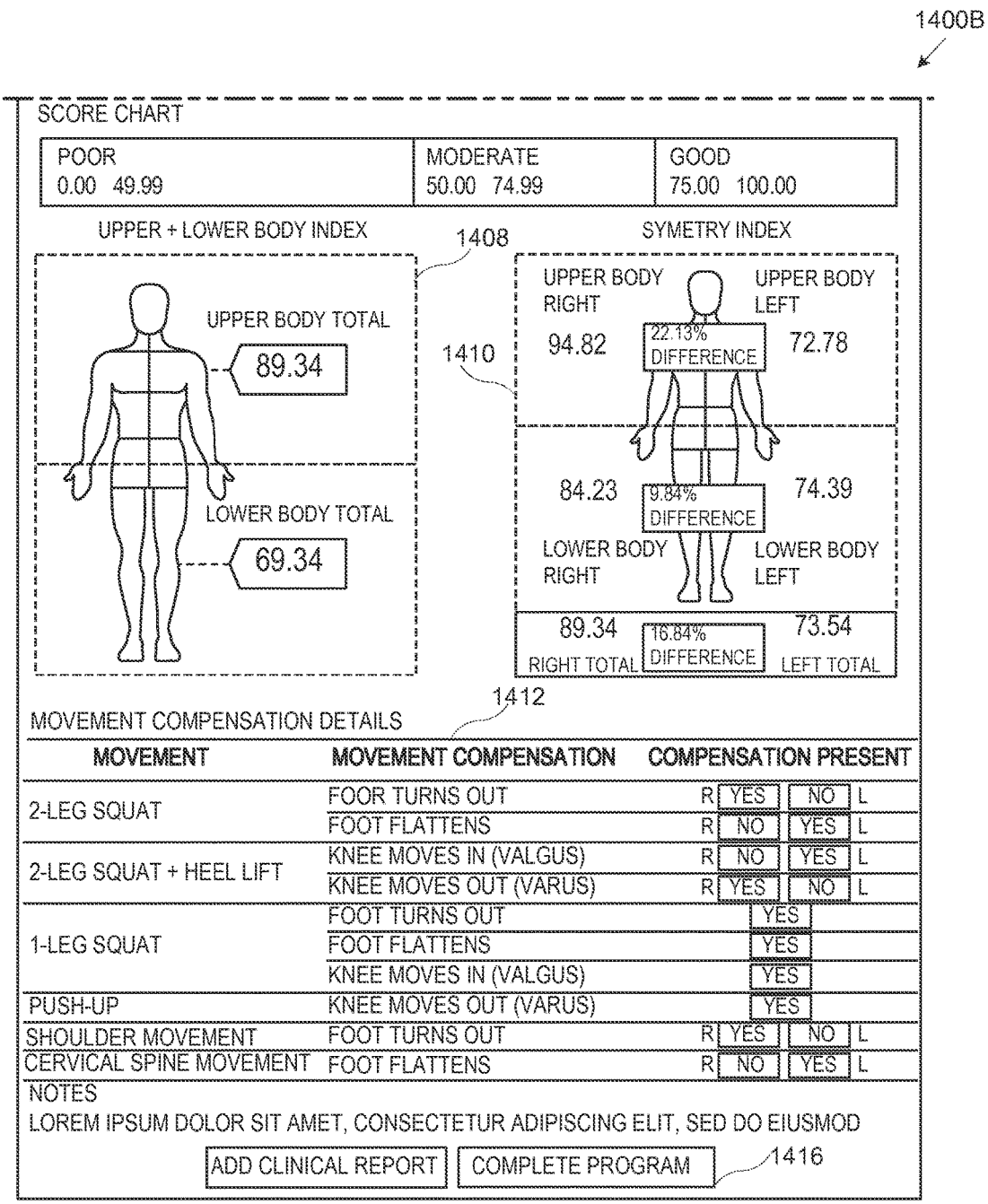
FIG. 14B: EXEMPLARY MOVEMENT EFFICIENCY TEST REPORT SCREENSHOT

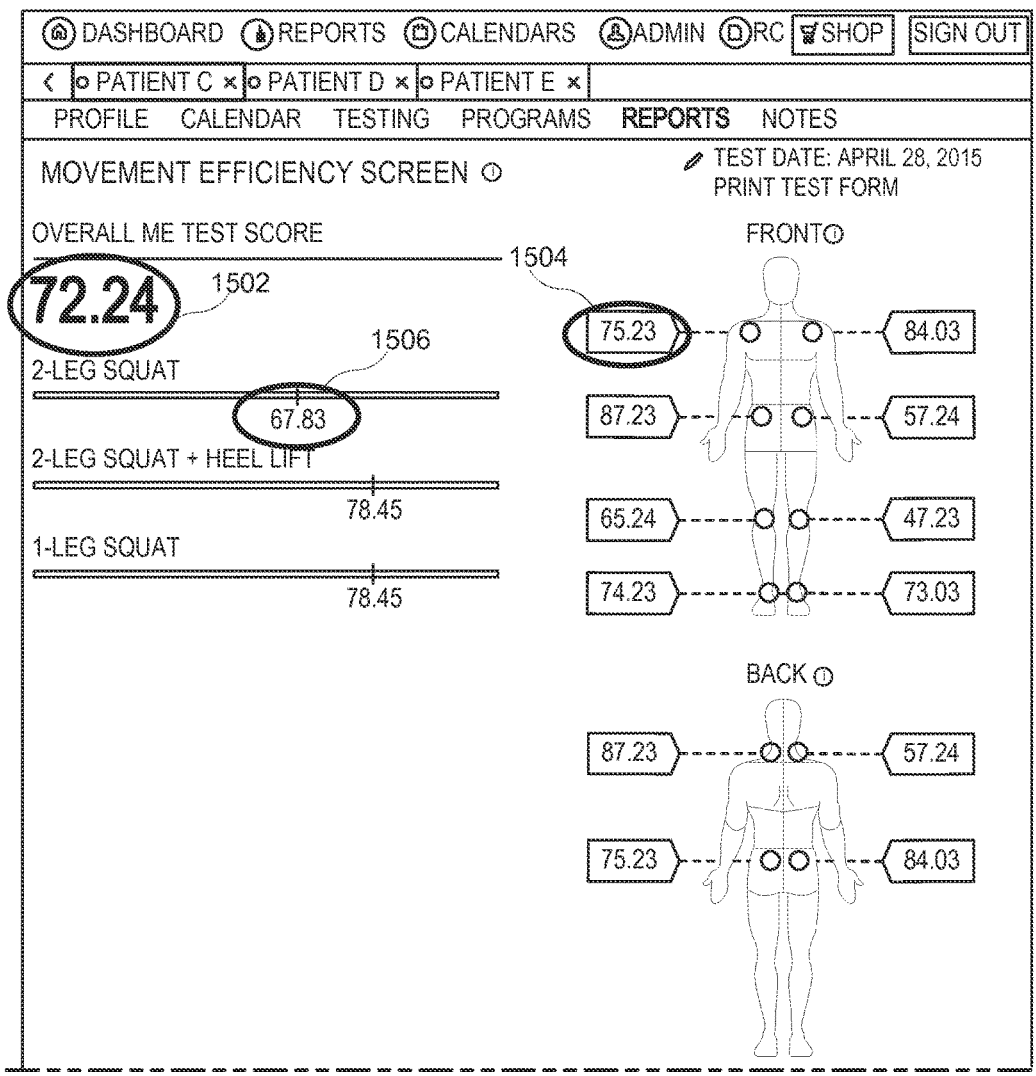
FIG. 15A: EXEMPLARY MOVEMENT EFFICIENCY SCREEN REPORT SCREENSHOT

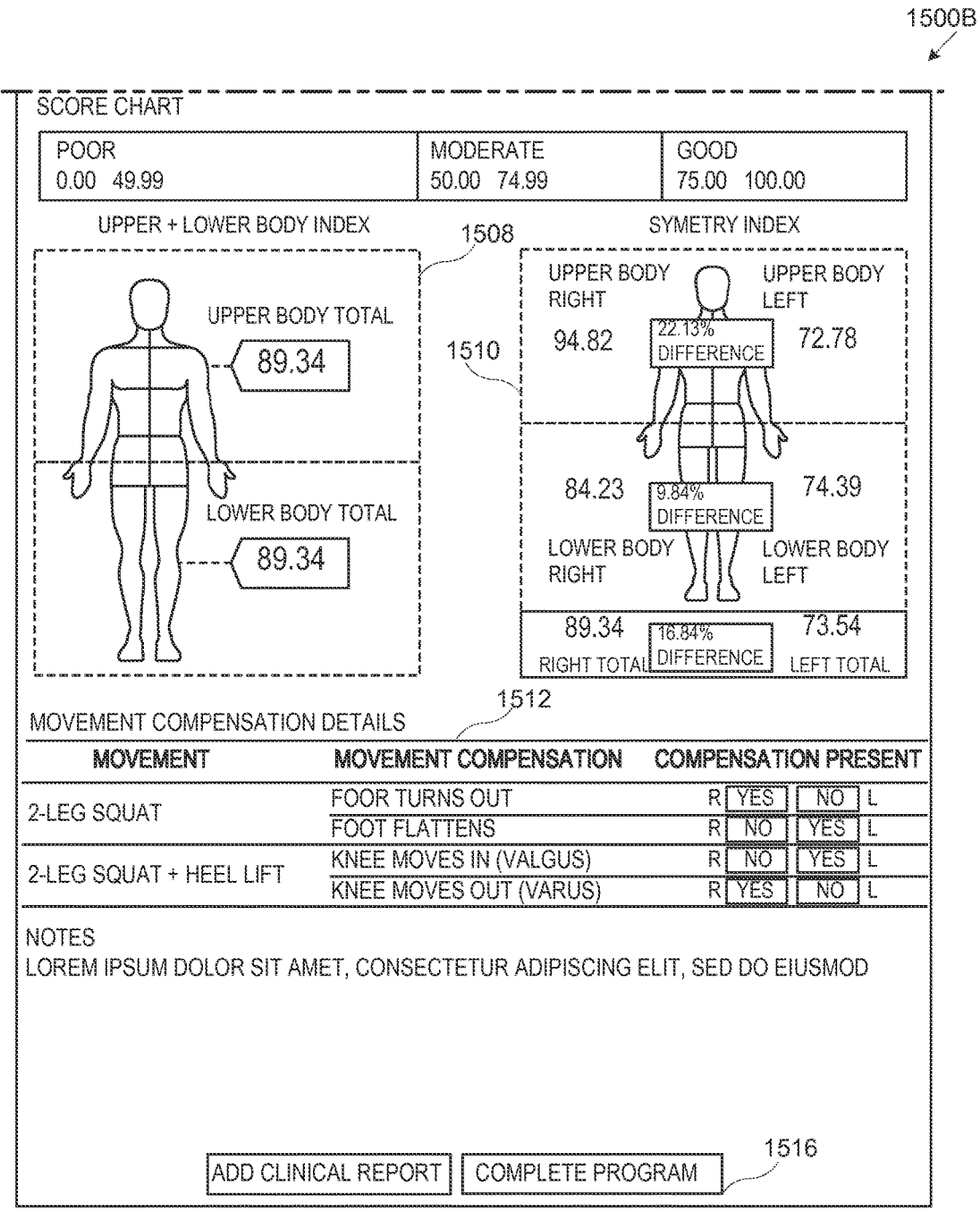
*FIG. 15B:* EXEMPLARY MOVEMENT EFFICIENCY SCREEN REPORT SCREENSHOT

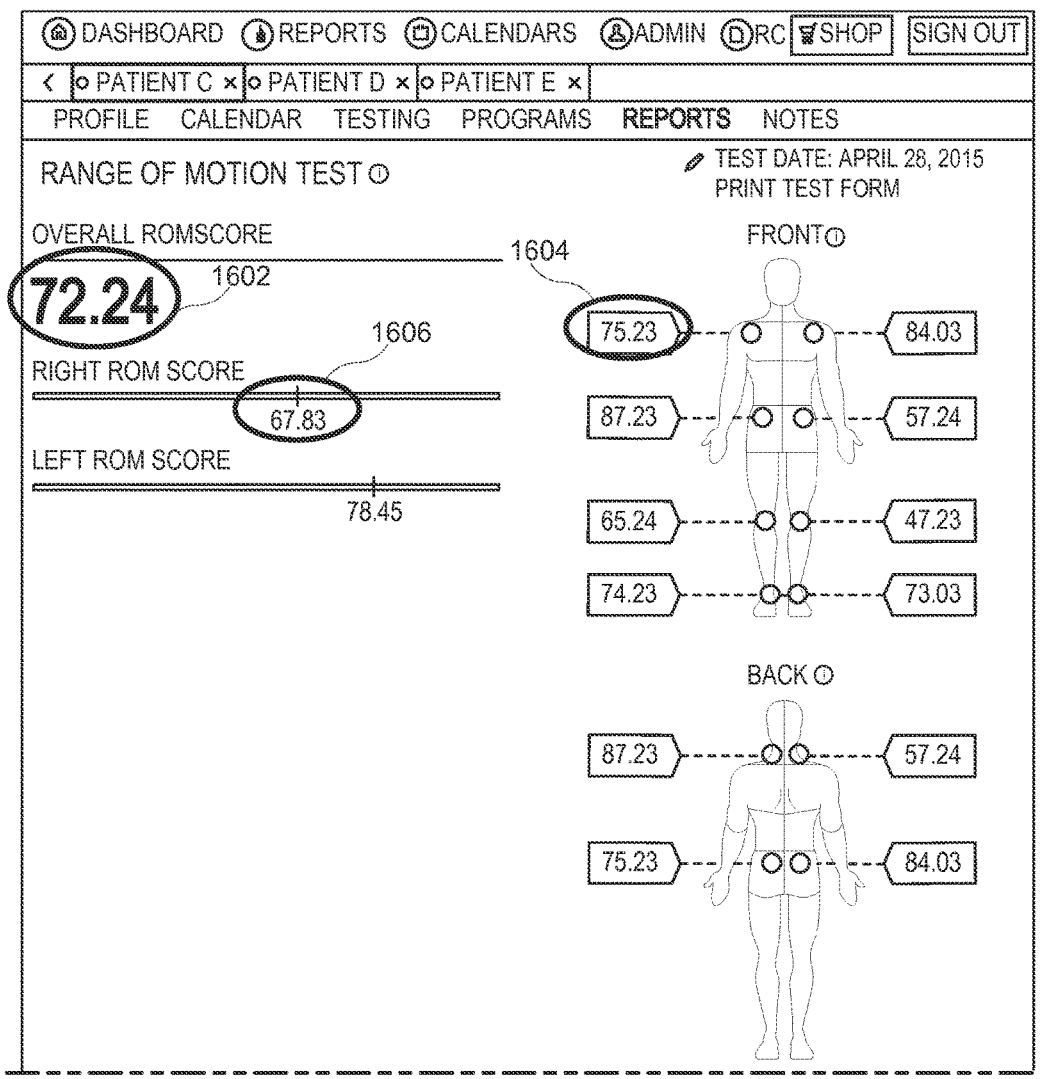
*FIG. 16A:* EXEMPLARY RANGE OF MOTION TEST REPORT SCREENSHOT

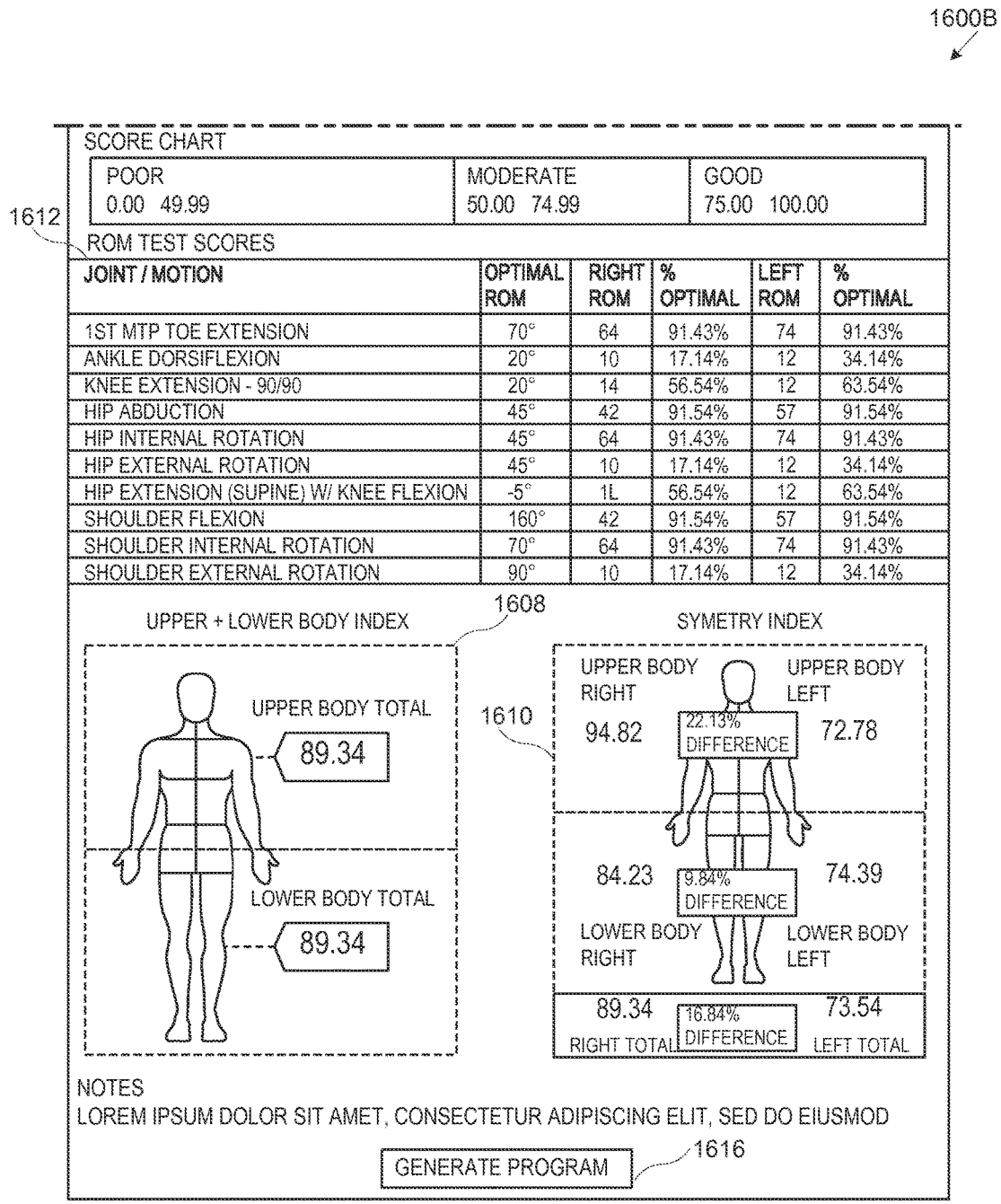
FIG. 16B: EXEMPLARY RANGE OF MOTION TEST REPORT SCREENSHOT

PERFORMANCE TEST RESULTS

TEST DATE: APRIL 28, 2015
PRINT TEST FORM

ANTHROPOMETRICS

| | |
|---|---|
| HEIGHT | 6"1 |
| WEIGHT | 167.54 lbs |
| BODY FAT | 12.00% |
| STANDING REACH | 9"1' |
| WINGSPAN | 8'5" |

HEIGHT 6' 2"
STANDING REACH 9' 1"
WINGSPAN 8' 5"

NOTES
LOREM IPSUM DOLOR SIT AMET, CONSECTETUR ADIPISCING ELIT, SED DO EIUSMOD

FUNCTIONAL MOVEMENT

| | |
|---|---|
| PRONE PLANK | 34.00 SEC |
| SIDE PLANK | |
|   RIGHT | 12.00% |
|   LEFT | 9T |
| CURL UP BEEP TEST | 32 REPS |
| MOVEMENT SCREEN | 74.54 |
| STAR EXCURSION BALANCE TEST | |
|   (ANT) RIGHT | 34.01 CM |
|   (ANT) LEFT | 32.01 CM |
|   DIFFERENCE | 2.00 CM |
|   (PM) RIGHT | 44.31 CM |
|   (PM) LEFT | 22.61 CM |
|   DIFFERENCE | 22.56 CM |
|   (PL) RIGHT | 34.01 CM |
|   (PL) LEFT | 32.01 CM |
|   DIFFERENCE | 2.00 CM |

POWER

| | |
|---|---|
| VERTICAL JUMP / STANDING | 34.00 SEC |
| VERTICAL JUMP / APPROACH | 12.00% |
| BROAD JUMP | 12 REPS |
| MB ROTATION THROW | |
|   RIGHT | 35'5" |
|   LEFT | 42'4" |

SPEED + AGILITY

| | |
|---|---|
| 30 YD DASH | 34.00 SEC |
| 40 YD DASH | 12.00% |
| PRO LANE AGILITY | 9T |
| 3/4 COURT SPRINT | 32 REPS |
| NBA LANE SHUTTLE | |
|   RIGHT | 34.01 SEC |
|   LEFT | 32.96 SEC |
| 5-10-5 (PRO AGILITY SHUTTLE) | 44.31 CM |
| SHARK SKILL TEST | |
|   RIGHT | 34.01 CM |
|   LEFT | 32.01 CM |

STRENGTH

| | |
|---|---|
| PUSH UP / TOTAL IN 1 MIN | 34.00 SEC |
| PUSH UP / TO FATIGUE | 12.00% |
| BENCH PRESS | |
|   REPS | 12 REPS |
|   WEIGHT | 225 LBS |
| GRIP STRENGTH | |
|   RIGHT | 275 LBS |
|   LEFT | 275 LBS |

*FIG. 17:* EXEMPLARY PERFORMANCE TEST REPORT SCREENSHOT

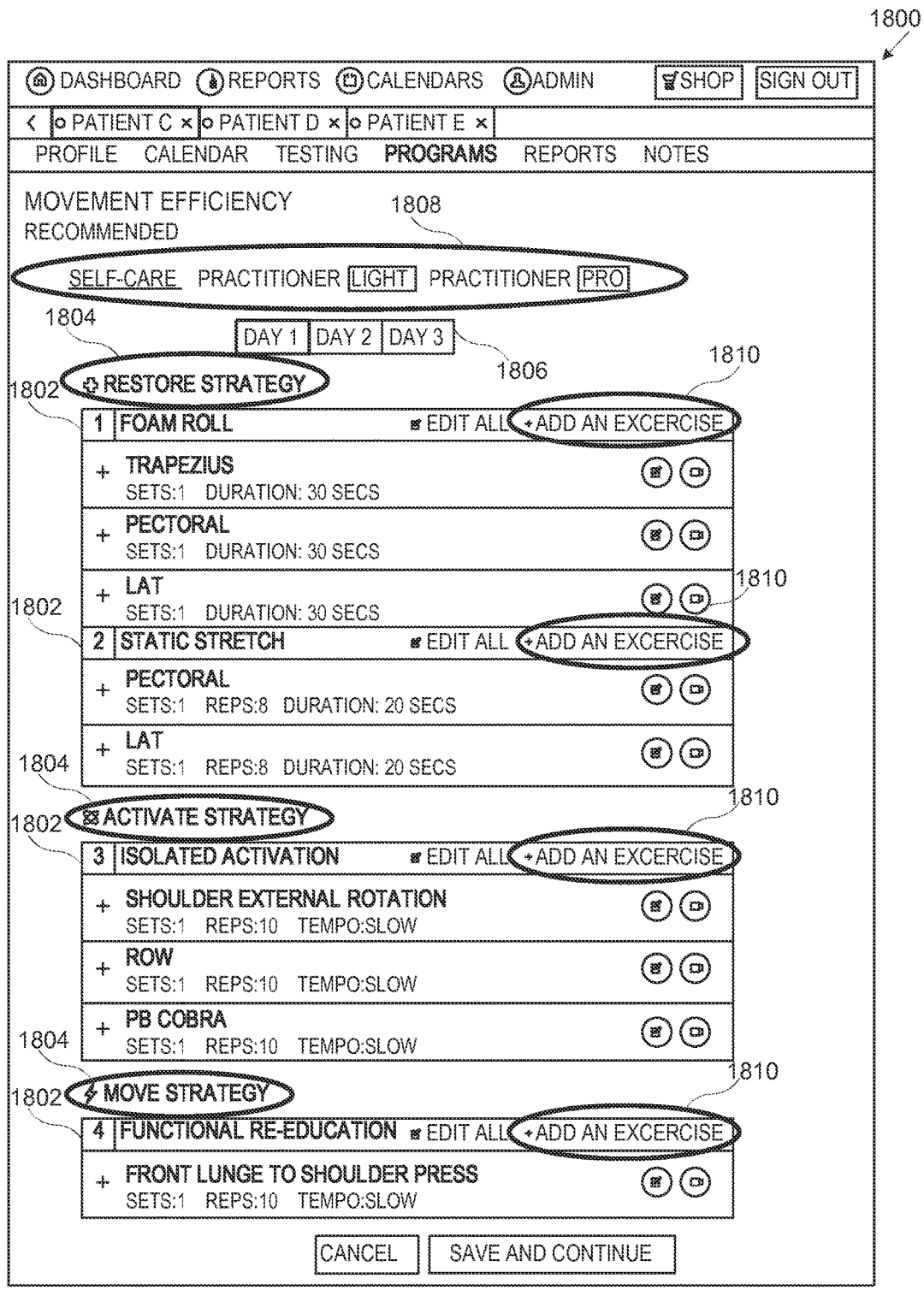
FIG. 18: EXEMPLARY PROGRAM GENERATION SCREENSHOT

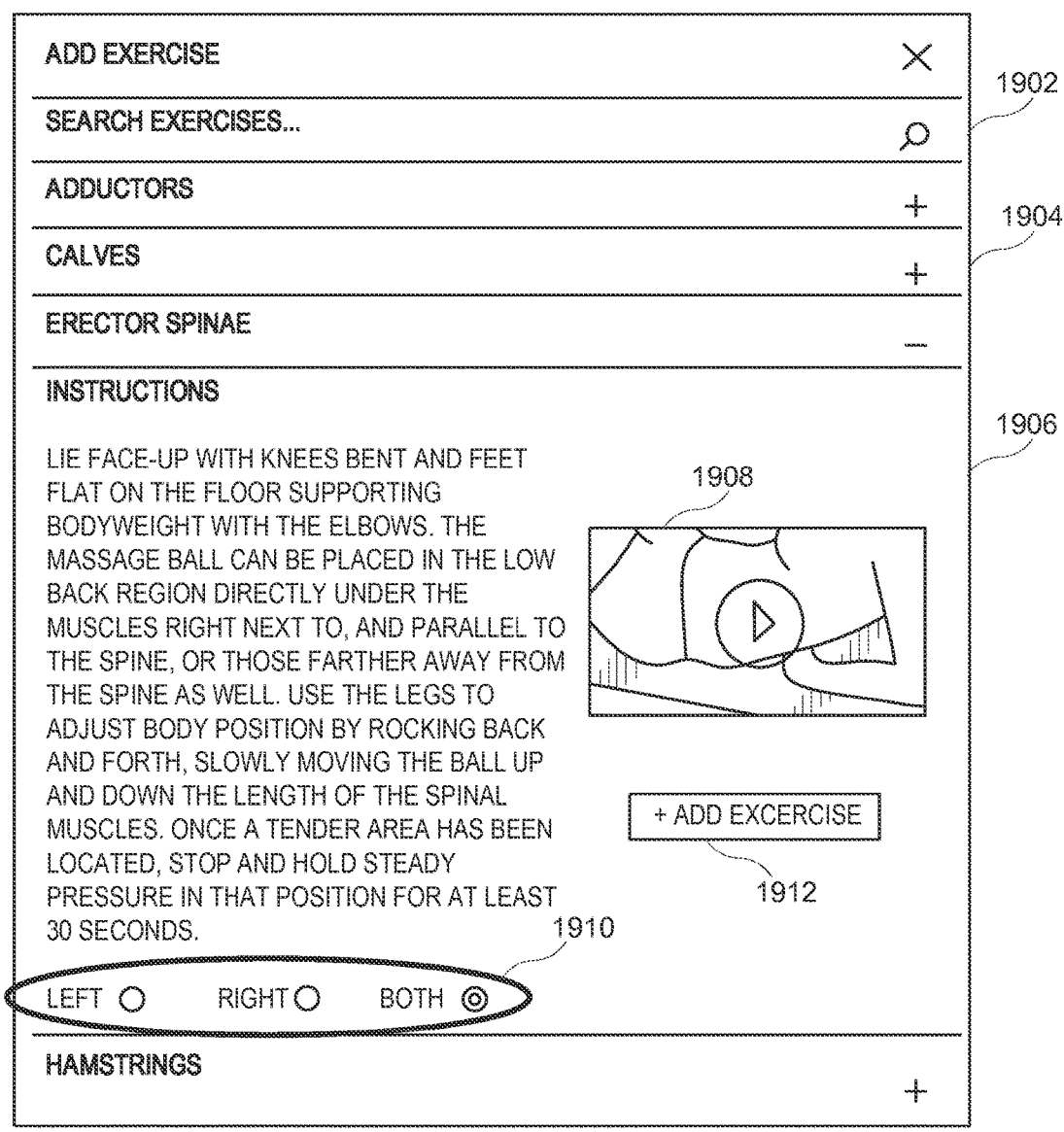
FIG. 19: EXEMPLARY PROGRAM MODIFICATION SCREENSHOT

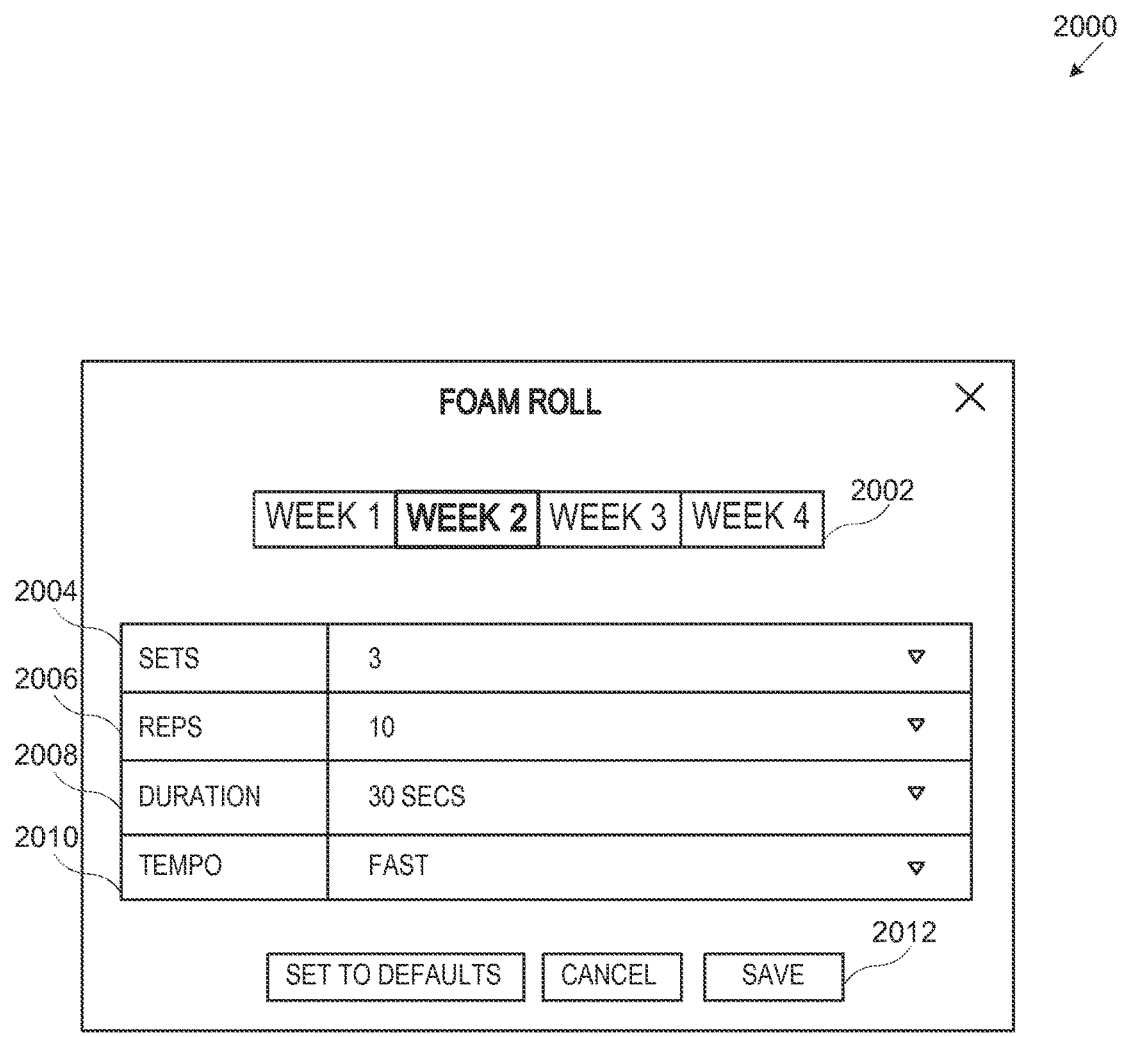
*FIG. 20:* EXEMPLARY EXERCISE MODIFICATION SCREENSHOT

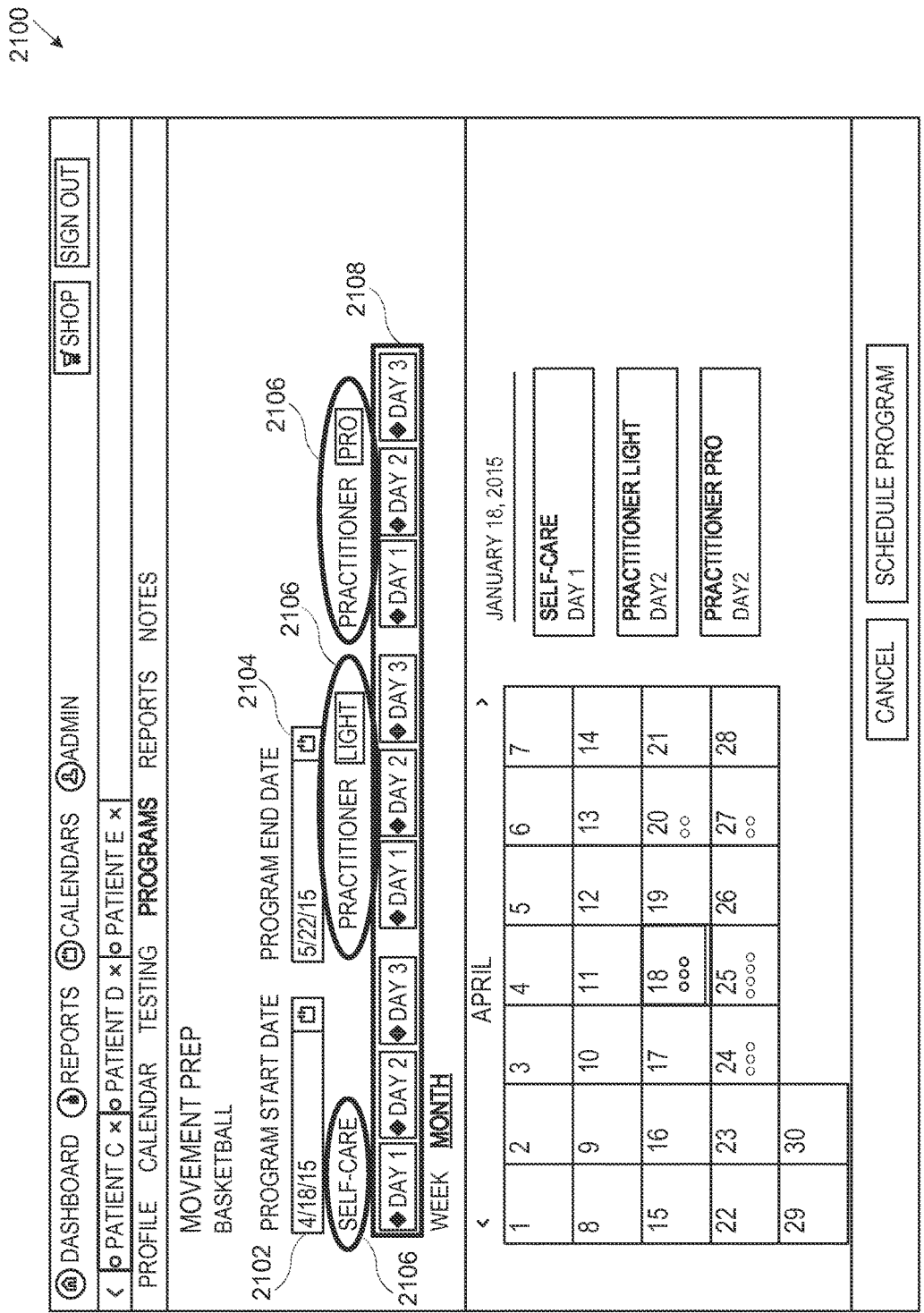
FIG. 21: EXEMPLARY PROGRAM SCHEDULING SCREENSHOT

FIG. 22: EXEMPLARY ALTERNATIVE PROGRAM SCHEDULING SCREENSHOT

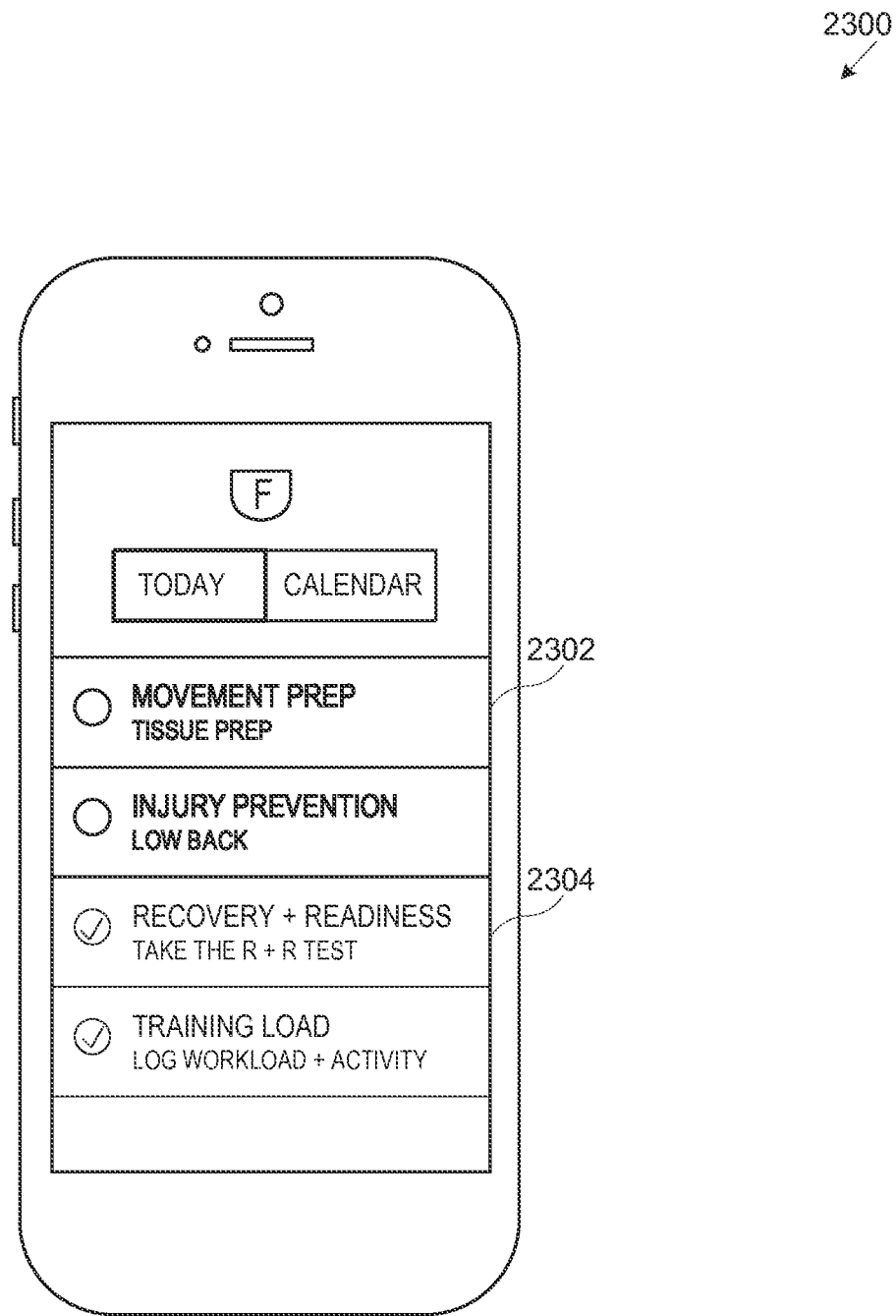
FIG. 23: EXEMPLARY PROGRAM SUMMARY SCREENSHOT

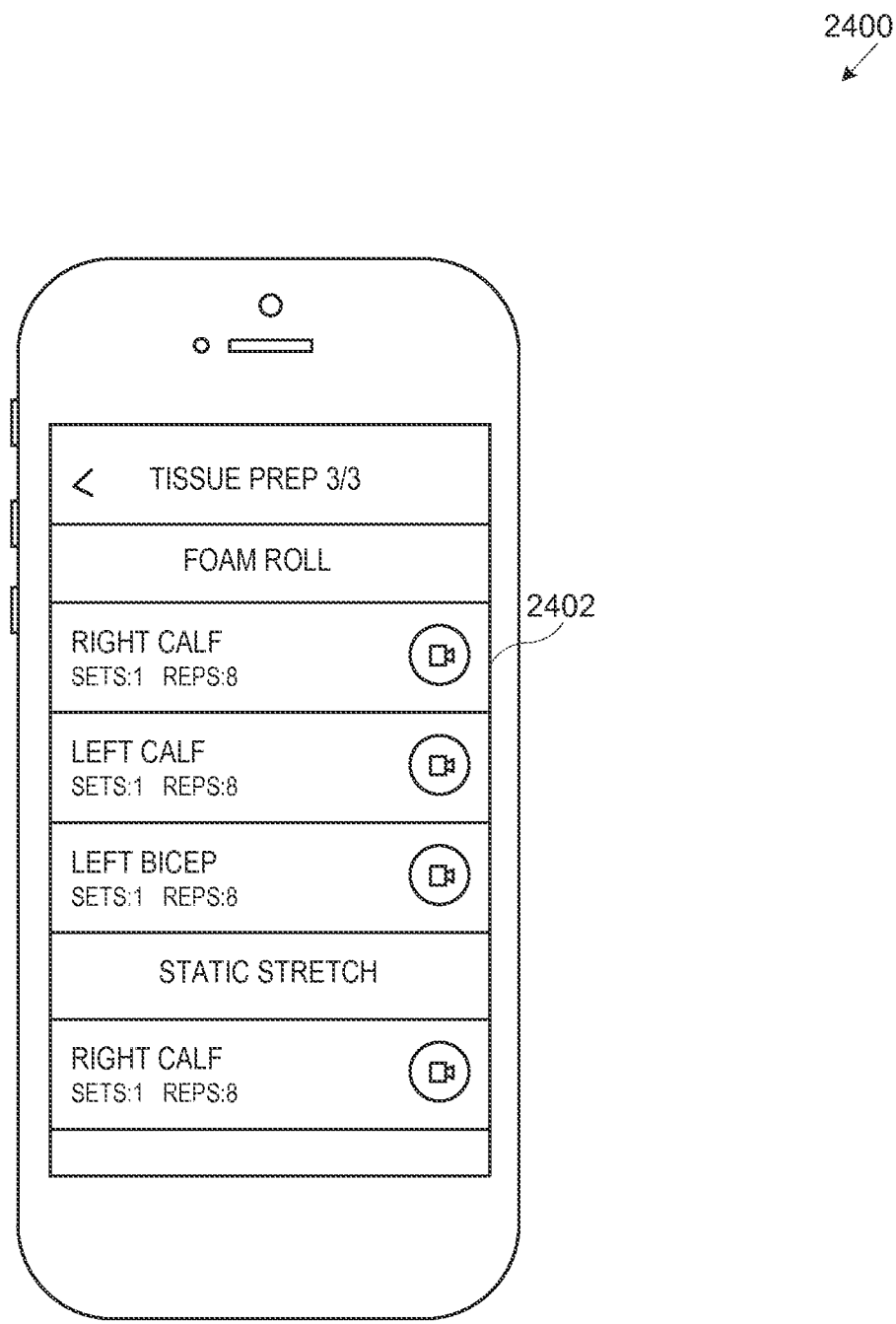
*FIG. 24:* EXEMPLARY EXERCISE LIST SCREENSHOT

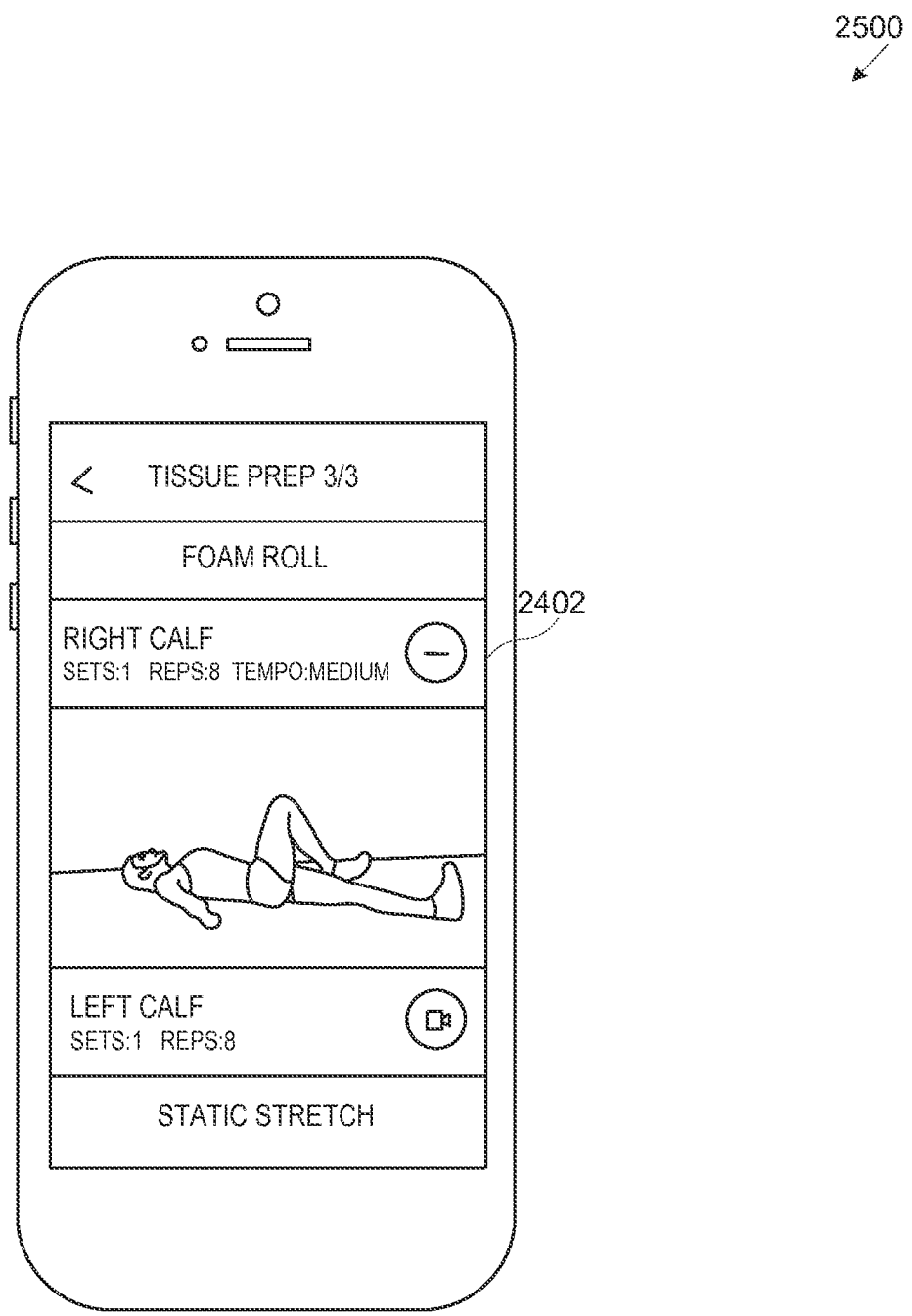
FIG. 25: EXEMPLARY EXERCISE LIST (DETAIL VIEW) SCREENSHOT

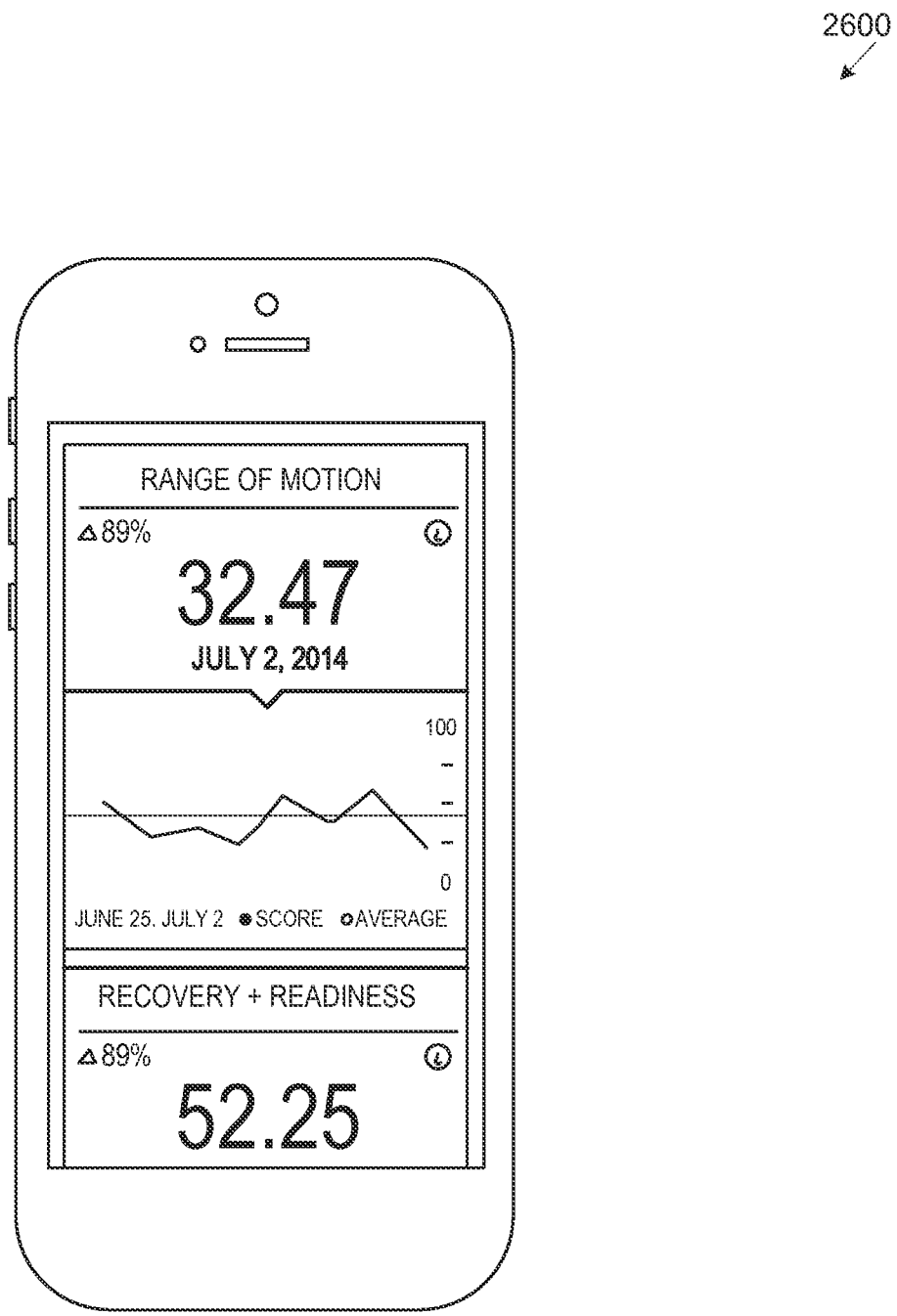
FIG. 26: EXEMPLARY TEST RESULT AND PROGRESS SUMMARY SCREENSHOT

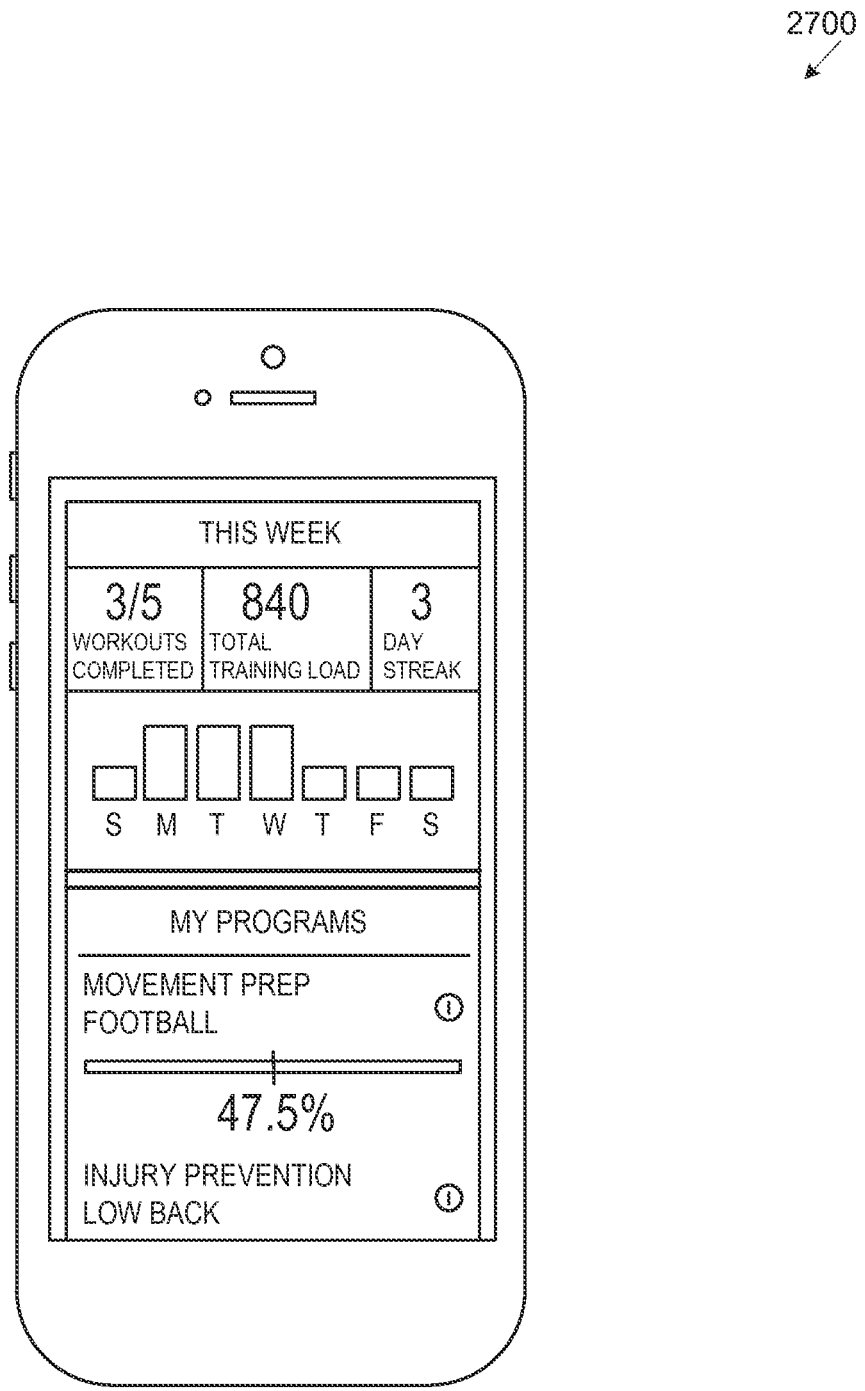
FIG. 27: EXEMPLARY WEEKLY PROGRESS SUMMARY SCREENSHOT

SYSTEMS AND METHODS FOR COMPENSATION ANALYSIS AND TARGETED, CORRECTIVE PROGRAM GENERATION

CROSS REFERENCE TO RELATED APPLICATIONS

This application claims priority to, the benefit under 35 U.S.C. § 119 of, and incorporates by reference herein in its entirety U.S. Provisional Patent Application No. 62/046,520, filed Sep. 5, 2014, and entitled "Systems and Methods for Assessing and Improving Physical Capability."

TECHNICAL FIELD

The present systems and methods relate generally to sports science, and more particularly to human performance and injury prevention. The present disclosure describes useful embodiments in medical, fitness, sport performance, education, home therapy, and vocational training environments, among others.

BACKGROUND

Human beings should move efficiently and effectively to avoid injury and enhance functional performance capacity and output. Current methods of assessing physical movement to prevent injury and optimize performance include measurements of an individual's ability to perform strength, flexibility, or endurance tests, but these methods are static tests performed by a third party in a highly subjective process that often lead to inconsistent and inaccurate results. Moreover, creation of training programs post-assessment often requires manual program development, which may not accurately achieve the desired results of improving movement efficiency and physical fitness to prevent injury and optimize performance.

Therefore, there is a long-felt but unresolved need for a system or method that generates targeted, corrective exercise programs based on a compensation analysis.

BRIEF SUMMARY OF THE DISCLOSURE

Briefly described, and according to one embodiment, aspects of the present disclosure generally relate to systems and methods for objectively assessing physical performance of a subject and generating programs specifically tailored to correct any physical deficiencies identified during that assessment. Generally, the assessments may be performed on subjects (e.g., patients, athletes, etc.) of any age, sex, or fitness level. Additionally, in various embodiments, the system may be implemented as a web-based software system that is used to record the results of an assessment or a perceptual computing system with accompanying sensor system (e.g., camera, etc.) that is used to automate the recording of the assessment. In various embodiments, the results of the assessment are then fed into an algorithm that determines a recommended exercise program to improve the physical capabilities of the subject over time.

In various embodiments, the subject may perform tasks as part of an assessment the results of which are recorded in binary (e.g., "yes" or "no") format. Generally, this assessment is referred to herein as the "movement efficiency test." In one embodiment, the subject performs several different tasks as part of the movement efficiency test (e.g., 2-leg squat, 2-leg squat with heel lift, 1-leg squat, push-up, shoulder movement, trunk/thoracic spine movement, cervical spine movement, etc.). Generally, while the subject is performing the tasks, an observer, such as a practitioner or a perceptual computing device, monitors the movements of the subject to collect data and determine whether any compensations are present. In various embodiments, "compensations" generally refer to physical deficiencies that result in an improper/potentially harmful movement of the body (e.g., the right gluteus medius is not strong, so the right knee moves inwardly during the 2-leg squat). If a compensation is present, then the observer indicates "yes" the compensation is present. If, however, a compensation is not present, then the observer indicates "no" the compensation is not present (or, in one embodiment, "no" is the default setting, so the observer does not provide any additional indication). As will occur to one having ordinary skill in the art, by recording results only in binary format, the assessment generally removes the subjectivity that could occur when recording results in non-binary format. For example, instead of a practitioner or subject being required to determine how much a knee rotates inwardly during a 2-leg squat (e.g., none, some, severe, etc.) and the distinctions between the categorizations (e.g., how much is some rotation versus severe rotation), the practitioner or subject may record the presence of the movement regardless of how slight or severe the movement may be (e.g., some knee rotation is recorded in the same manner as severe knee rotation). Thus, the system objectively identifies the subject's performance on the test.

In one embodiment, the "movement efficiency screen" comprises an abbreviated assessment for determining whether certain predefined compensations are present in the subject (e.g., wherein the subject performs the 2-leg squat, 2-leg squat with heel lift, 1-leg squat, etc.). Generally, the results of the movement efficiency screen are recorded in the same manner as those of the movement efficiency test (e.g., binary format). As will occur to one having ordinary skill in the art, the movement efficiency screen may be used to quickly identify certain particular compensations that a subject may present or to quickly check a subject's progress after following a recommended exercise program for a predetermined period of time.

The subject, in various embodiments, may also perform tasks as part of an assessment the results of which are not recorded in binary format. Generally, this assessment is referred to herein as the "range of motion test." In various embodiments, the "range of motion test" generally refers to an assessment of the range of motion that a subject possesses in a particular joint (e.g., hip) by measuring the range of motion (in degrees) in that particular joint for a particular movement (e.g., hip abduction). To conduct a range of motion test, a practitioner usually uses a goniometer to measure the range of the motion of the measured joints. In one embodiment, the range of motion of a particular joint is compared to an optimal range (e.g., as suggested by the American Academy of Orthopedic Surgeons) for that particular joint and movement and scored as a percentage of the optimal range. In another embodiment, the percentage of the optimal range is recorded by the system in binary format (e.g., "yes" the percentage is below a certain threshold or "no" it is not).

In various embodiments, as part of an assessment, the subject may perform a combination of tests for which results are recorded in binary format and tests for which results are not recorded in binary format (e.g., a movement efficiency screen and a range of motion test, etc.). Generally, by performing multiple tests as part of a single assessment, the system is able to collect additional data points regarding the subject and generate a more tailored recommended exercise program.

Based on the results of the assessment, in various embodiments, a recommended exercise program is generated that is tailored to the particular subject and designed to correct the compensations and other physical deficiencies identified by the assessment. Generally, the recommended exercise program is generated based on various algorithms that sort, prioritize, and correlate the physical deficiencies with exercises that target the muscle groups impacted by the deficiencies. In various embodiments, the recommended exercise programs comprise three different strategies: "restore," "activate," and "move." In one embodiment, the restore strategy should be performed before the activate strategy, which should be performed before the move strategy. Generally, the sequencing of the strategies combined with the specific exercise acute variable progressions (e.g., sets, repetitions, etc.) within each strategy provide specific physiological and physical outcomes that have been researched and proven to improve movement efficiency/quality of movement. In various embodiments, the restore strategy comprises exercises such as foam rolling and static stretching of particular muscles (e.g., foam rolling hamstring, etc.) that inhibit, lengthen, and improve mobility of soft-tissue and joints caused by over-performing muscles, the activate strategy comprises exercises such as isolated muscle activation exercises (e.g., should external rotation, etc.) that activate/strengthen under-performing muscles, and the move strategy comprises exercises such as dynamic exercises that require the use of various integrated muscles (e.g., front lunge to shoulder press, etc.) to reinforce the activation/strengthening and integrated functional re-education of the body.

Generally, the recommended exercise programs comprise a predetermined number of days (e.g., 3 or 5) of exercises that may be performed in different settings. In various embodiments, the predetermined number of days and different exercises in different settings may be generated at one time from the same data set (e.g., same input but different varied outputs) so that a practitioner and/or patient does not need to request additional exercises, settings, etc. In one embodiment, the settings comprise a self-care setting wherein the subject performs the exercises by himself/herself, a practitioner light setting wherein the subject performs the exercises with the assistance of a certified practitioner (e.g., strength and conditioning coach, personal trainer, etc.), and a practitioner pro setting wherein the subject performs the exercises with the assistance of a licensed practitioner (e.g., physical therapist, chiropractor, etc.). In various embodiments, these settings permit the recommended exercise program to be modified to better accommodate the subject and adhere to professional scope of practice guidelines. For example, if a particular subject is a professional athlete with a serious injury, then the particular subject may perform, as part of his/her recommended exercise program, only those exercises in the practitioner pro setting. In contrast, an amateur athlete with a minor injury may perform only those exercises in the self-care setting.

In various embodiments, a practitioner may modify both the assessment being performed (e.g., to better suit the needs of the subject or further investigate a perceived deficiency) and the recommended exercise program (e.g., to occur as part of a certain schedule or include exercises that the practitioner prefers). For example, the practitioner may decide that the subject would benefit from performing both a movement efficiency test and a range of motion test. Accordingly, the system will incorporate the results of both tests to determine the recommended exercise program. Additionally, the practitioner may decide that the subject should alternate between three days of self-care and three days of practitioner light exercises and schedule the recommended exercise program accordingly. Similarly, the practitioner may substitute a particular preferred exercise (e.g., pushups) for an exercise in the recommended exercise program (e.g., bench press) that the practitioner does not want the subject to perform.

In one embodiment, a method, comprising the steps of: receiving an electronic request at an electronic computing device for completion of a physical evaluation test relating to an athlete; retrieving a predefined template from a system database corresponding to the physical evaluation test, the predefined template comprising data relating to a plurality of physical movement tasks for performance by the athlete, each physical movement task comprising a particular static, transitional, or dynamic movement and being associated with one or more identifiable compensations, each identifiable compensation having only two possible outcomes comprising a first outcome indicative of the presence of the particular identifiable compensation during completion by the athlete of the respective physical movement task and a second outcome indicative of the absence of the particular identifiable compensation during completion by the athlete of the respective physical movement task, wherein the identifiable compensation is present when a particular body part of the athlete moves in a predefined manner, whereby the movement indicates that the athlete possesses a particular physical deficiency; displaying, via the electronic computing device, the plurality of physical movement tasks for performance by the athlete; receiving, for at least one of the plurality of physical movement tasks, a selection of either the first outcome or the second outcome of the particular identifiable compensation; and saving, via the electronic computing device, the received selection of either the first outcome or the second outcome of the particular identifiable compensation in the system database in association with an instance of the physical evaluation test and the respective physical movement task.

In one embodiment, a method, comprising the steps of: receiving an electronic request at an electronic computing device for completion of a physical evaluation test relating to a test subject; retrieving a predefined template from a system database corresponding to the physical evaluation test, the predefined template comprising data relating to a plurality of physical movement tasks for performance by the test subject, each physical movement task being associated with one or more identifiable compensations, each identifiable compensation having only two possible outcomes comprising a first outcome indicative of the presence of the particular identifiable compensation during completion by the test subject of the respective physical movement task and a second outcome indicative of the absence of the particular identifiable compensation during completion by the test subject of the respective physical movement task; displaying, via the electronic computing device, the plurality of physical movement tasks for performance by the test subject; receiving, for at least one of the plurality of physical movement tasks, a selection of either the first outcome or the second outcome of the particular identifiable compensation; and saving, via the electronic computing device, the received selection of either the first outcome or the second outcome of the particular identifiable compensation in the system database in association with an instance of the physical evaluation test and the respective physical movement task.

In one embodiment, a system, comprising: an electronic computing device; a database having stored therein one or more predefined templates corresponding to one or more physical evaluation tests; and a processor operatively connected with the electronic computing device and the database, the processor operative to: receive an electronic request from the electronic computing device for completion of a particular physical evaluation test relating to a test subject; retrieve a particular predefined template from the database corresponding to the particular physical evaluation test, the particular predefined template comprising data relating to a plurality of physical movement tasks for performance by the test subject, each physical movement task being associated with one or more identifiable compensations, each identifiable compensation having only two possible outcomes comprising a first outcome indicative of the presence of the particular identifiable compensation during completion by the test subject of the respective physical movement task and a second outcome indicative of the absence of the particular identifiable compensation during completion by the test subject of the respective physical movement task; display, via the electronic computing device, the plurality of physical movement tasks for performance by the test subject; receive, for at least one of the plurality of physical movement tasks, a selection of either the first outcome or the second outcome of the particular identifiable compensation; and save, in the database, the received selection of either the first outcome or the second outcome of the particular identifiable compensation in the system database in association with an instance of the particular physical evaluation test and the respective physical movement task.

In one embodiment, a method, comprising the steps of: receiving an electronic request at an electronic computing device for completion of a physical evaluation test relating to a test subject; retrieving a predefined template from a system database corresponding to the physical evaluation test, the predefined template comprising data relating to a plurality of physical movement tasks for performance by the test subject, each physical movement task being associated with one or more identifiable compensations, each identifiable compensation having only two possible outcomes comprising a first outcome indicative of the presence of the particular identifiable compensation during completion by the test subject of the respective physical movement task and a second outcome indicative of the absence of the particular identifiable compensation during completion by the test subject of the respective physical movement task; displaying, via the electronic computing device, the plurality of physical movement tasks for performance by the test subject; recording, via a sensor, performance data corresponding to the performance by the test subject of at least one of the plurality of physical movement tasks; identifying, from the performance data, either the first outcome or the second outcome of the particular identifiable compensation; and saving the identified first outcome or second outcome of the particular identifiable compensation in the system database in association with an instance of the physical evaluation test and the respective physical movement task.

In one embodiment, a method, comprising the steps of: receiving an electronic request at an electronic computing device for generation of an exercise program customized for an athlete; retrieving, from a system database, electronic data corresponding to prior completion by the athlete of a physical evaluation test, the electronic data comprising compensation data indicating the presence of one or more physical compensations of the athlete; determining one or more physical exercises designed to improve the one or more physical compensations of the athlete by comparing the compensation data indicating the presence of the one or more physical compensations of the athlete with one or more predefined rules defining a plurality of physical exercises and one or more body parts targeted by the plurality of physical exercises; sorting the one or more exercises into exercise groups, wherein a particular exercise group comprises one or more particular exercises that target a particular body part associated with a particular physical compensation; scheduling at least one exercise from each exercise group, based on one or more predefined criteria, in a predefined order; and generating an exercise program for completion by the athlete, the exercise program comprising the at least one exercise from each exercise group in the predefined order.

In one embodiment, a method, comprising the steps of: receiving an electronic request at an electronic computing device for generation of an exercise program customized for a test subject; retrieving, from a system database, electronic data corresponding to prior completion by the test subject of a physical evaluation test, the electronic data comprising compensation data indicating the presence of one or more physical compensations of the test subject; determining one or more physical exercises designed to improve the one or more physical compensations of the test subject by comparing the compensation data indicating the presence of the one or more physical compensations of the test subject with one or more predefined rules defining a plurality of physical exercises; and generating an exercise program for completion by the test subject, the exercise program comprising the one or more physical exercises.

In one embodiment, a system, comprising: an electronic computing device; a database having stored therein electronic data corresponding to prior completion by a test subject of a physical evaluation test; and a processor operatively connected with the electronic computing device and the database, the processor operative to: receive an electronic request from the electronic computing device for generation of an exercise program customized for the test subject; retrieve, from the database, the electronic data corresponding to prior completion by the test subject of the physical evaluation test, the electronic data comprising compensation data indicating the presence of one or more physical compensations of the test subject; determine one or more physical exercises designed to improve the one or more physical compensations of the test subject by comparing the compensation data indicating the presence of the one or more physical compensations of the test subject with one or more predefined rules defining a plurality of physical exercises; and generate an exercise program for completion by the test subject, the exercise program comprising the one or more physical exercises.

In one embodiment, a method, comprising the steps of: receiving an electronic request at an electronic computing device for generation of one or more exercise programs customized for an athlete; retrieving, from a system database, electronic data corresponding to prior completion by the athlete of a physical evaluation test; determining at least two exercise settings corresponding to the athlete; determining, for the first exercise setting, a first set of physical exercises designed to improve physical performance of the athlete by comparing the electronic data with one or more predefined rules defining a plurality of physical exercises corresponding to the first setting and one or more body parts targeted by the plurality of physical exercises corresponding to the first setting; determining, for the second exercise setting, a second set of physical exercises designed to improve physical performance of the athlete by comparing the electronic data with one or more predefined rules defining a plurality of physical exercises corresponding to the second setting and one or more body parts targeted by the plurality of physical exercises corresponding to the second setting; sorting the first set of physical exercises into a first set of exercise groups and sorting the second set of physical exercises into a second set of exercise groups, wherein a particular exercise group comprises one or more particular exercises that target a particular body part associated with a particular physical compensation; scheduling at least one exercise from each exercise group in the first set of exercise groups, based on one or more predefined criteria corresponding to the first setting, in a predefined order corresponding to the first setting; scheduling at least one exercise from each exercise group in the second set of exercise groups, based on one or more predefined criteria corresponding to the second setting, in a predefined order corresponding to the second setting; and generating at least two exercise programs for completion by the athlete, a first exercise program comprising the at least one exercise from each exercise group in the first set of exercise groups in the predefined order corresponding to the first setting, and a second exercise program comprising the at least one exercise from each exercise group in the second set of exercise groups in the predefined order corresponding to the second setting.

In one embodiment, a method, comprising the steps of: receiving an electronic request at an electronic computing device for generation of one or more exercise programs customized for a test subject; retrieving, from a system database, electronic data corresponding to prior completion by the test subject of a physical evaluation test; determining at least two exercise settings corresponding to the test subject; determining, for the first exercise setting, a first set of physical exercises designed to improve physical performance of the test subject by comparing the electronic data with one or more predefined rules defining a plurality of physical exercises corresponding to the first setting; determining, for the second exercise setting, a second set of physical exercises designed to improve physical performance of the test subject by comparing the electronic data with one or more predefined rules defining a plurality of physical exercises corresponding to the second setting; and generating at least two exercise programs for completion by the test subject, a first exercise program comprising the first set of exercises and a second exercise program comprising the second set of exercises.

In one embodiment, a system, comprising: an electronic computing device; a database having stored therein electronic data corresponding to prior completion by a test subject of a physical evaluation test; and a processor operatively connected with the electronic computing device and the database, the processor operative to: receive an electronic request from the electronic computing device for generation of one or more exercise programs customized for a test subject; retrieve, from the database, the electronic data corresponding to prior completion by the test subject of a physical evaluation test; determine at least two exercise settings corresponding to the test subject; determine, for the first exercise setting, a first set of physical exercises designed to improve physical performance of the test subject by comparing the electronic data with one or more predefined rules defining a plurality of physical exercises corresponding to the first setting; determine, for the second exercise setting, a second set of physical exercises designed to improve physical performance of the test subject by comparing the electronic data with one or more predefined rules defining a plurality of physical exercises corresponding to the second setting; and generate at least two exercise programs for completion by the test subject, a first exercise program comprising the first set of exercises and a second exercise program comprising the second set of exercises.

According to one aspect of the present disclosure, the method, further comprising the steps of: determining, based on the predefined template, whether selections of either the first outcome or the second outcome have been received for all of the one or more identifiable compensations relating to the respective physical movement task; upon determination that one or more selections have not been received for one or more particular identifiable compensations, requesting, via the electronic computing device, selection of either the first outcome or the second outcome for the one or more particular identifiable compensations; receiving a selection of either the first outcome or the second outcome for the one or more particular identifiable compensations; and saving, via the electronic computing device, the received selection of either the first outcome or the second outcome for the one or more particular identifiable compensations in the system database in association with an instance of the physical evaluation test and the respective physical movement task. Furthermore, the method, further comprising the steps of: determining, based on the predefined template, whether each of the plurality of physical movement tasks has been performed by the athlete; upon determination that one or more particular physical movement tasks have not been performed by the athlete, displaying, via the electronic computing device, the one or more particular physical movement tasks for performance by the athlete; receiving, for the one or more particular physical movement tasks, a selection of either the first outcome or the second outcome of the particular identifiable compensation; and saving, via the electronic computing device, the received selection of either the first outcome or the second outcome of the particular identifiable compensation in the system database in association with an instance of the physical evaluation test and the respective physical movement task. Moreover, the method, wherein the electronic computing device comprises a perceptual computing device. Further, the method, wherein the receiving step further comprises receiving, from the perceptual computing device, electronic data for at least one of the plurality of physical movement tasks, and determining, based on the electronic data, a selection of either the first outcome or the second outcome of the particular identifiable compensation. Additionally, the method, wherein the receiving step further comprises: recording, via a perceptual computing device, performance data corresponding to a performance by the athlete of the at least one of the plurality of physical movement tasks; determining, via the perceptual computing device, whether the first outcome or the second outcome of the particular identifiable compensation corresponds to the performance data; and selecting, based upon determining whether the first outcome or the second outcome of the particular identifiable compensation corresponds to the performance data, either the first outcome or the second outcome of the particular identifiable compensation. Also, the method, further comprising the step of generating, based on the received selections, at least one exercise program for the athlete.

According to one aspect of the present disclosure, the method, further comprising the steps of: determining, based on the predefined template, whether each of the plurality of physical movement tasks has been performed by the test subject; upon determination that one or more particular physical movement tasks have not been performed by the test subject, displaying, via the electronic computing device, the one or more particular physical movement tasks for performance by the test subject; receiving, for the one or more particular physical movement tasks, a selection of either the first outcome or the second outcome of the particular identifiable compensation; and saving, via the electronic computing device, the received selection of either the first outcome or the second outcome of the particular identifiable compensation in the system database in association with an instance of the physical evaluation test and the respective physical movement task. Furthermore, the method, wherein the physical movement task comprises a particular transitional movement. Moreover, the method, wherein the physical movement task comprises a particular dynamic movement. Further, the method, wherein the physical movement task comprises a measurement of a range of motion of a particular joint of the test subject. Additionally, the method, wherein the physical movement task comprises a particular static movement. Also, the method, wherein the identifiable compensation is present when a particular body part of the test subject moves in a predefined manner, whereby the movement indicates that the test subject possesses a particular physical deficiency. Furthermore, the method, wherein the receiving step further comprises: recording, via a perceptual computing device, a performance by the test subject of the at least one of the plurality of physical movement tasks; determining, via the perceptual computing device, whether the first outcome or the second outcome of the particular identifiable compensation corresponds to the performance by the test subject of the at least one of the plurality of physical movement tasks; and selecting, based upon determining whether the first outcome or the second outcome of the particular identifiable compensation corresponds to the performance, either the first outcome or the second outcome of the particular identifiable compensation. Moreover, the method, further comprising the step of generating, based on the received selections, at least one exercise program for the test subject.

According to one aspect of the present disclosure, the system, wherein the processor is further operative to: determine, based on the particular predefined template, whether selections of either the first outcome or the second outcome have been received for all of the one or more identifiable compensations from the respective physical movement task; upon determination that one or more selections have not been received for one or more particular identifiable compensations, request, via the electronic computing device, selection of either the first outcome or the second outcome for the one or more particular identifiable compensations; receive a selection of either the first outcome or the second outcome for the one or more particular identifiable compensations; and save, in the database, the received selection of either the first outcome or the second outcome for the one or more particular identifiable compensations in the system database in association with an instance of the particular physical evaluation test and the respective physical movement task. Further, the system, wherein the processor is further operative to: determine, based on the particular predefined template, whether each of the plurality of physical movement tasks has been performed by the test subject; upon determination that one or more particular physical movement tasks have not been performed by the test subject, display, via the electronic computing device, the one or more particular physical movement tasks for performance by the test subject; receive, for the one or more particular physical movement tasks, a selection of either the first outcome or the second outcome of the particular identifiable compensation; and save, in the database, the received selection of either the first outcome or the second outcome of the particular identifiable compensation in the system database in association with an instance of the particular physical evaluation test and the respective physical movement task.

According to one aspect of the present disclosure, the system, wherein the particular physical evaluation test comprises a first particular physical evaluation test, the particular predefined template comprises a first predefined template, and the processor is further operative to: receive an electronic request from the electronic computing device for completion of a second particular physical evaluation test relating to the test subject; retrieve a second particular predefined template from the database corresponding to the second particular physical evaluation test, the second particular predefined template comprising data relating to a plurality of physical movement tasks for performance by the test subject, each physical movement task having one or more identifiable compensations, each identifiable compensation having only two possible outcomes comprising a first outcome indicative of the presence of the particular identifiable compensation during successful completion by the test subject of the respective physical movement task and a second outcome indicative of the absence of the particular identifiable compensation during successful completion by the test subject of the respective physical movement task; display, via the electronic computing device, the plurality of physical movement tasks for performance by the test subject; receive, for at least one of the plurality of physical movement tasks, a selection of either the first outcome or the second outcome of the particular identifiable compensation; and save, in the database, the received selection of either the first outcome or the second outcome of the particular identifiable compensation in the system database in association with an instance of the second particular physical evaluation test and the respective physical movement task. Also, the system, wherein the physical movement task is selected from the group comprising a particular static movement, a particular transitional movement, a particular dynamic movement, or a measurement of a range of motion of a particular joint of the test subject. Furthermore, the system, wherein the identifiable compensation is present when a particular body part of the test subject moves in a predefined manner, whereby the movement indicates that the test subject possesses a particular physical deficiency. Moreover, the system, further comprising a perceptual computing device operatively connected with the processor, the processor further operative to: record, via the perceptual computing device, a performance by the test subject of the at least one of the plurality of physical movement tasks; determine, via the perceptual computing device, whether the first outcome or the second outcome of the particular identifiable compensation corresponds to the performance by the test subject of the at least one of the plurality of physical movement tasks; and select, based upon determining whether the first outcome or the second outcome of the particular identifiable compensation corresponds to the performance, either the first outcome or the second outcome of the particular identifiable compensation. Further, the system, wherein the processor is further operative to generate, based on the received selections, at least one exercise program for the test subject.

According to one aspect of the present disclosure, the method, wherein the sensor is selected from the group comprising a video camera, a motion-sensing camera, or a perceptual computing device.

According to one aspect of the present disclosure, the method, wherein the generating step further comprises the steps of: receiving, via the electronic computing device, one or more modifications to the exercise program; and modifying the exercise program based on the one or more modifications to the exercise program. Additionally, the method, wherein the one or more predefined criteria define one or more interactions between the at least one exercises from each exercise group, the one or more interactions impacting an efficacy of the at least one exercises from each exercise group to improve the one or more physical compensations of the athlete. Also, the method, wherein the one or more predefined criteria define one or more relationships between the one or more physical compensations, the one or more relationships prioritizing the one or more physical compensations. Furthermore, the method, wherein the one or more predefined criteria define one or more associations between the at least one exercises from each exercise group and the one or more physical compensations. Moreover, the method, wherein the electronic data further corresponds to prior completion by the athlete of one or more additional physical evaluation tests. Further, the method, wherein the compensation data comprises only two possible values corresponding to a first outcome indicative of the presence of a particular compensation of the athlete and a second outcome indicative of the absence of a particular compensation of the athlete.

According to one aspect of the present disclosure, the method, wherein the generating step further comprises the steps of: sorting the one or more exercises into exercise groups, wherein a particular exercise group comprises one or more particular exercises that target a particular body part associated with a particular physical compensation; and scheduling at least one exercise from each exercise group, based on one or more predefined criteria, in a predefined order. Additionally, the method, wherein the one or more predefined criteria define one or more interactions between the at least one exercises from each exercise group, the one or more interactions impacting an efficacy of the at least one exercises from each exercise group to improve the one or more physical compensations of the test subject. Also, the method, wherein the electronic data further corresponds to prior completion by the test subject of one or more additional physical evaluation tests. Furthermore, the method, wherein the one or more predefined rules defining a plurality of physical exercises further define one or more body parts targeted by the plurality of physical exercises. Moreover, the method, wherein the compensation data comprises only two possible values corresponding to a first outcome indicative of the presence of a particular compensation of the test subject and a second outcome indicative of the absence of a particular compensation of the test subject.

According to one aspect of the present disclosure, the system, wherein the processor is further operative, as part of the generation of the exercise program, to: sort the one or more exercises into exercise groups, wherein a particular exercise group comprises one or more particular exercises that target a particular body part associated with a particular physical compensation; and schedule at least one exercise from each exercise group, based on one or more predefined criteria, in a predefined order. Further, the system, wherein the processor is further operative, as part of the generation of the exercise program, to: receive, from the electronic computing device, one or more modifications to the exercise program; and modify the exercise program based on the one or more modifications to the exercise program. Additionally, the system, wherein the one or more predefined criteria define one or more interactions between the at least one exercises from each exercise group, the one or more interactions impacting an efficacy of the at least one exercises from each exercise group to improve the one or more physical compensations of the test subject. Also, the system, wherein the one or more predefined criteria define one or more relationships between the one or more physical compensations, the one or more relationships prioritizing the one or more physical compensations. Furthermore, the system, wherein the one or more predefined criteria define one or more associations between the at least one exercises from each exercise group and the one or more physical compensations. Moreover, the system, wherein the electronic data further corresponds to prior completion by the test subject of one or more additional physical evaluation tests. Further, the system, wherein the one or more predefined rules defining a plurality of physical exercises further define one or more body parts targeted by the plurality of physical exercises.

According to one aspect of the present disclosure, the method, wherein the generating step further comprises the steps of: receiving, via the electronic computing device, one or more modifications to at least one of the exercise programs; and modifying the at least one exercise program based on the one or more modifications to the exercise program. Additionally, the method, wherein the one or more predefined criteria corresponding to the first setting define one or more interactions between the at least one exercises from each exercise group in the first set of exercise groups, the one or more interactions impacting an efficacy of the at least one exercises from each exercise group in the first set of exercise groups to improve the one or more physical compensations of the athlete, and the one or more predefined criteria corresponding to the second setting define one or more interactions between the at least one exercises from each exercise group in the second set of exercise groups, the one or more interactions impacting an efficacy of the at least one exercises from each exercise group in the second set of exercise groups to improve the one or more physical compensations of the athlete. Also, the method, wherein the one or more predefined criteria corresponding to the first setting and the second setting define one or more relationships between the one or more physical compensations, the one or more relationships prioritizing the one or more physical compensations. Furthermore, the method, wherein the one or more predefined criteria corresponding to the first setting define one or more associations between the at least one exercises from each exercise group in the first set of exercise groups and the one or more physical compensations, and the one or more predefined criteria corresponding to the second setting define one or more associations between the at least one exercises from each exercise group in the second set of exercise groups and the one or more physical compensations. Moreover, the method, wherein the electronic data further corresponds to prior completion by the athlete of one or more additional physical evaluation tests. According to one aspect of the present disclosure, the method, wherein the generating step further comprises the steps of: sorting the first set of physical exercises into a first set of exercise groups and sorting the second set of physical exercises into a second set of exercise groups, wherein a particular exercise group comprises one or more particular exercises that target a particular body part associated with a particular physical compensation; scheduling at least one exercise from each exercise group in the first set of exercise groups, based on one or more predefined criteria corresponding to the first setting, in a predefined order corresponding to the first setting, in the first exercise program; and scheduling at least one exercise from each exercise group in the second set of exercise groups, based on one or more predefined criteria corresponding to the second setting, in a predefined order corresponding to the second setting, in the second exercise program. Further, the method, wherein the one or more predefined criteria corresponding to the first setting define one or more interactions between the at least one exercises from each exercise group in the first set of exercise groups, the one or more interactions impacting an efficacy of the at least one exercises from each exercise group in the first set of exercise groups to improve the one or more physical compensations of the test subject, and the one or more predefined criteria corresponding to the second setting define one or more interactions between the at least one exercises from each exercise group in the second set of exercise groups, the one or more interactions impacting an efficacy of the at least one exercises from each exercise group in the second set of exercise groups to improve the one or more physical compensations of the test subject. Additionally, the method, wherein the electronic data further corresponds to prior completion by the test subject of one or more additional physical evaluation tests. Also, the method, wherein the one or more predefined rules defining a plurality of physical exercises corresponding to the first setting and the second setting further define one or more body parts targeted by the plurality of physical exercises.

According to one aspect of the present disclosure, the system, wherein the processor is further operative, as part of the generation of the exercise program, to: sort the first set of physical exercises into a first set of exercise groups and sort the second set of physical exercises into a second set of exercise groups, wherein a particular exercise group comprises one or more particular exercises that target a particular body part associated with a particular physical compensation; schedule at least one exercise from each exercise group in the first set of exercise groups, based on one or more predefined criteria corresponding to the first setting, in a predefined order corresponding to the first setting, in the first exercise program; and schedule at least one exercise from each exercise group in the second set of exercise groups, based on one or more predefined criteria corresponding to the second setting, in a predefined order corresponding to the second setting, in the second exercise program.

According to one aspect of the present disclosure, the system, wherein the processor is further operative, as part of the generation of the exercise program, to: receive, via the electronic computing device, one or more modifications to at least one of the exercise programs; and modify the at least one exercise program based on the one or more modifications to the exercise program. Moreover, the system, wherein the one or more predefined criteria corresponding to the first setting define one or more interactions between the at least one exercises from each exercise group in the first set of exercise groups, the one or more interactions impacting an efficacy of the at least one exercises from each exercise group in the first set of exercise groups to improve the one or more physical compensations of the test subject, and the one or more predefined criteria corresponding to the second setting define one or more interactions between the at least one exercises from each exercise group in the second set of exercise groups, the one or more interactions impacting an efficacy of the at least one exercises from each exercise group in the second set of exercise groups to improve the one or more physical compensations of the test subject. Further, the system, wherein the one or more predefined criteria corresponding to the first setting and the second setting define one or more relationships between the one or more physical compensations, the one or more relationships prioritizing the one or more physical compensations. Additionally, the system, wherein the one or more predefined criteria corresponding to the first setting define one or more associations between the at least one exercises from each exercise group in the first set of exercise groups and the one or more physical compensations, and the one or more predefined criteria corresponding to the second setting define one or more associations between the at least one exercises from each exercise group in the second set of exercise groups and the one or more physical compensations. Also, the system, wherein the electronic data further corresponds to prior completion by the test subject of one or more additional physical evaluation tests. Furthermore, the system, wherein the one or more predefined rules defining a plurality of physical exercises corresponding to the first setting and the second setting further define one or more body parts targeted by the plurality of physical exercises.

These and other aspects, features, and benefits of the claimed invention(s) will become apparent from the following detailed written description of the preferred embodiments and aspects taken in conjunction with the following drawings, although variations and modifications thereto may be effected without departing from the spirit and scope of the novel concepts of the disclosure.

BRIEF DESCRIPTION OF THE DRAWINGS

The accompanying drawings illustrate one or more embodiments and/or aspects of the disclosure and, together with the written description, serve to explain the principles of the disclosure. Wherever possible, the same reference numbers are used throughout the drawings to refer to the same or like elements of an embodiment, and wherein:

FIG. 1 illustrates an exemplary, high-level overview of one embodiment of the disclosed compensation analysis and program generation system.

FIG. 2 illustrates an exemplary architecture of one embodiment of the disclosed compensation analysis and program generation system.

FIG. 3 is a flowchart showing a summary of an exemplary, high-level process flow, according to one embodiment of the present disclosure.

FIG. 4 is a flowchart showing an exemplary test performance and data collection process, according to one embodiment of the present disclosure.

FIG. 5 is a flowchart showing an exemplary test data analysis and score calculation process, according to one embodiment of the present disclosure.

FIG. 6 is a flowchart showing an exemplary program generation process, according to one embodiment of the present disclosure.

FIG. 7 is a screenshot of an exemplary subject roster screen of a compensation analysis and program generation system, according to one embodiment of the present disclosure.

FIG. 8 is a screenshot of an exemplary subject roster screen, in list view, of a compensation analysis and program generation system, according to one embodiment of the present disclosure.

FIG. 9 is a screenshot of an exemplary subject summary screen of a compensation analysis and program generation system, according to one embodiment of the present disclosure.

FIG. 10 is a screenshot of an exemplary test-selection screen of a compensation analysis and program generation system, according to one embodiment of the present disclosure.

FIG. 11 is a screenshot of an exemplary movement efficiency test performance and data collection screen of a compensation analysis and program generation system, according to one embodiment of the present disclosure.

FIG. 12 is a screenshot of an exemplary movement efficiency screen performance and data collection screen of a compensation analysis and program generation system, according to one embodiment of the present disclosure.

FIG. 13 is a screenshot of an exemplary range of motion test performance and data collection screen of a compensation analysis and program generation system, according to one embodiment of the present disclosure.

FIG. 14 (consisting of FIGS. 14A and 14B) is a screenshot of an exemplary movement efficiency test report screen of a compensation analysis and program generation system, according to one embodiment of the present disclosure.

FIG. 15 (consisting of FIGS. 15A and 15B) is a screenshot of an exemplary movement efficiency screen report screen of a compensation analysis and program generation system, according to one embodiment of the present disclosure.

FIG. 16 (consisting of FIGS. 16A and 16B) is a screenshot of an exemplary range of motion test report screen of a compensation analysis and program generation system, according to one embodiment of the present disclosure.

FIG. 17 is a screenshot of an exemplary performance test report screen of a compensation analysis and program generation system, according to one embodiment of the present disclosure.

FIG. 18 is a screenshot of an exemplary program generation screen of a compensation analysis and program generation system, according to one embodiment of the present disclosure.

FIG. 19 is a screenshot of an exemplary program modification screen of a compensation analysis and program generation system, according to one embodiment of the present disclosure.

FIG. 20 is a screenshot of an exemplary exercise modification screen of a compensation analysis and program generation system, according to one embodiment of the present disclosure.

FIG. 21 is a screenshot of an exemplary program scheduling screen, in monthly view, of a compensation analysis and program generation system, according to one embodiment of the present disclosure.

FIG. 22 is a screenshot of an alternative, exemplary program scheduling screen, in weekly view, of a compensation analysis and program generation system, according to one embodiment of the present disclosure.

FIG. 23 is a screenshot of an exemplary program summary screen, as displayed in a mobile application, of a compensation analysis and program generation system, according to one embodiment of the present disclosure.

FIG. 24 is a screenshot of an exemplary exercise list screen, as displayed in a mobile application, of a compensation analysis and program generation system, according to one embodiment of the present disclosure.

FIG. 25 is a screenshot of an exemplary exercise list screen, in detail view as displayed in a mobile application, of a compensation analysis and program generation system, according to one embodiment of the present disclosure.

FIG. 26 is a screenshot of an exemplary test result and progress summary screen, as displayed in a mobile application, of a compensation analysis and program generation system, according to one embodiment of the present disclosure.

FIG. 27 is a screenshot of an exemplary weekly progress summary screen, as displayed in a mobile application, of a compensation analysis and program generation system, according to one embodiment of the present disclosure.

DETAILED DESCRIPTION

Overview

For the purpose of promoting an understanding of the principles of the present disclosure, reference will now be made to the embodiments illustrated in the drawings and specific language will be used to describe the same. It will, nevertheless, be understood that no limitation of the scope of the disclosure is thereby intended; any alterations and further modifications of the described or illustrated embodiments, and any further applications of the principles of the disclosure as illustrated therein are contemplated as would normally occur to one skilled in the art to which the disclosure relates. All limitations of scope should be determined in accordance with and as expressed in the claims.

Whether a term is capitalized is not considered definitive or limiting of the meaning of a term. As used in this document, a capitalized term shall have the same meaning as an uncapitalized term, unless the context of the usage specifically indicates that a more restrictive meaning for the capitalized term is intended. However, the capitalization or lack thereof within the remainder of this document is not intended to be necessarily limiting unless the context clearly indicates that such limitation is intended.

Aspects of the present disclosure generally relate to systems and methods for objectively assessing physical performance of a subject and generating programs specifically tailored to correct any physical deficiencies identified during that assessment. Generally, the assessments may be performed on subjects (e.g., patients, athletes, etc.) of any age, sex, or fitness level. Additionally, in various embodiments, the system may be implemented as a web-based software system that is used to record the results of an assessment or a perceptual computing system with accompanying sensor system (e.g., camera, etc.) that is used to automate the recording of the assessment. In various embodiments, the results of the assessment are then fed into an algorithm that determines a recommended exercise program to improve the physical capabilities of the subject over time.

In various embodiments, the subject may perform tasks as part of an assessment the results of which are recorded in binary (e.g., "yes" or "no") format. Generally, this assessment is referred to herein as the "movement efficiency test." In one embodiment, the subject performs several different tasks as part of the movement efficiency test (e.g., 2-leg squat, 2-leg squat with heel lift, 1-leg squat, push-up, shoulder movement, trunk/thoracic spine movement, cervical spine movement, etc.). Generally, while the subject is performing the tasks, an observer, such as a practitioner or a perceptual computing device, monitors the movements of the subject to collect data and determine whether any compensations are present. In various embodiments, "compensations" generally refer to physical deficiencies that result in an improper/potentially harmful movement of the body (e.g., the right gluteus medius is not strong, so the right knee moves inwardly during the 2-leg squat). If a compensation is present, then the observer indicates "yes" the compensation is present. If, however, a compensation is not present, then the observer indicates "no" the compensation is not present (or, in one embodiment, "no" is the default setting, so the observer does not provide any additional indication). As will occur to one having ordinary skill in the art, by recording results only in binary format, the assessment generally removes the subjectivity that could occur when recording results in non-binary format. For example, instead of a practitioner or subject being required to determine how much a knee rotates inwardly during a 2-leg squat (e.g., none, some, severe, etc.) and the distinctions between the categorizations (e.g., how much is some rotation versus severe rotation), the practitioner or subject may record the presence of the movement regardless of how slight or severe the movement may be (e.g., some knee rotation is recorded in the same manner as severe knee rotation). Thus, the system objectively identifies the subject's performance on the test.

In one embodiment, the "movement efficiency screen" comprises an abbreviated assessment for determining whether certain predefined compensations are present in the subject (e.g., wherein the subject performs the 2-leg squat, 2-leg squat with heel lift, 1-leg squat, etc.). Generally, the results of the movement efficiency screen are recorded in the same manner as those of the movement efficiency test (e.g., binary format). As will occur to one having ordinary skill in the art, the movement efficiency screen may be used to quickly identify certain particular compensations that a subject may present or to quickly check a subject's progress after following a recommended exercise program for a predetermined period of time.

The subject, in various embodiments, may also perform tasks as part of an assessment the results of which are not recorded in binary format. Generally, this assessment is referred to herein as the "range of motion test." In various embodiments, the "range of motion test" generally refers to an assessment of the range of motion that a subject possesses in a particular joint (e.g., hip) by measuring the range of motion (in degrees) in that particular joint for a particular movement (e.g., hip abduction). To conduct a range of motion test, a practitioner usually uses a goniometer to measure the range of the motion of the measured joints. In one embodiment, the range of motion of a particular joint is compared to an optimal range (e.g., as suggested by the American Academy of Orthopedic Surgeons) for that particular joint and movement and scored as a percentage of the optimal range. In another embodiment, the percentage of the optimal range is recorded by the system in binary format (e.g., "yes" the percentage is below a certain threshold or "no" it is not).

In various embodiments, as part of an assessment, the subject may perform a combination of tests for which results are recorded in binary format and tests for which results are not recorded in binary format (e.g., a movement efficiency screen and a range of motion test, etc.). Generally, by performing multiple tests as part of a single assessment, the system is able to collect additional data points regarding the subject and generate a more tailored recommended exercise program.

Based on the results of the assessment, in various embodiments, a recommended exercise program is generated that is tailored to the particular subject and designed to correct the compensations and other physical deficiencies identified by the assessment. Generally, the recommended exercise program is generated based on various algorithms that sort, prioritize, and correlate the physical deficiencies with exercises that target the muscle groups impacted by the deficiencies. In various embodiments, the recommended exercise programs comprise three different strategies: "restore," "activate," and "move." In one embodiment, the restore strategy should be performed before the activate strategy, which should be performed before the move strategy. Generally, the sequencing of the strategies combined with the specific exercise acute variable progressions (e.g., sets, repetitions, etc.) within each strategy provide specific physiological and physical outcomes that have been researched and proven to improve movement efficiency/quality of movement. In various embodiments, the restore strategy comprises exercises such as foam rolling and static stretching of particular muscles (e.g., foam rolling hamstring, etc.) that inhibit, lengthen, and improve mobility of soft-tissue and joints caused by over-performing muscles, the activate strategy comprises exercises such as isolated muscle activation exercises (e.g., should external rotation, etc.) that activate/strengthen under-performing muscles, and the move strategy comprises exercises such as dynamic exercises that require the use of various integrated muscles (e.g., front lunge to shoulder press, etc.) to reinforce the activation/strengthening and integrated functional re-education of the body.

Generally, the recommended exercise programs comprise a predetermined number of days (e.g., 3 or 5) of exercises that may be performed in different settings. In various embodiments, the predetermined number of days and different exercises in different settings may be generated at one time from the same data set (e.g., same input but different varied outputs) so that a practitioner and/or patient does not need to request additional exercises, settings, etc. In one embodiment, the settings comprise a self-care setting wherein the subject performs the exercises by himself/herself, a practitioner light setting wherein the subject performs the exercises with the assistance of a certified practitioner (e.g., strength and conditioning coach, personal trainer, etc.), and a practitioner pro setting wherein the subject performs the exercises with the assistance of a licensed practitioner (e.g., physical therapist, chiropractor, etc.). In various embodiments, these settings permit the recommended exercise program to be modified to better accommodate the subject and adhere to professional scope of practice guidelines. For example, if a particular subject is a professional athlete with a serious injury, then the particular subject may perform, as part of his/her recommended exercise program, only those exercises in the practitioner pro setting. In contrast, an amateur athlete with a minor injury may perform only those exercises in the self-care setting.

In various embodiments, a practitioner may modify both the assessment being performed (e.g., to better suit the needs of the subject or further investigate a perceived deficiency) and the recommended exercise program (e.g., to occur as part of a certain schedule or include exercises that the practitioner prefers). For example, the practitioner may decide that the subject would benefit from performing both a movement efficiency test and a range of motion test. Accordingly, the system will incorporate the results of both tests to determine the recommended exercise program. Additionally, the practitioner may decide that the subject should alternate between three days of self-care and three days of practitioner light exercises and schedule the recommended exercise program accordingly. Similarly, the practitioner may substitute a particular preferred exercise (e.g., pushups) for an exercise in the recommended exercise program (e.g., bench press) that the practitioner does not want the subject to perform.

Exemplary Embodiments

Referring now to the figures, for the purposes of example and explanation of the fundamental processes and components of the disclosed systems and methods, reference is made to FIG. 1, which illustrates an exemplary, high-level overview 100 of one embodiment of the disclosed compensation analysis and program generation system 102. As will be understood and appreciated, the exemplary, high-level overview 100 shown in FIG. 1 represents merely one approach or embodiment of the present system, and other aspects are used according to various embodiments of the present system.

Generally, by way of example, and not by way of limitation, a high-level overview 100 of actions involved in an exemplary compensation analysis and program generation process is shown in FIG. 1 with the help of a sequence of numbered steps indicated as steps "1" through "5," which are annotated as circled numbers. As shown in the overview 100, the compensation analysis and program generation process generally commences, at step 1, with a subject 101 determining that his/her physical performance is not sufficient to meet his/her goals. For example, the subject 101 may feel pain in a particular area (e.g., knee, shoulder, etc.), may not be performing as well as desired (e.g., consistently placing third in competition, not reaching certain performance levels, etc.), or may generally want to maintain a certain level of physical performance (e.g., not get injured, etc.). In various embodiments, a "subject" may be any human being that is the subject of compensation analysis and program generation according to the present disclosure, regardless of age, sex, or fitness level (e.g., professional athlete, amateur athlete, outdoor enthusiast, armchair quarterback, adult, child, patient, etc.). After determining that his/her physical performance is not sufficient, a subject 101 will then proceed to request and receive a movement analysis at step 2.

In various embodiments, compensation analysis (alternatively referred to herein as the "movement analysis" or "test performance and data collection process" or "test data analysis and score calculation process," the details of which will be explained in connection with the descriptions of FIGS. 3-5) begins at step 2 when a subject 101 performs a particular assessment test. In various embodiments, "assessment test" generally refers to a particular set of predefined tasks (e.g., body movements) that a subject performs, which is designed to identify various physical weaknesses of the subject. Generally, depending on the subject 101's condition, goals, etc., the particular assessment test (e.g., movement efficiency test, movement efficiency screen, range of motion test, performance test, etc.) may vary. In one embodiment, a particular assessment test comprises various pre-described tasks (e.g., 2-leg squat, 2-leg squat with heel lift, push-up, etc.) that the subject 101 performs to determine whether certain compensations are present. In various embodiments, "compensations" generally refer to physical deficiencies that result in an improper/potentially harmful movement of the body (e.g., the right gluteus medius is not strong, so the right knee moves inwardly during the 2-leg squat). If the subject 101 performs a task improperly (e.g., the wrong task, with the wrong form, in a manner that obscures a data collection device's ability to observe compensations, etc.), then the data collection device will prompt the subject 101 with a corrective action so that the task is performed properly. Details of the assessment tests and tasks will be better understood in association with the description of FIGS. 3, 4, and 10-17.

Still referring to FIG. 1, in one embodiment, the subject 101 may perform the particular assessment test in association with various data collection devices. For example, a subject 101 may perform the particular assessment test in front of a practitioner 103 who has been trained in accordance with the present disclosure (e.g., doctor, nurse, physical therapist, etc.). Generally, when the subject 101 is performing the assessment test in front of a registered practitioner 103, the registered practitioner 103 will visually observe the subject 101's performance, provide corrective actions if necessary, and record observed compensations into the disclosed system. Additionally, the subject 101 may perform the particular assessment test in association with a perceptual computing device 105 (e.g., any device, body sensors, combination of the same, etc. capable of capturing movement in an automated way, examples include a MICROSOFT® KINECT® Model #6L6-00001, INTEL® REALSENSE® 3D Camera as deployed in an ASUS® Laptop Model # N551JQ, etc.). Generally, when the subject 101 is performing the assessment test in association with the perceptual computing device 105, the perceptual computing device 105 will record and analyze the subject 101's performance to identify corrective actions (if necessary) and compensations present, in association with the system 102. Further, the subject 101 may perform the particular assessment test using an application running on a mobile computing device 107 (e.g., tablet, smartphone, etc.). Generally, when the subject 101 is performing the assessment test using an application running on a mobile computing device 107, the subject 101 identifies any corrective actions necessary and any compensations present and inputs the compensations into the application.

Once a sufficient data set has been provided by the subject 101 (e.g., enough reps of the tasks that comprise the particular assessment test), then the data set is transmitted over a network 104 to a compensation analysis and program generation system 102, which, at step 3, receives and parses the data set, processes the data set according to various algorithms to produce an overall score and status, and generates a recommended exercise program based on the results of the processing. In one embodiment, the compensation analysis and program generation system 102 comprises a management module 106 that processes data used during the compensation analysis and program generation process and a database 108 to store data used during the compensation analysis and program generation process (e.g., subject data sets, exercise information, processing algorithms, etc.). Further, the compensation analysis and program generation system 102 may optionally interface with a third party data system 110, over a network 104, to receive information to supplement the program generation process (e.g., electronic health records system, medical diagnostic system, etc.). Additional details of the architecture of the compensation analysis and program generation system 102 will be provided in association with the description of FIG. 2.

Generally, an overall score may be produced by the compensation analysis and program generation system 102 to provide a benchmark for the subject 101's reference. In one embodiment, the overall score is a number out of one hundred that signifies how successfully a subject performed a particular assessment test (e.g., with larger numbers indicating better success). For example, for each identified compensation, the overall score may be reduced by a predetermined amount (e.g., a particular compensation may be worth 3% of the overall score, etc.). In various embodiments, as part of program generation (the details of which will be explained in more detail in connection with the description of FIGS. 3 and 6), the compensation analysis and program generation system 102 permits the registered practitioner 103 to provide input and modifications to the recommended program. Generally, the registered practitioner 103 may insert, change, or remove a particular exercise, modify the particulars of how that exercise is performed (e.g., number of repetitions, frequency within the program, etc.), schedule the exercises for particular days, etc. The completed recommended program, in one embodiment, comprises a schedule of exercises to be performed on various days in various settings.

Referring still to FIG. 1, in various embodiments, the recommended program generated at step 3 comprises a set of subject and compensation specific exercises that are to be performed on various days in various settings. Generally, these exercises are targeted to the particular subject 101 based on the compensations that were identified as part of compensation analysis and are designed to correct the deficiencies that resulted in the identified compensations. In various embodiments, the predetermined number of days and different exercises in different settings may be generated at one time from the same data set (e.g., same input but different varied outputs) so that a practitioner and/or patient does not need to request additional exercises, settings, etc. For example, the recommended program may comprise a predetermined number of days (e.g., 3 or 5) of exercises that can be performed in different settings to achieve similar and/or different results. In one embodiment, the settings comprise a self-care setting wherein the subject 101 performs the exercises by himself/herself, a practitioner light setting wherein the subject 101 performs the exercises with the assistance of a certified practitioner (e.g., strength and conditioning coach, personal trainer, etc.), and a practitioner pro setting wherein the subject 101 performs the exercises with the assistance of a licensed practitioner (e.g., physical therapist, chiropractor, etc.). In various embodiments, these settings permit the recommended exercise program to be modified to better accommodate the subject and/or increase the continuum and continuity of care of an individual with a single intervention system to increase the functional outcomes and decrease potential costs of interventions. For example, if a particular subject is a professional athlete with a serious injury, then the particular subject may perform, as part of his/her recommended exercise program, only those exercises in the practitioner pro setting. In contrast, an amateur athlete with a minor injury may perform only those exercises in the self-care setting.

Generally, the recommended programs for each setting comprise three different stages (alternatively referred to herein as strategies): "restore," "activate," and "move." In one embodiment, the restore strategy should be performed before the activate strategy, which should be performed before the move strategy. Generally, the sequencing of the strategies combined with the specific exercise acute variable progressions (e.g., sets, repetitions, etc.) within each strategy provide specific physiological and physical outcomes that have been researched and proven to improve movement efficiency/quality of movement. In various embodiments, the restore strategy comprises exercises such as foam rolling and static stretching of particular muscles (e.g., foam rolling hamstring, etc.) that inhibit, lengthen, and improve mobility of soft-tissue and joints caused by over-performing muscles, the activate strategy comprises exercises such as isolated muscle activation exercises (e.g., should external rotation, etc.) that activate/strengthen under-performing muscles, and the move strategy comprises exercises such as dynamic exercises that require the use of various integrated muscles (e.g., front lunge to shoulder press, etc.) to reinforce the activation/strengthening and integrated functional re-education of the body.

Once the recommended program has been generated, at step 4 in various embodiments, the recommended program is transmitted over a network 104 to the subject 101, who begins performing the recommended program. Generally (as will be discussed in connection with FIGS. 23-27), the recommended program is provided to the subject 101 in an interactive format so that the subject 101 may indicate whether an exercise has been performed, provide any feedback regarding the performance of the exercise, receive instructions on how to perform an exercise, etc. At the completion of the recommended program, the subject 101 may either return to step 2 to receive another compensation analysis and program generation or the subject 101 may proceed to step 5, wherein the subject 101 reaps the benefits of the program. Generally, at step 5, the subject 101 may experience improved performance, reduced pain, increased physical conditioning, etc. Once the compensation analysis and program generation reaches step 5, the subject 101 may either continue performing the recommended program or a modification thereof or may discontinue the recommended program altogether. To better understand the compensation analysis and program generation process, an overview of the compensation analysis and program generation system 102 may be helpful.

Now referring to FIG. 2, an exemplary architecture 200 of one embodiment of the disclosed compensation analysis and program generation system 102 is shown. As shown, the compensation analysis and program generation system 102 generally comprises a management module 106 and at least one system database 108. In various embodiments, the management module 106 comprises a test performance and data collection engine 401 that is operatively connected to a test data analysis and score calculation engine 501, which is operatively connected to a program generation engine 601. Additionally, the system 102 may be operatively connected, through one or more networks (such as network 104 from FIG. 1), to one or more test performance and data collection devices 403, program display and feedback devices 603, and third party data systems 110. As will be understood by one having ordinary skill in the art, the networks may comprise any connection capable of transferring data between two or more computer systems (e.g., Bluetooth, wireless or wired local-area networks (LANs), cell network, etc.).

In one embodiment, the management module 106 and system database 108 manipulate and store the data used by the system 102. Generally, the management module 106 runs the various engines and processes that comprise the system 102. As will be understood by one having ordinary skill in the art, the management module 106 may be any computing devices (e.g., desktop computer, laptop, servers, tablets, etc.), combination of computing devices, software, hardware, or combination of software and hardware that is capable of running the engines and processes disclosed herein. The system database 108, generally, stores the various subject data sets, algorithms, lists of exercises, information regarding performance of those exercises, and any other data that is used by the system 102. As will be understood by one having ordinary skill in the art, the system database 108 may be any database (e.g., stored in the cloud or on premise, structured as relational, etc.) or combination of databases that is capable of storing the data used by the engines and processes disclosed herein. Generally, the system 102 also optionally interfaces with various third party data systems 110 to retrieve additional information that may be needed or used by the engines or processes disclosed herein. For example, the system 102 may interface with an electronic health records system to retrieve information regarding a particular subject. Additionally, the system 102 may interface with an external exercise database to retrieve additional exercises or information regarding exercises as desired by a practitioner. In various embodiments, the system 102 may interface with a third party data system 110 at any time during the compensation analysis and program generation processes to retrieve additional data as needed by those processes.

Still referring to FIG. 2, in one embodiment, the test performance and data collection engine 401 and test performance and data collection device 403 facilitate the test performance and data collection process (the further details of which will be explained in connection with the descriptions of FIGS. 3 and 4). In one embodiment, the test performance and data collection engine 401 runs the test performance and data collection process to provide a particular test (e.g., movement efficiency test, movement efficiency screen, range of motion test, etc.) that a subject performs to identify any compensations that the subject may have. Generally, the system 102 comprises one or more test performance and data collection devices 403 to interface between the subject and the system 102 so that the subject is aware of which tasks to perform (and how to perform them) and the system 102 is aware of the results of the subject's performance. In various embodiments, the test performance and data collection device 403 may be any device capable of providing the functionality disclosed herein. For example, the test performance and data collection device 403 may be used by a practitioner (e.g., doctor, nurse, physical therapist, coach, personal trainer, parent, etc.) who has been trained according to the present disclosure or a subject in association with an assessment test and may include a computing device (e.g., tablet, laptop, smartphone, desk top, etc.), perceptual computing device (e.g., any device, body sensors, combination of the same, etc. capable of capturing movement in an automated way, examples include a MICROSOFT® KINECT® Model #6L6-00001, INTEL® REALSENSE® 3D Camera as deployed in an ASUS® Laptop Model # N551JQ, etc.), etc. (such as perceptual computing device 105 or mobile computing device 107 from FIG. 1).

Accordingly, the test performance and data collection engine 401 and test performance and data collection device 403 facilitate the test performance and data collection process, which provides the data that is processed by the test data analysis and score calculation engine 501 as part of the test data analysis and score calculation process (the further details of which will be explained in connection with the descriptions of FIGS. 3 and 5). In one embodiment, the test data analysis and score calculation engine 501 calculates the subject's overall score on a particular test and also calculates a unique score for each test exercise, body part, or muscle group that has been tested (e.g., right knee, hamstring, left arm, etc.). In certain embodiments, the overall score may not be used by the system to generate a recommended program but instead provides a benchmark for the subject's reference. In contrast, the unique scores may be used to generate the recommended program so that the program targets the compensations identified by the testing process.

To generate programs, in various embodiments, the program generation engine 601 and program display and feedback device 603 facilitate the program generation process (the further details of which will be explained in connection with the descriptions of FIGS. 3 and 6). Generally, the program generation engine 601 runs the program generation process to generate one or more recommended programs for use by a subject. In one embodiment, the program display and feedback device 603 permits a practitioner to provide input/modifications into the program generation process to further customize the recommended program. For example, the practitioner may input exercise modifications or substitutions along with particular schedules into the program display and feedback device 603. The program display and feedback device 603 also permits a subject to view and interact with their recommended program. For example, the subject may view the particular exercises he/she must perform that day and indicate whether those exercises have been performed, provide feedback regarding their performance, etc. Thus, the program display and feedback device 603 may be any device capable of providing the functionality disclosed herein (e.g., desktop computer, laptop computer, tablet, smartphone, etc.).

Referring now to FIG. 3, a flowchart summarizing an exemplary, high-level process flow 300, according to one embodiment of the present disclosure, is shown. As will be understood by one having ordinary skill in the art, the steps and processes shown in FIG. 3 (and those of all other flowcharts and sequence diagrams shown and described herein) may operate concurrently and continuously, are generally asynchronous and independent, and are not necessarily performed in the order shown. In one embodiment, the compensation analysis and program generation system comprises a test performance and data collection process 400, a test data analysis and score calculation process 500, and a program generation process 600.

Figure 7:
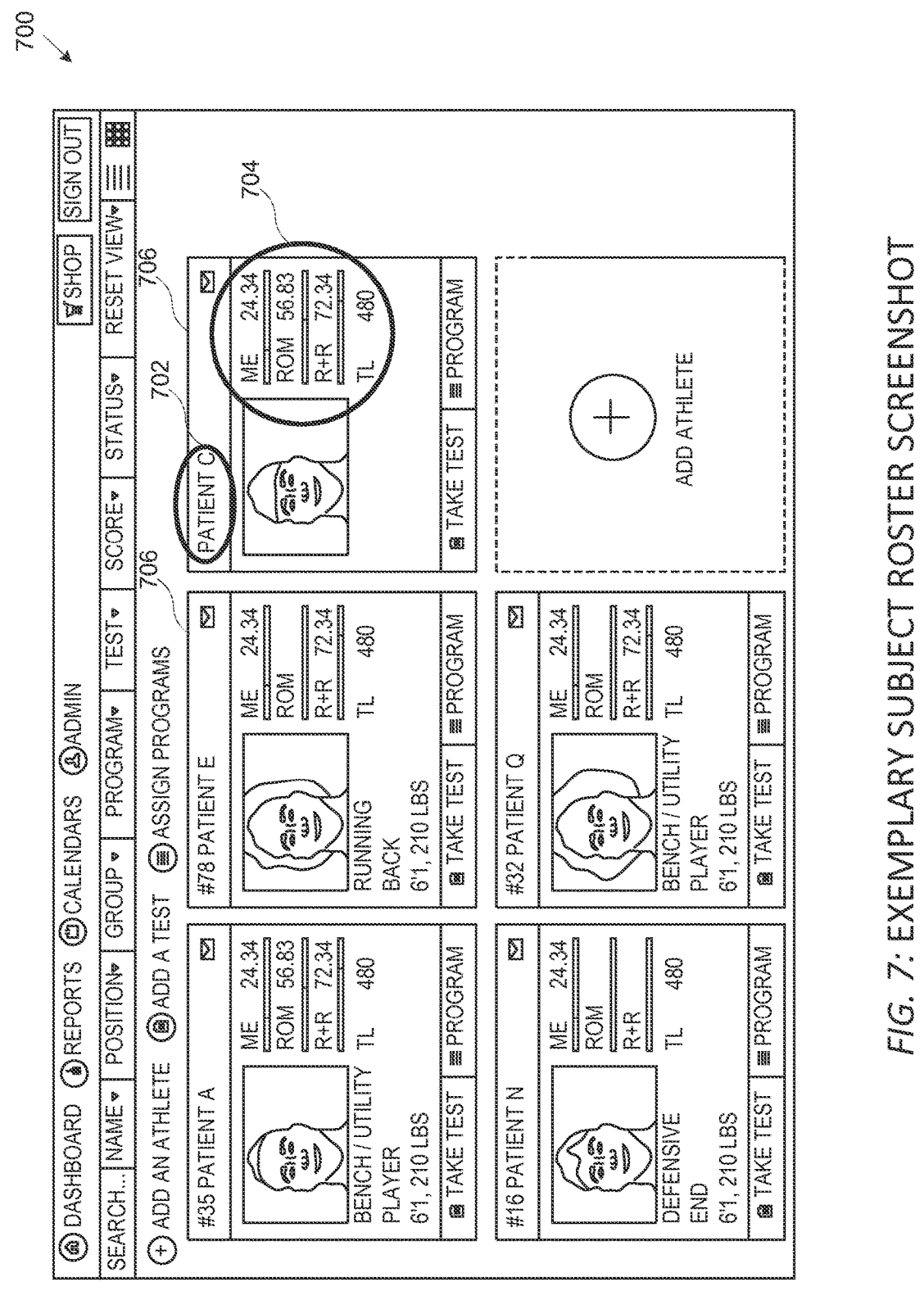

In various embodiments, the test performance and data collection process 400 is performed by the test performance and data collection engine 401 (from FIG. 2). In one embodiment, a practitioner and/or subject uses one or more test performance and data collection devices 403 (from FIG. 2) to conduct the test performance and data collection process 400. Generally, the test performance and data collection process 400 is the process by which the compensation analysis and program generation system requests performance of a particular test designed to identify certain compensations within the kinetic chain that the subject may exhibit and records data regarding the performance of the same. In various embodiments, the requested test may comprise a movement efficiency test (e.g., test comprising the performance of a 2-leg squat, 2-leg squat with heel lift, 1-leg squat, push-up, shoulder movements, trunk/thoracic spine movements, and cervical spine movements to identify the presence of compensations in those tasks; the results of this test are recorded in binary; more details of this test will be explained in association with the description of FIG. 11), movement efficiency screen (e.g., test comprising the performance of a 2-leg squat, 2-leg squat with heel lift, and 1-leg squat to identify the presence of compensations in those tasks; the results of this test are recorded in binary; more details of this test will be explained in association with the description of FIG. 12), range of motion test (e.g., test performed to assess the range of motion that a subject possesses in a particular joint, usually using a goniometer and scored as a percentage of the optimal range suggested by the American Academy of Orthopedic Surgeons; more details of this test will be explained in association with the description of FIG. 13), or a performance test. In one embodiment, the compensations identified may include that the foot turns out, that the foot flattens, that the knees moves in (valgus), that the knee moves out (varus), etc. Generally, the test performance and data collection process 400 receives information regarding the compensations identified directly from the subject/practitioner. The test performance and data collection process 400 will be explained in further detail in association with the description of FIGS. 4 and 7-13.

After the test performance and data collection process 400, in one embodiment, the test data analysis and score calculation process 500 occurs. In various embodiments, the test data analysis and score calculation process 500 is performed by the test data analysis and score calculation engine 501 (from FIG. 2). Generally, the test data analysis and score calculation process 500 is the process by which the compensation analysis and program generation system determines an overall score of a subject on a particular test and also calculates a body-part specific score for that particular test. In one embodiment, the overall score does not factor into or impact the program generation process 600 but is instead a benchmark designed for ease of use by a subject. Generally, the overall score permits a subject to quickly and easily assess their performance. In contrast, the body-party specific score may be used by the program generation process 600 to identify the particular exercises that will correct the compensations and other deficiencies present in the subject. The test data analysis and score calculation process 500 will be generally explained in further detail in association with the description of FIGS. 5 and 14-17.

In one embodiment, the program generation process 600 occurs after the test data analysis and score calculation process 500. In various embodiments, the program generation process 600 is performed by the program generation engine 601 (from FIG. 2). In one embodiment, a practitioner and/or subject uses one or more program display and feedback devices 603 (from FIG. 2) to provide input into the program generation process 600. Generally, the program generation process 600 generates a recommended exercise program that is subject-specific and targeted to correct the identified compensations and other deficiencies. In one embodiment, a practitioner is provided with a recommended exercise program and modifies that program according to their preferences (e.g., substituting exercises, changing the number of repetitions for a particular exercise, etc.). Generally, the practitioner also indicates which days an exercise program should be performed and in which settings (e.g., self-care, practitioner light, practitioner pro, etc.) The program generation process 600 will be generally explained in further detail in association with the description of FIGS. 6 and 18-27.

Now referring to FIG. 4, a flowchart of an exemplary test performance and data collection process 400 is shown, according to one embodiment of the present disclosure. Generally, the exemplary test performance and data collection process 400 is the process by which a subject is tested to determine whether any compensations or other deficiencies are present. In one embodiment, the exemplary test performance and data collection process 400 is performed by the test performance and data collection engine 401 (from FIG. 2). Generally, a subject performs various tasks dependent on the type of test being performed (e.g., movement efficiency test, movement efficiency screen, range of motion test, performance test, etc.) using one or more test performance and data collection devices 403 (from FIG. 2). For example, the subject may perform the tasks in the presence of a practitioner, using a perceptual computing device, or by themselves with a regular computing device. In various embodiments, the steps of the exemplary test performance and data collection process 400 do not change based on the particular test being performed or the particular test performance data collection device 403 being using.

In various embodiments, the exemplary test performance and data collection process 400 begins at step 402 when the practitioner or subject enters initial registration information regarding the subject into the test performance and data collection engine 401 (from FIG. 2). Generally, this initial registration information may include the subject's name, work affiliations, and other identifying information that may be used to recognize the subject within the system and associate information recorded/generated regarding that subject with the subject's record. After receiving the initial registration information, in one embodiment, the test performance and data collection engine 401 requests screening information regarding the subject at step 404. In various embodiments, this screening information may include any information that is relevant to the compensation analysis and program generation processes, such as the subject's biometric information (e.g., height, weight, age, blood pressure, resting heart rate, percent body fat, etc.), typical exercise routine, typical activities, current injury summary (e.g., what is the injury, pain level, how long the injury has persisted, how the injury occurred, etc.), past injury history, etc. Generally, at step 406, the engine receives and stores (e.g., in the system database 108 from FIG. 1) this screening information so that it may be used later by the system. As will occur to one having ordinary skill in the art, the subject, the practitioner, or a combination of both may provide this information to the engine, or the engine could pull the information from a third party data system 110 (from FIG. 1). After receiving the screening information, in various embodiments, the engine receives an indication (from the practitioner and/or subject) to start the test performance and data collection process at step 408. In particular, in one embodiment, the engine receives an indication (e.g., by a subject or practitioner selecting a button on an interface screen) to start a particular test performance (e.g., movement efficiency test, movement efficiency screen, range of motion test, performance test, etc.). Additional information regarding steps 402 through 408 will be provided in association with the description of FIGS. 7-10.

Based on the particular test selected, at step 410 in various embodiments, the engine determines the appropriate testing process template (e.g., that corresponds to the particular selected test). In one embodiment, the testing process template comprises a list of the tasks (e.g., particular movements such as the 2-leg squat, 1-leg squat, push-up, etc.) that the subject should perform to complete a particular test. Thus, at step 412, the engine generally displays a list of the predetermined tasks from the testing process template for selection by the subject/practitioner. Once the subject/practitioner has selected the particular task for evaluation, the engine receives that selection at step 414 in various embodiments. Generally, the tasks may be performed in a particular, pre-defined order according to the template or randomly at the discretion of the practitioner. After receiving the task selection, at step 416, in various embodiments the engine retrieves the task template corresponding to the selected task and provides instructions regarding the performance of the selected task based on that template. In one embodiment, the template and instructions may comprise a video or diagram displaying how to perform the task, (when using a perceptual computing device) an interactive avatar to guide the subject's movements, the particular compensations to look for during performance of the task, etc.

After providing instructions regarding performance of the task, the engine requests performance of the task, in various embodiments, at step 418. After the subject performs the task, in various embodiments, the engine receives and stores information regarding that task performance at step 420. For example, the engine may receive an indication of any compensations present during the performance, (when using a perceptual computing device) a video of the subject's performance, etc. In one embodiment, the engine may receive data in binary format as measured by a practitioner regarding the presence of any compensations and indicated by the practitioner through the selection of a particular radial button on a screen (e.g., "yes" a particular compensation, such as a right foot flattening, was present or "no" a particular compensation was not present).

Still referring to FIG. 4, at step 422, in various embodiments, the engine 401 analyzes the subject's performance to determine whether the data received is relevant and in a format that is useable by the engine (e.g., whether the subject properly performed the task). For example, if the task was a 2-leg squat and the subject/practitioner input information regarding a compensation of the arm, then the engine would recognize that the input was invalid. Similarly, when using a perceptual computing device, the engine may determine whether the subject performed the task with the proper form (e.g., without falling over, using support of a chair, etc.). Based on that analysis, at step 424, the engine determines whether the task performance met a certain predefined criteria (e.g., whether the data is within a particular range, is in a particular format, etc.). For example, if the test requested the subject to perform the task at least 5 times and the subject only performed the task 3 times (or if the data was to be recorded in inches and the input was not within the expected range because it was input in feet), then the engine may determine that the task performance does not meet the predefined criteria. If the task performance did not meet the predefined criteria, then at step 426 the engine takes a predefined action with respect to the task. For example, the engine may analyze the record to determine why the data does not meet the predefined criteria, delete the record, provide remedial instructions (optionally at step 428), and/or generally request that the subject perform the task again (at step 418). If however, the engine determines that the task performance met a certain predefined criteria, then the process proceeds to step 430. Generally, when a practitioner is performing the assessment, the practitioner may perform the steps 422 through 428 and only input information regarding compensations observed during valid performances of the particular task.

At step 430, in various embodiments, the engine determines whether all of the tasks in the particular test have been performed. If all of the tasks have not been performed, than at step 432 the engine queries the subject/practitioner to determine whether the subject/practitioner desires to perform/request performance of additional tasks. If the subject/practitioner desires to perform/request performance of additional tasks, then the engine returns to step 412 and displays a list of tasks for selection by the subject/practitioner. In various embodiments, the subject/practitioner may have medical and/or practical reasons to continue recording task performance or may even desire to record a completely new type of test (e.g., a range of motion test in addition to a movement efficiency test). Conversely, in various embodiments, the subject/practitioner may have medical and/or practical reasons to not record performances for all of the tasks within a particular test (e.g., no time left in the appointment, the subject is fatigued, the subject cannot physically perform a particular task, etc.). In one embodiment, if the subject is going to perform an additional test (e.g., a range of motion test in addition to a movement efficiency test), then the engine may be configured to modify the additional test based on the results of the original test so that the subject only performs tasks that will provide data that will supplement the data recorded during the original test. Additional information regarding steps 410 through 432 will be provided in association with the description of FIGS. 11-13.

In various embodiments, if the engine determines at step 430 that all of the tasks have been performed or at step 432 that no additional tasks are desired, then at step 434, the engine transmits the stored performances from the test performance and data collection engine 401 (from FIG. 2) to the test data analysis and score calculation engine 501 (from FIG. 2) for data analysis and score calculation and the exemplary test performance and data collection process 400 ends thereafter. As will occur to one having ordinary skill in the art, the processes described in FIGS. 4, 5, and 6, may occur concurrently and continuously, are generally asynchronous and independent, and are not necessarily performed in the order shown. Similarly, in one embodiment, the processes described in FIGS. 4, 5, and 6, may be performed by the same engine and/or may be combined into one process, so that the transmission steps do not occur or do not require the use of a network or other similar connection.

Referring now to FIG. 5, a flowchart of an exemplary test data analysis and score calculation process 500 is shown, according to one embodiment of the present disclosure. Generally, the exemplary test data analysis and score calculation process 500 is a process by which the system calculates the subject's overall score for the performed test and the body-part specific scores from the same. In one embodiment, the exemplary test data analysis and score calculation process 500 is performed by the test data analysis and score calculation engine 501 (from FIG. 2).

The exemplary test data analysis and score calculation process 500 generally begins at step 502 when the test data analysis and score calculation engine 501 (from FIG. 2) receives the stored performances from the test performance and data collection engine 401 (from FIG. 2). Accordingly, at step 504 in various embodiments, the test data analysis and score calculation engine 501 parses the stored performances to retrieve the performance data (e.g., information indicating the presence of compensations, etc.). After retrieving the performance data, at step 506, the engine generally pre-processes the performance data to ensure there is sufficient data to conduct the exemplary test data analysis and score calculation process 500.

Thus, in various embodiments at step 508, the engine determines whether additional inputs are recommended. Additional inputs may be recommended, for example, when not enough data was recorded during the exemplary test performance and data collection process 400 or if a particular combination of results within the performance data suggests that a particular condition may be present and further testing regarding that condition would be beneficial. If additional inputs are recommended, then at step 510, the engine generally requests additional inputs based on the results of the pre-processing. Accordingly, the subject/practitioner provides those additional inputs and the engine receives and stores (e.g., in the system database 108 from FIG. 1) those additional inputs at step 512. Alternatively, the engine may query the third party data system 110 (from FIG. 1) as part of steps 510 and 512.

Referring still to FIG. 5, in various embodiments, once the engine has stored those additional inputs or if, at step 508, the engine determined that no additional inputs were recommended, the engine, at step 514, determines the performance data type for the first type of pre-processed performance data (as will be recalled from the description of FIG. 4, the subject may perform multiple tests and record data regarding all of those tests). Generally, the movement efficiency test and movement efficiency screen produce results in binary (e.g., "yes" or "no" indication of whether a particular compensation is present based upon some predefined criteria), whereas the range of motion test produces results as a percentage of the optimal range of motion (e.g., 70% of optimal). In one embodiment, the range of motion test produces results in binary format (e.g., "yes" the percentage of the optimal range is below a certain threshold or "no" it is not). Similarly, the number of data points in a movement efficiency test may be different from the movement efficiency screen and may be different from the range of motion test. Accordingly, the algorithms used to calculate the scores based on those results differ depending on the format of the data. After determining the performance data type, in various embodiments, at step 516, the engine retrieves the algorithm corresponding to that particular performance data type and, at step 518, processes the data according to that algorithm and stores the results of that processing (e.g., in the system database 108 from FIG. 1). As will occur to one having ordinary skill in the art, the processing at step 518 generally results in the overall score and body-part specific scores that are used by the subject as a benchmark and to generate the recommended exercise program, respectively.

For example, the body-part specific scores may be used to generate a list of compensations that are processed to generate the recommended exercise program. In one embodiment, the scores calculated at step 518 are displayed on a program display and feedback device 603 (from FIG. 2). The results (e.g., scores) of the exemplary test data analysis and score calculation process 500 will be discussed in further detail in association with the descriptions of FIGS. 14-17.

After storing the results of the algorithm processing, the engine determines whether additional pre-processed data remains to be processed in various embodiments at step 520. If additional pre-processed data remains to be processed, then the engine returns to step 514 and determines the particular performance data type. If, however, no additional pre-processed data remains to be processed, then the test data analysis and score calculation engine 501 (from FIG. 2) transmits the processed data to the program generation engine 601 (from FIG. 2) and the exemplary test data analysis and score calculation process ends thereafter.

Now referring to FIG. 6, a flowchart depicting an exemplary program generation process 600 is shown, according to one embodiment of the present disclosure. Generally, the exemplary program generation process 600 is the process by which the system generates one or more recommended exercise programs for a subject based on the subject's test performance that is designed to reduce the subject's compensations and other physical deficiencies. In various embodiments, the exemplary program generation process 600 is performed by the program generation engine 601 (from FIG. 2). In one embodiment, a practitioner may modify the recommended exercise program using a program display and feedback device 603 (from FIG. 2). In another embodiment, the subject may view the recommended exercise program, complete the exercises in the program, track the completion of the exercises, and provide feedback regarding the same using a program display and feedback device 603 (from FIG. 2).

The exemplary program generation process 600 generally begins at step 602 when the program generation engine 601 (from FIG. 2) receives the processed data from the test data analysis and score calculation engine 501 (from FIG. 2). In various embodiments, at step 604, the program generation engine 601 retrieves the data set corresponding to the processed data (e.g., the raw data, such as the binary data regarding whether certain compensations were present, and the body-part specific scores, such as those scores calculated from the compensations present around a particular body part like a knee) and, at step 606, identifies the compensations present in that data set. Then, in one embodiment, at step 608, the engine determines whether additional data sets in the processed data need to be analyzed to identify compensations (e.g., if the subject performed both a movement efficiency test and a range of motion test). If additional data sets exist, then the engine returns to step 604. If however, no additional data sets exist, then the engine proceeds to step 610.

In various embodiments, at step 610, the engine applies rules regarding the interaction between compensations to determine and group the compensations into compensation groups. In one embodiment, the compensation interactions permit the system to determine the physical deficiencies causing the compensations and the compensation groups permit the system to recommend exercises to correct those deficiencies. In various embodiments, the compensation interactions may be derived from a practitioner's experience or knowledge, medical literature, trial and error, peer-reviewed research, evidence-based practice (e.g., clinical practice and peer-reviewed research/medical literature), etc. In one embodiment, the compensation interactions may be fairly straightforward. In one embodiment, however, the compensation interactions may be very complex. For example, when multiple compensations are present, their presence can indicate a particular physical deficiency (e.g., a foot turning out and a knee moving in on the same leg may indicate one deficiency such as a quadriceps weakness, whereas a foot flattening and a knee moving out on the same leg may indicate a different deficiency such as a hamstring tightness). In contrast, if a compensation is present in one task (e.g., 2-leg squat) but not in another task (e.g., 1-leg squat), then that may also indicate a particular physical deficiency (e.g., lower back weakness). Generally, the more data sets present, the more effective the recommended exercise program will be as the engine may be able to weight certain compensation interactions differently from other compensation interactions to more accurately identify the exercises that will correct the identified compensations and physical deficiencies. Accordingly, the engine identifies the particular deficiencies and corresponding compensation groups that are relevant to a particular subject.

Still referring to FIG. 6, at step 612, in various embodiments, the engine retrieves criticality factors relating to the identified compensation groups. In one embodiment, the criticality factors generally permit the system to rank the various identified compensation groups in order of importance/severity. For example, the system may have an overall ranking of compensation groups to permit it to suggest exercises to correct the most troubling/problematic compensations. Additionally, in one embodiment, the criticality factors may be determined based on the subject (e.g., weighting the compensations in a baseball pitcher's arm above those compensations in the pitcher's legs but weighting the compensations in a football running back's knees above those in the running back's arms). Optionally, in one embodiment, the engine may filter, at step 614, the compensation groups based on those criticality factors or other predefined criteria to remove those compensation groups that are not of a certain level of relevancy to the subject (e.g., removing compensation groups relating to the non-shooting arm of a basketball player).

At step 616, in various embodiments, the engine retrieves all of the exercises that may be used to correct the compensation groups that it has identified. Generally, the system may store a large collection of exercises that have multiple purposes and impact various different compensation groups (e.g., foam rolling of the hamstring, lunges, etc.). Accordingly, at step 618, the engine generates a list of exercise groups (e.g., groups the exercises retrieved at step 616 into groups of similar exercises with similar purposes/benefits such as quadriceps strengthening exercises, shoulder strengthening exercises, etc.) based on interdependency rules for the compensation groups, which it retrieves at step 618 as well. In one embodiment, the generated list of exercise groups comprises all of the exercises that may target the compensations identified in a certain subject and may relate those exercises or exercise groups to the particular compensations that they target (e.g., lunges for improving a compensation in the knee, etc.). Generally, the compensation groups may also have interdependencies that permit one exercise or group of exercises to correct for more than one compensation (e.g., quadriceps and hamstring exercises, etc.). Thus, the engine generates a list of exercise groups to optimize the efficiency of the recommended exercise program (e.g., quadriceps and hamstring exercises, shoulder exercises, etc.). As will occur to one having ordinary skill in the art, subjects do not have unlimited amounts of time, and the ability to target multiple compensations with one exercise group is extremely beneficial if just for the time-saving value alone.

Referring still to FIG. 6, in various embodiments, at step 620, after generating the list of exercise groups, the engine applies predefined ordering methods to the list of exercise groups so that the exercises are performed in a predetermined order, which permits the exercises to build on each other and contribute to a subject's improvement instead of counteracting each other (e.g., those that comprise the "restore" strategy may be performed before those that comprise the "activate" strategy, which may be performed before those that comprise the "move" strategy). Accordingly, at step 622, the engine modifies the exercise groups based on various parameters (e.g., criticality factors, compensation groups, exercise groups, ordering methods, etc.) to cull the list of exercise groups into a set of exercise groups that may be compiled into a limited recommended exercise program (e.g., a program with a limited number of exercises).

In various embodiments, at step 624, the engine compiles the recommended exercise programs (e.g., three days of exercises for each of three different settings—self-care, practitioner light, and practitioner pro) and stores them (e.g. in the system database 108 from FIG. 1). Generally, the engine uses the same input data (e.g., binary data regarding compensations) and generates multiple different programs (e.g., programs for different days and in different settings) and compiles those programs into one recommended exercise program that a practitioner or subject may modify to suit the subject. For example, the engine may generate five days of programs that occur in a self-care setting (e.g., foam rolling hamstring, etc.), five days of programs that occur in a practitioner light setting (e.g., assisted hamstring stretching, etc.), and five days of programs that occur in a practitioner pro setting (e.g., hamstring massage, etc.), all based on the same input data. Accordingly, at step 626, in one embodiment, the engine transmits the generated programs to the subject/practitioner (e.g., for viewing on the program display and feedback device 603 from FIG. 2). In various embodiments, the engine requests modifications to the generated programs at step 628. For example, the practitioner may modify the programs based on the practitioner's preferences (e.g., a particular exercise that the practitioner prefers over another exercise, etc.) or to schedule the exercise program for certain days (e.g., the first day of self-care on Mondays, the second day of practitioner light on Tuesdays, the third day of self-care on Wednesdays, etc.). At step 630, in various embodiments, the engine determines whether the practitioner will modify the generated exercise programs. If the practitioner will modify the generated exercise programs, then at step 632 in one embodiment, the engine receives the modifications and stores them (e.g., in the system database 108 from FIG. 1). In various embodiments, at step 634 the engine modifies and stores (e.g., in the system database 108 from FIG. 1) the generated exercise programs based on the received modifications and returns to step 626 to transmit the modified exercise programs to the subject/practitioner.

If, however, the program generation engine 601 (from FIG. 2) determines that the practitioner will not modify the generated recommended exercise program at step 630, then the exemplary program generation process 600 ends thereafter. Additional details of the exemplary program generation process 600 will be explained in connection with the description of FIGS. 18-22. To better understand the compensation analysis and program generation processes, exemplary screenshots of one embodiment of the compensation analysis and program generation system may be useful.

Exemplary Screenshots

Referring now to FIG. 7, a screenshot of an exemplary subject roster screen 700 of a compensation analysis and program generation system is shown according to one embodiment of the present disclosure. In one embodiment, the exemplary subject roster screen 700 provides a graphical view of all of the subjects of a particular practitioner, displaying relevant information, such as the subject name 702 or scores 704 on particular tests (e.g., the overall score/results from a particular, previously-performed assessment test, such as 24.34 on the movement efficiency test, 56.83 on the range of motion test, etc.), in subject display blocks 706. Generally, the exemplary subject roster screen 700 permits the practitioner to quickly view the practitioner's subjects and provides access to the subject's records. In one embodiment, the exemplary subject roster screen 700 is displayed on a test performance and data collection device 403 (from FIG. 2). Similarly, FIG. 8 is a screenshot shot of an exemplary subject roster screen 800, in list view, of a compensation analysis and program generation system, according to one embodiment of the present disclosure. The information provided in exemplary subject roster screen 800, is generally the same as the information provided in exemplary subject roster screen 700, except that the information is provided in rows 802. For example, the subject name 702 and scores 704 (e.g., calculated as part of the exemplary test data analysis and score calculation process 500 from FIG. 5) are the same. In various embodiments, some of the information in the two screens may be different but it should be understood that the information and functionality between the screens does not change (e.g., the different views may display different fields of information but the information within the fields remains the same). For example, by clicking on a subject's name 702 on either screen, the practitioner may access the subject's summary screen.

Now referring to FIG. 9, a screenshot of an exemplary subject summary screen 900 of a compensation analysis and program generation system is shown, according to one embodiment of the present disclosure. Generally, the exemplary subject summary screen 900 provides the detailed record of a particular subject (e.g., subject name 702, scores 704, list 902 of those activities to be performed that day, summary 904 of the subject's historical performance, schedule 906 of the activities that the subject is performing, etc.). In one embodiment, the exemplary subject summary screen 900 may be viewed by either the subject to which it corresponds or a practitioner on a test performance and data collection device 403 (from FIG. 2). In various embodiments, the exemplary subject summary screen 900 is updated in real time based on information provided to the system by the subject and/or practitioner (e.g., as part of steps 402 through 406 in FIG. 4) and may be modified to provide the subject/practitioner with access to various information and functionality. For example, the exemplary subject summary screen 900 may have a test button 908 that permits the subject/practitioner to go to a test-selection screen.

Referring now to FIG. 10, a screenshot of an exemplary test-selection screen 1000 of a compensation analysis and program generation system is shown, according to one embodiment of the present disclosure. Generally, the exemplary test-selection screen 1000 provides the subject and/or practitioner with a list of tests that the subject may perform by selecting a particular test and is displayed on a test performance and data collection device 403 (from FIG. 2). For example, the subject may perform any of the assessment tests (e.g., movement efficiency test 1002, movement efficiency screen 1004, range of motion test 1006, etc.), the performance tests (e.g., performance test 1008, etc.), or the recovery tests (e.g., daily test 1010, weekly test 1012, etc.). In one embodiment, selecting a particular test on the exemplary test-selection screen 1000 corresponds to providing an indication to start the test performance and data collection process at step 408 (from FIG. 4). Once the system has received an indication to start the test performance and data collection process, generally the system displays a performance and data collection screen.

Now referring to FIG. 11, a screenshot of an exemplary movement efficiency test performance and data collection screen 1100 of a compensation analysis and program generation system is shown, according to one embodiment of the present disclosure. Similarly, FIG. 12 shows a screenshot of an exemplary movement efficiency screen performance and data collection screen 1200 of a compensation analysis and program generation system, according to one embodiment of the present disclosure. Finally, FIG. 13 shows a screenshot of an exemplary range of motion test performance and data collection screen 1300 of a compensation analysis and program generation system, according to one embodiment of the present disclosure. Generally, the information displayed and received through the performance and data collection screens 1100, 1200, and 1300 corresponds to the information displayed and received at steps 412 through 432 (from FIG. 4) on a test performance and data collection device 403 (from FIG. 2). In various embodiments, the performance and data collection screens 1100, 1200, and 1300 display information regarding the particular test being performed (e.g., movement efficiency test 1102, movement efficiency screen 1202, and range of motion test 1302), the status 1104, 1204, 1304 of progress within that test (e.g., which task has been performed, which task will be next, and the scores calculated as part of the exemplary test data analysis and score calculation process 500 from FIG. 5), the particular task 1106, 1206, 1306 that is being performed, the compensation 1112, 1308 to look for during performance of that task, and a place 1114, 1310, 1312 to input data regarding the particular compensation. In one embodiment, as part of the movement efficiency test or screen, the system provides the particular viewpoint 1108 (e.g., front, back, side, etc. of the subject) from which to view a compensation, checkpoint 1110 (e.g., foot, knee, etc.) where to look for a compensation, and the particular compensation 1112 (e.g., foot flattens, etc.) to look for in that checkpoint 1110.

Generally, for at least the movement efficiency tests and screens, the data received regarding a particular compensation 1112 is in binary (e.g., either "yes" a compensation is present or "no" it is not); thus, the place 1114 to input data may be a radial button that indicates "yes" or "no" regarding the compensation. For example, the practitioner may observe, from the front while the subject performs a 2-leg squat, that the subject's left foot flattens and would select the "yes" option of a radial button 1114 to provide that information to the system. In one embodiment, as part of the range of motion test, the system provides the particular joint or motion 1306 that should be measured (e.g., ankle dorsiflexion, etc.), the optimal range of motion 1308 for that joint or motion, and a place to enter the actual range of motion for the right joint 1310 and the left joint 1312. For example, a practitioner may measure that a subject's right ankle dorsiflexion is 10° and record that in the appropriate field 1310 to provide that information to the system. Once the data collection is complete, the system generates an analysis, which it displays as part of a report screen.

Referring now to FIG. 14 (consisting of FIGS. 14A and 14B), screenshots of an exemplary movement efficiency test report screen 1400A, 1400B of a compensation analysis and program generation system are shown, according to one embodiment of the present disclosure. Similarly, FIG. 15 (consisting of FIGS. 15A and 15B) shows screenshots of an exemplary movement efficiency screen report screen 1500A, 1500B of a compensation analysis and program generation system, according to one embodiment of the present disclosure. Further, FIG. 16 (consisting of FIGS. 16A and 16B) shows screenshots of an exemplary range of motion test report screen 1600A, 1600B of a compensation analysis and program generation system, according to one embodiment of the present disclosure. Finally, FIG. 17 shows a screenshot of an exemplary performance test report screen 1700 of a compensation analysis and program generation system, according to one embodiment of the present disclosure. In various embodiments, the report screens 1400A, 1500A, 1600A display the overall score 1402, 1502, 1602 that the subject received on the test, the body part specific scores 1404, 1504, 1604 that the subject received on the test, and the task specific scores 1406, 1506, 1606 that the subject received on the test. Additionally, in various embodiments, the report screens 1400B, 1500B, 1600B, 1700 display an upper and lower body index 1408, 1508, 1608 to compare the subject's upper and lower body, a symmetry index 1410, 150, 1610 to compare the subject's left and right sides, and the detailed results 1412, 1512, 1612, 1702 of the tests.

Generally, the displayed scores and indices may be calculated as part of the exemplary test data analysis and score calculation process 500 from FIG. 5 and viewed on a program display and feedback device 603 (from FIG. 2). In one embodiment, after viewing the report screens 1400B, 1500B, 1600B, the subject or practitioner may select to complete the program 1416, 1516, 1616, which displays the program generation screen.

Now referring to FIG. 18, a screenshot of an exemplary program generation screen 1800 of a compensation analysis and program generation system is shown, according to one embodiment of the present disclosure. In various embodiments the exemplary program generation screen 1800 displays a list of exercises 1802 that are recommended based on the results of the subject's test performance (e.g., as part of steps 602 through 626 from FIG. 6) on a program display and feedback device 603 (from FIG. 2). Generally, the exercises 1802 are grouped according to the different strategies 1804 (e.g., "restore," "activate," and "move"), provided for one of three different days 1806, and provided for one of three different settings 1808 (e.g., self-care, practitioner light, and practitioner pro). Generally, the practitioner may edit the recommended exercise program (e.g., as part of steps 628 through 634 from FIG. 6). For example, the practitioner may change the number of sets or duration of a particular exercise, add/substitute different exercises (e.g., by clicking the add exercise button 1810), or schedule the days and settings on the program for different days of the week (e.g., by clicking the save and continue button 1812). After clicking the add exercise button 1810, a program modification screen may be shown. Similarly, after clicking the save and continue button 1812, a program scheduling screen may be shown.

Referring now to FIG. 19, a screenshot of an exemplary program modification screen 1900 of a compensation analysis and program generation system is shown, according to one embodiment of the present disclosure. Generally, the exemplary program modification screen 1900 permits the practitioner to search 1902 or browse the exercises by body part 1904, on a program display and feedback device 603 (from FIG. 2), to find a particular exercise 1906 with which to supplement the recommended exercise program. In one embodiment, each exercise 1906 includes instructions and videos 1908 that explain how to perform the exercise. The practitioner may generally assign an exercise to one or both sides of the body 1910 before selecting to add the exercise 1912 to the recommended exercise program. After selecting to add the exercise 1912, an exercise modification screen may be displayed.

Now referring to FIG. 20, a screenshot of an exemplary exercise modification screen 2000 of a compensation analysis and program generation system is shown, according to one embodiment of the present disclosure. In various embodiments, the exemplary exercise modification screen 2000 permits the practitioner to modify the exercise, from a program display and feedback device 603 (from FIG. 2), before adding it to the recommended exercise program (e.g., by changing the week 2002 that the subject should perform the exercise, the number of sets 2004 of the exercise that the subject should perform, the number of repetitions 2006 within each set that the subject should perform, the duration 2008 of repetitions, the tempo 2010 of the repetitions, etc.). Once the practitioner is ready to add the exercise to the recommended exercise program, the practitioner selects the save button 2012 and the exercise is added to the program. Referring now to FIG. 21, a screenshot of an exemplary program scheduling screen 2100 of a compensation analysis and program generation system is shown, according to one embodiment of the present disclosure. Similarly, FIG. 22 shows a screenshot of an alternative, exemplary program scheduling screen 2200 of a compensation analysis and program generation system, according to one embodiment of the present disclosure. Generally, the exemplary program scheduling screen 2100, 2200 permits the practitioner to schedule the start date 2102 and the end date 2104 for the program from a program display and feedback device 603 (from FIG. 2). Additionally, the practitioner may select the particular setting 2106 (e.g., self-care, practitioner light, practitioner pro) and program day 2108 that a subject is to perform on a particular date. Thus, the practitioner modifies the recommended exercise program to provide it to the subject so that the subject may complete the recommended exercise program.

Now referring to FIG. 23, a screenshot of an exemplary program summary screen 2300, as displayed in a mobile application on a mobile device, of a compensation analysis and program generation system is shown, according to one embodiment of the present disclosure. Generally, the exemplary program summary screen 2300 may be displayed on a program display and feedback device 603 (from FIG. 2) and permits a subject to readily view and keep track of the exercises groups, exercises, other drills, etc. that the subject is scheduled to perform that day to facilitate the subject's completion of the recommended exercise program. For example, the exemplary program summary screen 2300 indicates those exercise groups that have yet to be performed (e.g., movement prep 2302) and those drills that have already been completed as indicated by the subject (e.g., recovery and readiness test 2304). Similarly, in one embodiment, by selecting an exercise group (e.g., movement prep 2302), the subject may view the exercises that comprise that group. For example, FIG. 24 shows a screenshot of an exemplary exercise list screen 2400, as displayed in a mobile application, of a compensation analysis and program generation system, according to one embodiment of the present disclosure.

Generally, the exemplary exercise list screen 2400 may be displayed on a program display and feedback device 603 (from FIG. 2) and permits a subject to readily view and keep track of the specific exercises (e.g., right calf foam roll 2402) within an exercise group that the subject is scheduled to perform that day. Further, by selecting a specific exercise (e.g., right calf foam roll 2402), the subject may view details regarding that exercise. Thus, FIG. 25 shows a screenshot of an exemplary exercise list screen 2500, in detail view as displayed in a mobile application, of a compensation analysis and program generation system, according to one embodiment of the present disclosure. Generally, the exemplary exercise list screen 2500 may be displayed on a program display and feedback device 603 (from FIG. 2) and permits a subject to readily view information (e.g., instructions, instructional videos, etc.) regarding a specific exercise (e.g., right calf foam roll 2402). After completing a recommended exercise program, the subject may be curious regarding their progress in that same program.

Referring now to FIG. 26, a screenshot of an exemplary test result and progress summary screen 2600, as displayed in a mobile application, of a compensation analysis and program generation system is shown, according to one embodiment of the present disclosure. In various embodiments, the exemplary test progress summary screen 2600 permits a user to view their progress regarding a particular test (e.g., range of motion, etc.) or recommended exercise program and may be displayed on a program display and feedback device 603 (from FIG. 2). Similarly, FIG. 27 shows a screenshot of an exemplary weekly progress summary screen 2700, as displayed in a mobile application, of a compensation analysis and program generation system, according to one embodiment of the present disclosure. In various embodiments, the exemplary weekly progress summary screen 2600 permits a user to view their progress from the past week in regards to a particular recommended exercise program and may be displayed on a program display and feedback device 603 (from FIG. 2). In another embodiment, the exemplary weekly progress summary screen 2600 may be expanded to show a user's progress from any period of time (e.g., week, month, 3 months, half a year, etc.). Thus, the disclosed compensation analysis and program generation system facilitates compensation analysis and targeted, corrective program generation processes.

From the foregoing, it will be understood that various aspects of the processes described herein are software processes that execute on computer systems that form parts of the system. Accordingly, it will be understood that various embodiments of the system described herein are generally implemented as specially-configured computers including various computer hardware components and, in many cases, significant additional features as compared to conventional or known computers, processes, or the like, as discussed in greater detail herein. Embodiments within the scope of the present disclosure also include computer-readable media for carrying or having computer-executable instructions or data structures stored thereon. Such computer-readable media can be any available media which can be accessed by a computer, or downloadable through communication networks. By way of example, and not limitation, such computer-readable media can comprise various forms of data storage devices or media such as RAM, ROM, flash memory, EEPROM, CD-ROM, DVD, or other optical disk storage, magnetic disk storage, solid state drives (SSDs) or other data storage devices, any type of removable nonvolatile memories such as secure digital (SD), flash memory, memory stick, etc., or any other medium which can be used to carry or store computer program code in the form of computer-executable instructions or data structures and which can be accessed by a general purpose computer, special purpose computer, specially-configured computer, mobile device, etc.

When information is transferred or provided over a network or another communications connection (either hardwired, wireless, or a combination of hardwired or wireless) to a computer, the computer properly views the connection as a computer-readable medium. Thus, any such a connection is properly termed and considered a computer-readable medium. Combinations of the above should also be included within the scope of computer-readable media. Computer-executable instructions comprise, for example, instructions and data which cause a general purpose computer, special purpose computer, or special purpose processing device such as a mobile device processor to perform one specific function or a group of functions.

Those skilled in the art will understand the features and aspects of a suitable computing environment in which aspects of the disclosure may be implemented. Although not required, some of the embodiments of the claimed inventions may be described in the context of computer-executable instructions, such as program modules or engines, as described earlier, being executed by computers in networked environments. Such program modules are often reflected and illustrated by flow charts, sequence diagrams, exemplary screen displays, and other techniques used by those skilled in the art to communicate how to make and use such computer program modules. Generally, program modules include routines, programs, functions, objects, components, data structures, application programming interface (API) calls to other computers whether local or remote, etc. that perform particular tasks or implement particular defined data types, within the computer. Computer-executable instructions, associated data structures and/or schemas, and program modules represent examples of the program code for executing steps of the methods disclosed herein. The particular sequence of such executable instructions or associated data structures represent examples of corresponding acts for implementing the functions described in such steps.

Those skilled in the art will also appreciate that the claimed and/or described systems and methods may be practiced in network computing environments with many types of computer system configurations, including personal computers, smartphones, tablets, hand-held devices, multiprocessor systems, microprocessor-based or programmable consumer electronics, networked PCs, minicomputers, mainframe computers, and the like. Embodiments of the claimed invention are practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

An exemplary system for implementing various aspects of the described operations, which is not illustrated, includes a computing device including a processing unit, a system memory, and a system bus that couples various system components including the system memory to the processing unit. The computer will typically include one or more data storage devices for reading data from and writing data to. The data storage devices provide nonvolatile storage of computer-executable instructions, data structures, program modules, and other data for the computer.

Computer program code that implements the functionality described herein typically comprises one or more program modules that may be stored on a data storage device. This program code, as is known to those skilled in the art, usually includes an operating system, one or more application programs, other program modules, and program data. A user may enter commands and information into the computer through keyboard, touch screen, pointing device, a script containing computer program code written in a scripting language or other input devices (not shown), such as a microphone, etc. These and other input devices are often connected to the processing unit through known electrical, optical, or wireless connections.

The computer that affects many aspects of the described processes will typically operate in a networked environment using logical connections to one or more remote computers or data sources, which are described further below. Remote computers may be another personal computer, a server, a router, a network PC, a peer device or other common network node, and typically include many or all of the elements described above relative to the main computer system in which the inventions are embodied. The logical connections between computers include a local area network (LAN), a wide area network (WAN), virtual networks (WAN or LAN), and wireless LANs (WLAN) that are presented here by way of example and not limitation. Such networking environments are commonplace in office-wide or enterprise-wide computer networks, intranets, and the Internet.

When used in a LAN or WLAN networking environment, a computer system implementing aspects of the invention is connected to the local network through a network interface or adapter. When used in a WAN or WLAN networking environment, the computer may include a modem, a wireless link, or other mechanisms for establishing communications over the wide area network, such as the Internet. In a networked environment, program modules depicted relative to the computer, or portions thereof, may be stored in a remote data storage device. It will be appreciated that the network connections described or shown are exemplary and other mechanisms of establishing communications over wide area networks or the Internet may be used.

While various aspects have been described in the context of a preferred embodiment, additional aspects, features, and methodologies of the claimed inventions will be readily discernible from the description herein, by those of ordinary skill in the art. Many embodiments and adaptations of the disclosure and claimed inventions other than those herein described, as well as many variations, modifications, and equivalent arrangements and methodologies, will be apparent from or reasonably suggested by the disclosure and the foregoing description thereof, without departing from the substance or scope of the claims. Furthermore, any sequence(s) and/or temporal order of steps of various processes described and claimed herein are those considered to be the best mode contemplated for carrying out the claimed inventions. It should also be understood that, although steps of various processes may be shown and described as being in a preferred sequence or temporal order, the steps of any such processes are not limited to being carried out in any particular sequence or order, absent a specific indication of such to achieve a particular intended result. In most cases, the steps of such processes may be carried out in a variety of different sequences and orders, while still falling within the scope of the claimed inventions. In addition, some steps may be carried out simultaneously, contemporaneously, or in synchronization with other steps.

The embodiments were chosen and described in order to explain the principles of the claimed inventions and their practical application so as to enable others skilled in the art to utilize the inventions and various embodiments and with various modifications as are suited to the particular use contemplated. Alternative embodiments will become apparent to those skilled in the art to which the claimed inventions pertain without departing from their spirit and scope. Accordingly, the scope of the claimed inventions is defined by the appended claims rather than the foregoing description and the exemplary embodiments described therein.

What is claimed is:

1. A method, comprising the steps of:

receiving an electronic request at an electronic computing device for completion of a physical evaluation test relating to an athlete;

retrieving a predefined electronic template from a system database corresponding to the physical evaluation test, the predefined electronic template comprising data relating to a plurality of physical movement tasks for performance by the athlete, each physical movement task comprising a particular static, transitional, or dynamic movement and being associated with one or more identifiable compensations, each identifiable compensation having only two possible outcomes comprising a first outcome indicative of the presence of the particular identifiable compensation during completion by the athlete of the respective physical movement task and a second outcome indicative of the absence of the particular identifiable compensation during completion by the athlete of the respective physical movement task, wherein the identifiable compensation is present when a particular body part of the athlete moves in a predefined manner, whereby the movement indicates that the athlete possesses a particular physical deficiency;

retrieving predefined motion range parameters for each physical movement task from the system database, wherein the predefined motion range parameters define movement ranges that are considered either first outcomes or second outcomes;

scanning, via a perceptual computing device, the body of the athlete;

generating, based on the scan of the body of the athlete, a skeletal body model of the athlete;

displaying, via the electronic computing device, an indication to perform at least one of the plurality of physical movement tasks;

during completion of the athlete's performance of the at least one of the plurality of physical movement tasks, recording, via the perceptual computing device having at least one sensor to record data corresponding to the athlete's movements, performance data specifically corresponding to the performance by the athlete of the at least one of the plurality of physical movement tasks;

mapping the performance data to the skeletal body model to define a movement of at least a portion of the skeletal body model;

upon completion of the athlete's performance of the at least one of the plurality of physical movement tasks, comparing the movement of the at least the portion of the skeletal body model to a particular motion range parameter corresponding to the at least one of the plurality of physical movement tasks to determine either the first outcome or the second outcome of the particular identifiable compensation corresponding to whether the particular body part of the athlete specifically moved in the predefined manner during the athlete's performance of the at least one of the plurality of physical movement tasks;

saving, via the electronic computing device, the determined either the first outcome or the second outcome of the particular identifiable compensation in the system database in association with an instance of the physical evaluation test and the respective physical movement task; and automatically generating at least one exercise program for the athlete, wherein the at least one exercise program is specifically tailored to the athlete according to one or more predefined program generation rules based on the determined either the first outcome or the second outcome of the particular identifiable compensation, and wherein the athlete performs the at least one exercise program.

2. The method of claim 1, further comprising the steps of:

determining, based on the predefined electronic template, whether determinations of either the first outcome or the second outcome have been received for all of the one or more identifiable compensations relating to the respective physical movement task;

upon determination that one or more determinations have not been received for one or more particular identifiable compensations, requesting, via the electronic computing device, determination of either the first outcome or the second outcome for the one or more particular identifiable compensations;

receiving a determination of either the first outcome or the second outcome for the one or more particular identifiable compensations, wherein the determination of either the first outcome or the second outcome is made in response to the athlete's performance of the respective physical movement task; and saving, via the electronic computing device, the received determination of either the first outcome or the second outcome for the one or more particular identifiable compensations in the system database in association with an instance of the physical evaluation test and the respective physical movement task.

3. The method of claim 1, further comprising the steps of:

determining, based on the predefined electronic template, whether each of the plurality of physical movement tasks has been performed by the athlete;

upon determination that one or more particular physical movement tasks have not been performed by the athlete, displaying, via the electronic computing device, the one or more particular physical movement tasks for performance by the athlete;

receiving, for the one or more particular physical movement tasks, a determination of either the first outcome or the second outcome of the particular identifiable compensation, wherein the determination of either the first outcome or the second outcome is made in response to the athlete's performance of the one or more particular physical movement tasks; and saving, via the electronic computing device, the received determination of either the first outcome or the second outcome of the particular identifiable compensation in the system database in association with an instance of the physical evaluation test and the respective physical movement task.

4. The method of claim 1, wherein the at least one exercise program comprises a specifically-ordered set of physical exercises, wherein the one or more predefined program generation rules determine the specific order of physical exercises.

5. The method of claim 4, wherein the one or more predefined program generation rules compare the determined either the first outcome or the second outcome of the particular identifiable compensation to a predetermined ranking of the one or more identifiable compensations, wherein the predetermined ranking is based on particular body parts associated with each of the one or more identifiable compensations.

6. A method, comprising the steps of:

receiving an electronic request at an electronic computing device for completion of a physical evaluation test relating to a test subject;

retrieving a predefined electronic template from a system database corresponding to the physical evaluation test, the predefined electronic template comprising data relating to a plurality of physical movement tasks for performance by the test subject, each physical movement task being associated with one or more identifiable compensations, each identifiable compensation having only two possible outcomes comprising a first outcome indicative of the presence of the particular identifiable compensation during completion by the test subject of the respective physical movement task and a second outcome indicative of the absence of the particular identifiable compensation during completion by the test subject of the respective physical movement task;

retrieving predefined motion range parameters for each physical movement task from the system database, wherein the predefined motion range parameters define movement ranges that are considered either first outcomes or second outcomes;

scanning, via a perceptual computing device, the body of the test subject;

generating, based on the scan of the body of the test subject, a skeletal body model of the test subject;

displaying, via the electronic computing device, an indication to perform at least one of the plurality of physical movement tasks;

during completion of the test subject's performance of the at least one of the plurality of physical movement tasks, recording, via the perceptual computing device having at least one sensor to record data corresponding to the test subject's movements, performance data specifically corresponding to the performance by the test subject of the at least one of the plurality of physical movement tasks;

mapping the performance data to the skeletal body model to define a movement of at least a portion of the skeletal body model;

upon completion of the test subject's performance of the at least one of the plurality of physical movement tasks, comparing the movement of the at least the portion of the skeletal body model to a particular motion range parameter corresponding to the at least one of the plurality of physical movement tasks to determine either the first outcome or the second outcome of the particular identifiable compensation corresponding to whether the particular body part of the test subject specifically moved in the predefined manner during the test subject's performance of the at least one of the plurality of physical movement tasks;

saving, via the electronic computing device, the determined either the first outcome or the second outcome of the particular identifiable compensation in the system database in association with an instance of the physical evaluation test and the respective physical movement task; and automatically generating at least one exercise program for the test subject, wherein the at least one exercise program is specifically tailored to the test subject according to one or more predefined program generation rules based on the determined either the first outcome or the second outcome of the particular identifiable compensation, and wherein the test subject performs the at least one exercise program.

7. The method of claim 6, further comprising the steps of:

determining, based on the predefined electronic template, whether determinations of either the first outcome or the second outcome have been received for all of the one or more identifiable compensations relating to the respective physical movement task;

upon determination that one or more determinations have not been received for one or more particular identifiable compensations, requesting, via the electronic computing device, determination of either the first outcome or the second outcome for the one or more particular identifiable compensations;

receiving a determination of either the first outcome or the second outcome for the one or more particular identifiable compensations, wherein the determination of either the first outcome or the second outcome is made in response to the test subject's performance of the respective physical movement task; and saving, via the electronic computing device, the received determination of either the first outcome or the second outcome for the one or more particular identifiable compensations in the system database in association with an instance of the physical evaluation test and the respective physical movement task.

8. The method of claim 6, further comprising the steps of:
determining, based on the predefined electronic template, whether each of the plurality of physical movement tasks has been performed by the test subject;
upon determination that one or more particular physical movement tasks have not been performed by the test subject, displaying, via the electronic computing device, the one or more particular physical movement tasks for performance by the test subject;
receiving, for the one or more particular physical movement tasks, a determination of either the first outcome or the second outcome of the particular identifiable compensation, wherein the determination of either the first outcome or the second outcome is made in response to the test subject's performance of the one or more particular physical movement tasks; and
saving, via the electronic computing device, the received determination of either the first outcome or the second outcome of the particular identifiable compensation in the system database in association with an instance of the physical evaluation test and the respective physical movement task.

9. The method of claim 6, wherein the physical movement task comprises a particular transitional movement.

10. The method of claim 6, wherein the physical movement task comprises a particular dynamic movement.

11. The method of claim 6, wherein the physical movement task comprises a measurement of a range of motion of a particular joint of the test subject.

12. The method of claim 6, wherein the physical movement task comprises a particular static movement.

13. The method of claim 6, wherein the identifiable compensation is present when a particular body part of the test subject moves in a predefined manner, whereby the movement indicates that the test subject possesses a particular physical deficiency.

14. The method of claim 1, wherein the perceptual computing device comprises a singular unit that houses a processor and the one or more sensors.

15. The method of claim 1, wherein the particular movement range parameter defines whether a knee of the athlete rotates inwardly during the athlete's performance of the at least one of the plurality of physical movement tasks.

16. The method of claim 1, wherein the particular movement range parameter defines whether a knee of the athlete rotates outwardly during the athlete's performance of the at least one of the plurality of physical movement tasks.

17. The method of claim 1, wherein the particular movement range parameter defines whether an elbow of the athlete extends past a predetermined point during the athlete's performance of the at least one of the plurality of physical movement tasks.

* * * * *